United States Patent
Kamal et al.

(10) Patent No.: US 9,006,451 B1
(45) Date of Patent: Apr. 14, 2015

(54) 2-ANILINONICOTINYL BASED CHALCONES USEFUL AS POTENTIAL ANTICANCER AGENTS AND PROCESS FOR PREPARATION THEREOF

(71) Applicants: Ahmed Kamal, Hyderabad (IN); Mohammed Ashraf, Hyderabad (IN); Shaikh Faazil Bagwan, Hyderabad (IN); Yellamelli Valli Venkata Srikanth, Hyderabad (IN); Syed Mohammed Ali Hussaini, Hyderabad (IN); Adla Malla Reddy, Hyderabad (IN)

(72) Inventors: Ahmed Kamal, Hyderabad (IN); Mohammed Ashraf, Hyderabad (IN); Shaikh Faazil Bagwan, Hyderabad (IN); Yellamelli Valli Venkata Srikanth, Hyderabad (IN); Syed Mohammed Ali Hussaini, Hyderabad (IN); Adla Malla Reddy, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 14/189,766

(22) Filed: Feb. 25, 2014

(30) Foreign Application Priority Data

Oct. 4, 2013 (IN) .......................... 2958/DEL/2013

(51) Int. Cl.
*C07D 213/72* (2006.01)
*C07D 213/74* (2006.01)

(52) U.S. Cl.
CPC .................................. *C07D 213/74* (2013.01)

(58) Field of Classification Search
USPC ....................................... 546/304
See application file for complete search history.

*Primary Examiner* — Nizal Chandrakumar
(74) *Attorney, Agent, or Firm* — Kenyon & Kenyon LLP

(57) ABSTRACT

The present invention provides a compound of general formulae A useful as potential antitumor agents against human cancer cell lines and a process for the preparation thereof.

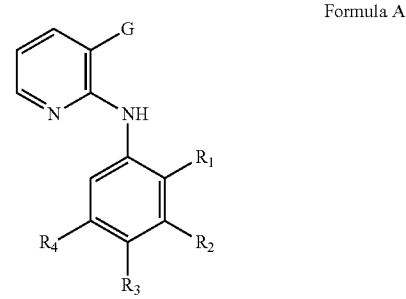

Formula A $R_1, R_2, R_3, R_4 = H$
$R_1, R_2, R_4 = H\ R_3 = NO_2$
$R_1, R_2, R_4 = H\ R_3 = OMe$
$R_1, R_2, R_4 = H\ R_3 = F$
$R_1, R_2, R_4 = H\ R_3 = Cl$
$R_1, R_2, R_4 = H\ R_3 = OH$
$R_1, R_2 = H, R_4 = H\ R_3 = OMe$
$R_1, R_2 = H, R_4, R_3 = H$
$R_1 = H, R_2, R_3 = H\ R_4 = OMe$ and G =

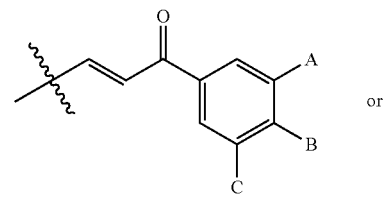

A, B, C = OMe
A, B = OMe, C = H
A = NH2, B = OMe, C = H
A = NO2, B = OMe, C = H
A, C = H, B = OME
A, C = H, B = NH2
A, C = H, B = Cl

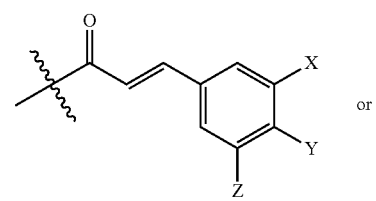

X, Y = OMe, Z = H
X, Y, Z = OME
X = H, Y = OMe, Z = OH
X = H, Y = OMe, Z = NO2
X = H, Y = OMe, Z = NH2

-continued
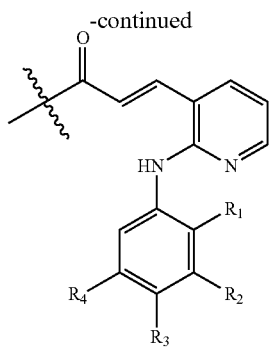
R₁, R₂, R₃, R₄ = H
R₁, R₂, R₄ = H R₃ = NO2
R₁, R₂, R₄ = H R3 = OMe
R₁, R₂, R₄ = H R₃ = F
R₁, R₂, R₄ = H R₃ = Cl
R₁, R₂, R₄ = H R₃ = OH
R₁, R₂ = H, R₄ = H R₃ = OMe
R₁, R₃, = Cl, R₄, R₃ = H
R₁ = H, R₂, R₃ = H R₄ = OMe
-continued
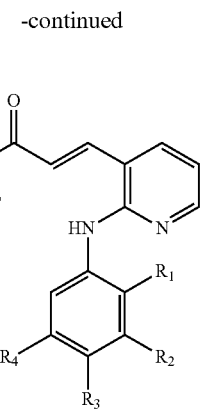
5 Claims, No Drawings

2-ANILINONICOTINYL BASED CHALCONES USEFUL AS POTENTIAL ANTICANCER AGENTS AND PROCESS FOR PREPARATION THEREOF

FIELD OF THE INVENTION

The present invention relates to 2-anilinonicotinyl based chalcones as anticancer agents and process for the preparation thereof. Particularly, the present invention relates to 2-anilinonicotinyl based chalcones of general formula A.

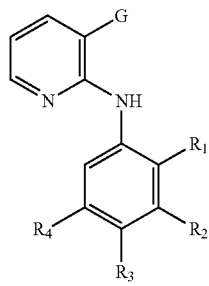

Formula A $R_1, R_2, R_3, R_4 = H$
$R_1, R_2, R_4 = H\ R_3 = NO2$
$R_1, R_2, R_4 = H\ R3 = OMe$
$R_1, R_2, R_4 = H\ R_3 = F$
$R_1, R_2, R_4 = H\ R_3 = Cl$
$R_1, R_2, R_4 = H\ R_3 = OH$
$R_1, R_2 = H, R_4 = H\ R_3 = OMe$
$R_1, R_2 = H, R_4, R_3 = H$
$R_1 = H, R_2, R_3 = H\ R_4 = OMe$   and G =

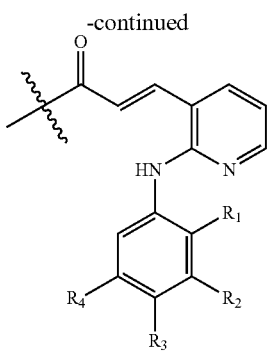

or

A, B, C = OMe
A, B = OMe, C = H
A = NH2, B = OMe, C=H
A = NO2, B = OMe, C = H
A, C = H, B = OME
A, C = H, B = NH₂
A, C = H, B = Cl

X, Y = OMe, Z = H
X, Y, Z = OME
X = H, Y = OMe, Z = OH
X = H, Y= OMe, Z = NO₂
X = H, Y = OMe, Z= NH₂

$R_1, R_2, R_3, R_4 = H$
$R_1, R_2, R_4 = H\ R_3 = NO2$
$R_1, R_2, R_4 = H\ R3 = OMe$
$R_1, R_2, R_4 = H\ R_3 = F$
$R_1, R_2, R_4 = H\ R_3 = Cl$
$R_1, R_2, R_4 = H\ R_3 = OH$
$R_1, R_2 = H, R_4 = H\ R_3 = OMe$
$R_1, R_3, = Cl, R_4, R_3 = H$
$R_1 = H, R_2, R_3 = H\ R_4 = OMe$

More particularly the present invention relates to 2-anilinonicotinyl based chalcones useful as anticancer agents. The structural formulae of these 2-anilinonicotinyl based chalcones are given below.

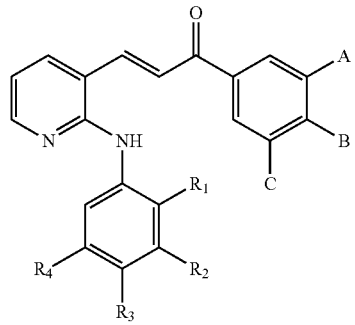

6a-bk

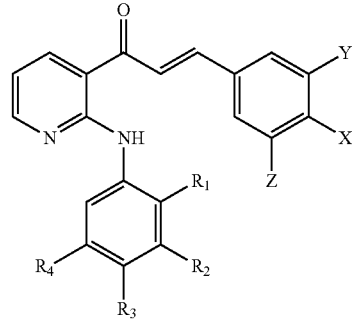

7a-as

-continued

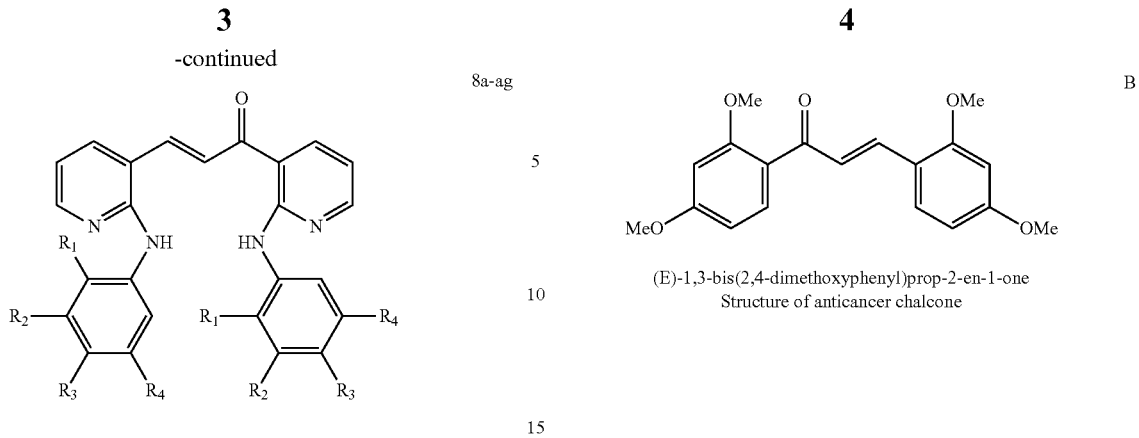

8a-ag (E)-1,3-bis(2,4-dimethoxyphenyl)prop-2-en-1-one
Structure of anticancer chalcone

BACKGROUND OF THE INVENTION

Cancer has become one of the major global health concerns and remains as the second cause of mortality after cardiovascular diseases. One of the hallmarks of cancer is the uncontrolled cell growth causing more deaths than AIDS, tuberculosis, and malaria combined and one in eight deaths worldwide is due to cancer. As it is caused by both external and internal factors, a balanced approach to cancer control includes prevention, early detection, and effective treatment. In the treatment of cancer, chemotherapy is one of the practical and widely used methods employing drugs that can destroy cancer cells by obstructing their proliferation and reproduction.

The chemotherapeutic drugs include DNA interactive agents, DNA topoisomerase I and II inhibitors, carbonic anhydrase (CA) inhibitors, CDK inhibitors, tubulin polymerization inhibitors, antimitotic agents, anti-metabolites, and miscellaneous agents affecting various cellular processes within the cancer cells. Amongst them, the tubulin binding drugs are one of the successful chemotherapeutic compounds used for cancer treatment. In addition, safety profile and side effects are the major concerns with anticancer drugs. Therefore, the development of novel agents with increased efficacy while reducing the side effects will encourage the researchers towards the drug design and development.

Inhibition of tubulin polymerization is the target of many antitumoural agents known as antimitotic agents or spindle poison and representative examples like colchicines, podophyllotoxins and combretastatins are compounds that inhibit microtubule assembly by binding to tubulin. Many chalcone moieties showed potential biological properties particularly anticancer activity. (Ahcene B., Julien B., Pierre-Alain C., Edwige N., Madeleine B., Annabelle G., Luc C., Denis W., Eva-Laure M., and Charles D., *J. Med. Chem.* 2008, 51, 2307-2310; Franco C., Rossella F., Francisco O., Francesco O, Stefano A., *J. Med. Chem.* 2009, 52, 2818-2824; Srinivas K. K.; Erin H.; Catherine P.; Hallur G., Nancy E. D., Saeed R. K.; *J. Med. Chem.* 2003, 46, 2813-2815; Vineet K.; Sarvesh K.; Mohammad H.; Hailong W.; Rajesh K. T.; Amit K.; Sunil K. S.; Virinder S. P.; Shyam B.; Sanjay V. M. *J. Med. Chem.* 2011, 54, 4147-4159; Bhat B. A.; Dhar K. L.; Puri S. C.; Saxena A. K.; Shanmugavel M.; Qazi G. N.; *Bioorg. Med. Chem. Lett.* 2005; 15, 3177-3180).

OBJECTIVES OF THE INVENTION

The main objective of the present invention is to provide novel 2-anilinonicotinyl based chalcones useful as antitumor agents.

Another object of the invention is to provide a process for the preparation of novel 2-anilinonicotinyl based chalcones.

SUMMARY OF THE INVENTION

Accordingly the present invention provides 2-anilinonicotinyl based chalcones and of general formulae A.

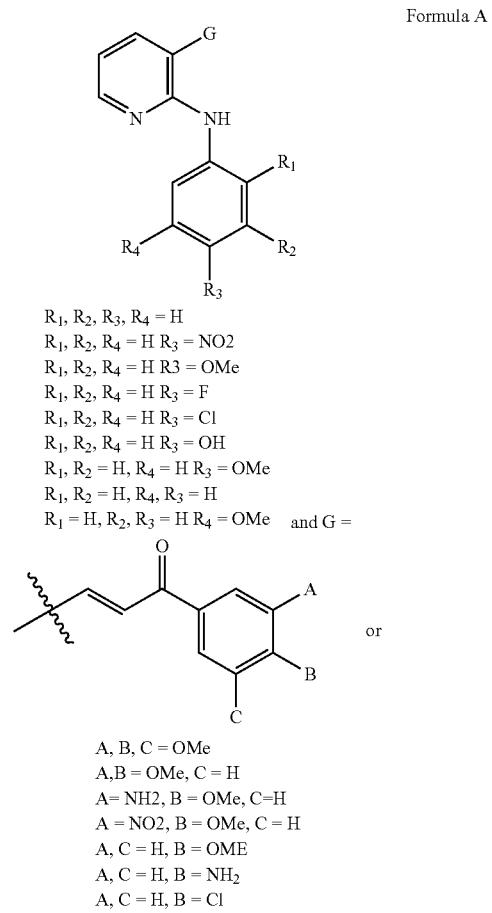

Formula A $R_1, R_2, R_3, R_4 = H$
$R_1, R_2, R_4 = H\ R_3 = NO2$
$R_1, R_2, R_4 = H\ R3 = OMe$
$R_1, R_2, R_4 = H\ R_3 = F$
$R_1, R_2, R_4 = H\ R_3 = Cl$
$R_1, R_2, R_4 = H\ R_3 = OH$
$R_1, R_2 = H, R_4 = H\ R_3 = OMe$
$R_1, R_2 = H, R_4, R_3 = H$
$R_1 = H, R_2, R_3 = H\ R_4 = OMe$ and G =

A, B, C = OMe
A, B = OMe, C = H
A = NH2, B = OMe, C=H
A = NO2, B = OMe, C = H
A, C = H, B = OME
A, C = H, B = NH2
A, C = H, B = Cl

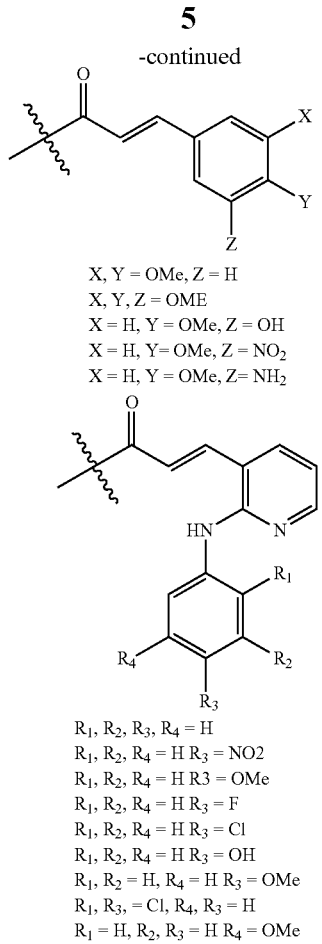

X, Y = OMe, Z = H
X, Y, Z = OME
X = H, Y = OMe, Z = OH
X = H, Y= OMe, Z = NO₂
X = H, Y = OMe, Z= NH₂

R₁, R₂, R₃, R₄ = H
R₁, R₂, R₄ = H R₃ = NO2
R₁, R₂, R₄ = H R₃ = OMe
R₁, R₂, R₄ = H R₃ = F
R₁, R₂, R₄ = H R₃ = Cl
R₁, R₂, R₄ = H R₃ = OH
R₁, R₂ = H, R₄ = H R₃ = OMe
R₁, R₃, = Cl, R₄, R₃ = H
R₁ = H, R₂, R₃ = H R₄ = OMe

In an embodiment of the present invention the novel 2-anilinonicotinyl based chalcones of formulae A, is represented by the following compounds of general formulae 6a-bk, 7a-as and 8a-ag.

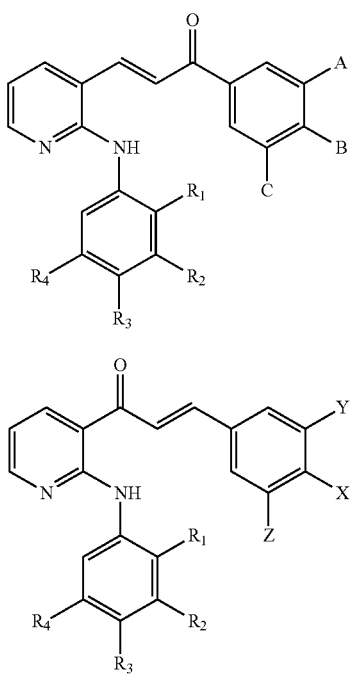

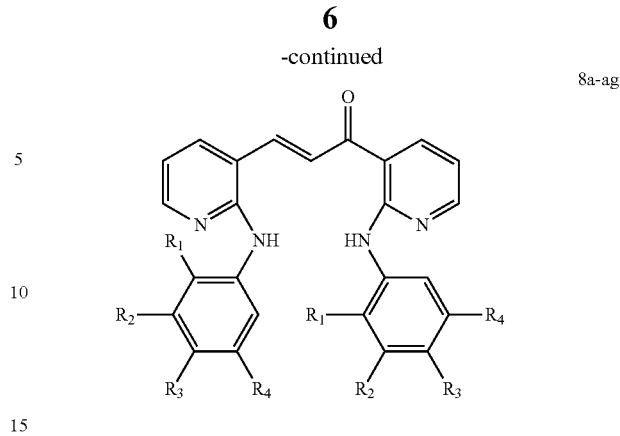

In yet another embodiment of the invention wherein the 2-anilinonicotinyl based chalcone are represented by the group of the following compounds:

(E)-3-(2-(Phenylamino)pyridin-3-yl)-1-(3,4,5-trimethoxyphenyl)prop-2-en-1-one (6a)

(E)-1-(3,4-Dimethoxyphenyl)-3-(2-(phenylamino)pyridin-3-yl)prop-2-en-1-one (6b)

(E)-1-(3-Amino-4-methoxyphenyl)-3-(2-(phenylamino)pyridin-3-yl)prop-2-en-1-one (6c)

(E)-1-(4-Methoxy-3-nitrophenyl)-3-(2-(phenylamino)pyridin-3-yl)prop-2-en-1-one (6d)

(E)-1-(4-Methoxyphenyl)-3-(2-(phenylamino)pyridin-3-yl)prop-2-en-1-one (6e)

(E)-1-(4-Aminophenyl)-3-(2-(phenylamino)pyridin-3-yl)prop-2-en-1-one (6f)

(E)-1-(4-Chlorophenyl)-3-(2-(phenylamino)pyridin-3-yl)prop-2-en-1-one (6g)

(E)-3-(2-(4-Methoxyphenylamino)pyridin-3-yl)-1-(3,4,5-trimethoxyphenyl)prop-2-en-1-one (6h)

(E)-1-(3,4-Dimethoxyphenyl)-3-(2-(4-methoxyphenylamino)pyridin-3-yl)prop-2-en-1-one (6i)

(E)-1-(3-Amino-4-methoxyphenyl)-3-(2-(4-methoxyphenylamino)pyridin-3-yl)prop-2-en-1-one (6j)

(E)-1-(4-Methoxy-3-nitrophenyl)-3-(2-(4-methoxyphenylamino)pyridin-3-yl)prop-2-en-1-one (6k)

(E)-1-(4-Methoxy-3-nitrophenyl)-3-(2-(4-methoxyphenylamino)pyridin-3-yl)prop-2-en-1-one (6l)

(E)-1-(4-Aminophenyl)-3-(2-(4-methoxyphenylamino)pyridin-3-yl)prop-2-en-1-one (6m)

(E)-1-(4-Chlorophenyl)-3-(2-(4-methoxyphenylamino)pyridin-3-yl)prop-2-en-1-one (6n)

(E)-3-(2-(3,4-Dimethoxyphenylamino)pyridin-3-yl)-1-(3,4,5-trimethoxyphenyl)prop-2-en-1-one (6o)

(E)-1-(3,4-Dimethoxyphenyl)-3-(2-(3,4-dimethoxyphenylamino)pyridin-3-yl)prop-2-en-1-one (6p)

(E)-1-(3-Amino-4-methoxyphenyl)-3-(2-(3,4-dimethoxyphenylamino)pyridin-3-yl)prop-2-en-1-one (6q)

(E)-3-(2-(3,4-Dimethoxyphenylamino)pyridin-3-yl)-1-(4-methoxy-3-nitrophenyl)prop-2-en-1-one (6r)

(E)-3-(2-(3,4-Dimethoxyphenylamino)pyridin-3-yl)-1-(4-methoxyphenyl)prop-2-en-1-one (6s)

(E)-1-(4-Aminophenyl)-3-(2-(3,4-dimethoxyphenylamino)pyridin-3-yl)prop-2-en-1-one (6t)

(E)-1-(4-Chlorophenyl)-3-(2-(3,4-dimethoxyphenylamino)pyridin-3-yl)prop-2-en-1-one (6u)

(E)-1-(3,4,5-Trimethoxyphenyl)-3-(2-(3,4,5-trimethoxyphenylamino)pyridin-3-yl)prop-2-en-1-one (6v)

(E)-1-(3,4-Dimethoxyphenyl)-3-(2-(3,4,5-trimethoxyphenylamino)pyridin-3-yl)prop-2-en-1-one (6w)

(E)-1-(3-Amino-4-methoxyphenyl)-3-(2-(3,4,5-trimethoxyphenylamino)pyridin-3-yl)prop-2-en-1-one (6x)

(E)-1-(4-Methoxy-3-nitrophenyl)-3-(2-(3,4,5-trimethoxyphenylamino)pyridin-3-yl)prop-2-en-1-one (6y)
(E)-1-(4-Methoxyphenyl)-3-(2-(3,4,5-trimethoxyphenylamino)pyridin-3-yl)prop-2-en-1-one (6z)
(E)-1-(4-Aminophenyl)-3-(2-(3,4,5-trimethoxyphenylamino)pyridin-3-yl)prop-2-en-1-one (6aa)
(E)-1-(4-Chlorophenyl)-3-(2-(3,4,5-trimethoxyphenylamino)pyridin-3-yl)prop-2-en-1-one (6ab)
(E)-3-(2-(4-Hydroxyphenylamino)pyridin-3-yl)-1-(3,4,5-trimethoxyphenyl)prop-2-en-1-one (6ac)
(E)-1-(3,4-Dimethoxyphenyl)-3-(2-(4-hydroxyphenylamino)pyridin-3-yl)prop-2-en-1-one (6ad)
(E)-1-(3-Amino-4-methoxyphenyl)-3-(2-(4-hydroxyphenylamino)pyridin-3-yl)prop-2-en-1-one (6ae)
(E)-3-(2-(4-Hydroxyphenylamino)pyridin-3-yl)-1-(4-methoxy-3-nitrophenyl)prop-2-en-1-one (6af)
(E)-3-(2-(4-Hydroxyphenylamino)pyridin-3-yl)-1-(4-methoxyphenyl)prop-2-en-1-one (6ag)
(E)-1-(4-Aminophenyl)-3-(2-(4-hydroxyphenylamino)pyridin-3-yl)prop-2-en-1-one (6ah)
(E)-1-(4-Chlorophenyl)-3-(2-(4-hydroxyphenylamino)pyridin-3-yl)prop-2-en-1-one (6ai)
(E)-3-(2-(4-Fluorophenylamino)pyridin-3-yl)-1-(3,4,5-trimethoxyphenyl)prop-2-en-1-one (6aj)
(E)-1-(3,4-Dimethoxyphenyl)-3-(2-(4-fluorophenylamino)pyridin-3-yl)prop-2-en-1-one (6ak)
(E)-1-(3-Amino-4-methoxyphenyl)-3-(2-(4-fluorophenylamino)pyridin-3-yl)prop-2-en-1-one (6al)
(E)-3-(2-(4-Fluorophenylamino)pyridin-3-yl)-1-(4-methoxy-3-nitrophenyl)prop-2-en-1-one (6am)
(E)-3-(2-(4-Fluorophenylamino)pyridin-3-yl)-1-(4-methoxyphenyl)prop-2-en-1-one (6an)
(E)-1-(4-Aminophenyl)-3-(2-(4-fluorophenylamino)pyridin-3-yl)prop-2-en-1-one (6ao)
(E)-1-(4-Chlorophenyl)-3-(2-(4-fluorophenylamino)pyridin-3-yl)prop-2-en-1-one (6ap)
(E)-3-(2-(2,4-Dichlorophenylamino)pyridin-3-yl)-1-(3,4,5-trimethoxyphenyl)prop-2-en-1-one (6aq)
(E)-3-(2-(2,4-Dichlorophenylamino)pyridin-3-yl)-1-(3,4-dimethoxyphenyl)prop-2-en-1-one (6ar)
(E)-1-(3-Amino-4-methoxyphenyl)-3-(2-(2,4-dichlorophenylamino)pyridin-3-yl)prop-2-en-1-one (6as)
(E)-3-(2-(2,4-Dichlorophenylamino)pyridin-3-yl)-1-(4-methoxy-3-nitrophenyl)prop-2-en-1-one (6at)
(E)-3-(2-(2,4-Dichlorophenylamino)pyridin-3-yl)-1-(4-methoxyphenyl)prop-2-en-1-one (6au)
(E)-1-(4-Aminophenyl)-3-(2-(2,4-dichlorophenylamino)pyridin-3-yl)prop-2-en-1-one (6av)
(E)-1-(4-Chlorophenyl)-3-(2-(2,4-dichlorophenylamino)pyridin-3-yl)prop-2-en-1-one (6aw)
(E)-3-(2-(4-Chlorophenylamino)pyridin-3-yl)-1-(3,4,5-trimethoxyphenyl)prop-2-en-1-one (6ax)
(E)-3-(2-(4-Chlorophenylamino)pyridin-3-yl)-1-(3,4-dimethoxyphenyl)prop-2-en-1-one (6ay)
(E)-1-(3-Amino-4-methoxyphenyl)-3-(2-(4-chlorophenylamino)pyridin-3-yl)prop-2-en-1-one (6az)
(E)-3-(2-(4-Chlorophenylamino)pyridin-3-yl)-1-(4-methoxy-3-nitrophenyl)prop-2-en-1-one (6ba)
(E)-3-(2-(4-Chlorophenylamino)pyridin-3-yl)-1-(4-methoxyphenyl)prop-2-en-1-one (6bb)
(E)-1-(4-Aminophenyl)-3-(2-(4-chlorophenylamino)pyridin-3-yl)prop-2-en-1-one (6bc)
(E)-1-(4-Chlorophenyl)-3-(2-(4-chlorophenylamino)pyridin-3-yl)prop-2-en-1-one (6bd)
(E)-3-(2-(4-Nitrophenylamino)pyridin-3-yl)-1-(3,4,5-trimethoxyphenyl)prop-2-en-1-one (6be)
(E)-1-(3,4-Dimethoxyphenyl)-3-(2-(4-nitrophenylamino)pyridin-3-yl)prop-2-en-1-one (6bf)
(E)-1-(3,4-Dimethoxyphenyl)-3-(2-(4-nitrophenylamino)pyridin-3-yl)prop-2-en-1-one (6bg)
(E)-1-(3-Amino-4-methoxyphenyl)-3-(2-(4-nitrophenylamino)pyridin-3-yl)prop-2-en-1-one (6bh)
(E)-1-(4-Methoxyphenyl)-3-(2-(4-nitrophenylamino)pyridin-3-yl)prop-2-en-1-one (6bi)
(E)-1-(4-Aminophenyl)-3-(2-(4-nitrophenylamino)pyridin-3-yl)prop-2-en-1-one (6bj)
(E)-1-(4-Chlorophenyl)-3-(2-(4-nitrophenylamino)pyridin-3-yl)prop-2-en-1-one (6bk)
(E)-1-(2-(Phenylamino)pyridin-3-yl)-3-(3,4,5-trimethoxyphenyl)prop-2-en-1-one (7a)
(E)-1-(2-(4-Methoxyphenylamino)pyridin-3-yl)-3-(3,4,5-trimethoxyphenyl)prop-2-en-1-one (7b)
(E)-1-(2-(3,4-Dimethoxyphenylamino)pyridin-3-yl)-3-(3,4,5-trimethoxyphenyl)prop-2-en-1-one (7c)
(E)-3-(3,4,5-Trimethoxyphenyl)-1-(2-(3,4,5-trimethoxyphenylamino)pyridin-3-yl)prop-2-en-1-one (7d)
(E)-1-(2-(4-Hydroxyphenylamino)pyridin-3-yl)-3-(3,4,5-trimethoxyphenyl)prop-2-en-1-one (7e)
(E)-1-(2-(4-Fluorophenylamino)pyridin-3-yl)-3-(3,4,5-trimethoxyphenyl)prop-2-en-1-one (7f)
(E)-1-(2-(2,4-Dichlorophenylamino)pyridin-3-yl)-3-(3,4,5-trimethoxyphenyl)prop-2-en-1-one (7g)
(E)-1-(2-(4-Chlorophenylamino)pyridin-3-yl)-3-(3,4,5-trimethoxyphenyl)prop-2-en-1-one (7h)
(E)-1-(2-(4-Ntrophenylamino)pyridin-3-yl)-3-(3,4,5-trimethoxyphenyl)prop-2-en-1-one (7i)
(E)-3-(3,4-Dimethoxyphenyl)-1-(2-(phenylamino)pyridin-3-yl)prop-2-en-1-one (7j)
(E)-3-(3,4-Dimethoxyphenyl)-1-(2-(4-methoxyphenylamino)pyridin-3-yl)prop-2-en-1-one (7k)
(E)-3-(3,4-Dimethoxyphenyl)-1-(2-(3,4-dimethoxyphenylamino)pyridin-3-yl)prop-2-en-1-one (7l)
(E)-3-(3,4-Dimethoxyphenyl)-1-(2-(3,4,5-trimethoxyphenylamino)pyridin-3-yl)prop-2-en-1-one (7m)
(E)-3-(3,4-Dimethoxyphenyl)-1-(2-(4-hydroxyphenylamino)pyridin-3-yl)prop-2-en-1-one (7n)
(E)-3-(3,4-Dimethoxyphenyl)-1-(2-(4-fluorophenylamino)pyridin-3-yl)prop-2-en-1-one (7o)
(E)-1-(2-(2,4-Dichlorophenylamino)pyridin-3-yl)-3-(3,4-dimethoxyphenyl)prop-2-en-1-one (7p)
(E)-1-(2-(4-Chlorophenylamino)pyridin-3-yl)-3-(3,4-dimethoxyphenyl)prop-2-en-1-one (7q)
(E)-3-(3,4-Dimethoxyphenyl)-1-(2-(4-nitrophenylamino)pyridin-3-yl)prop-2-en-1-one (7r)
(E)-3-(3-Amino-4-methoxyphenyl)-1-(2-(phenylamino)pyridin-3-yl)prop-2-en-1-one (7s)
(E)-3-(3-Amino-4-methoxyphenyl)-1-(2-(4-methoxyphenylamino)pyridin-3-yl)prop-2-en-1-one (7t)
(E)-3-(3-Amino-4-methoxyphenyl)-1-(2-(3,4-dimethoxyphenylamino)pyridin-3-yl)prop-2-en-1-one (7u)
(E)-3-(3-Amino-4-methoxyphenyl)-1-(2-(4-hydroxyphenylamino)pyridin-3-yl)prop-2-en-1-one (7v)
(E)-3-(3-Amino-4-methoxyphenyl)-1-(2-(3,4,5-trimethoxyphenylamino)pyridin-3-yl)prop-2-en-1-one (7w)
(E)-3-(3-Amino-4-methoxyphenyl)-1-(2-(4-fluorophenylamino)pyridin-3-yl)prop-2-en-1-one (7x)
(E)-3-(3-Amino-4-methoxyphenyl)-1-(2-(2,4-dichlorophenylamino)pyridin-3-yl)prop-2-en-1-one (7y)
(E)-3-(3-Amino-4-methoxyphenyl)-1-(2-(4-chlorophenylamino)pyridin-3-yl)prop-2-en-1-one (7z)
(E)-3-(3-Amino-4-methoxyphenyl)-1-(2-(4-nitrophenylamino)pyridin-3-yl)prop-2-en-1-one (7aa)

(E)-3-(3-Hydroxy-4-methoxyphenyl)-1-(2-(phenylamino)pyridin-3-yl)prop-2-en-1-one (7ab)

(E)-3-(3-Hydroxy-4-methoxyphenyl)-1-(2-(4-methoxyphenylamino)pyridin-3-yl)prop-2-en-1-one (7ac)

(E)-1-(2-(3,4-Dimethoxyphenylamino)pyridin-3-yl)-3-(3-hydroxy-4-methoxyphenyl)prop-2-en-1-one (7ad)

(E)-3-(3-Hydroxy-4-methoxyphenyl)-1-(2-(4-hydroxyphenylamino)pyridin-3-yl)prop-2-en-1-one (7ae)

(E)-3-(3-Hydroxy-4-methoxyphenyl)-1-(2-(3,4,5-trimethoxyphenylamino)pyridin-3-yl)prop-2-en-1-one (7af)

(E)-1-(2-(4-Fluorophenylamino)pyridin-3-yl)-3-(3-hydroxy-4-methoxyphenyl)prop-2-en-1-one (7ag)

(E)-1-(2-(2,4-Dichlorophenylamino)pyridin-3-yl)-3-(3-hydroxy-4-methoxyphenyl)prop-2-en-1-one (7ah)

(E)-1-(2-(4-Chlorophenylamino)pyridin-3-yl)-3-(3-hydroxy-4-methoxyphenyl)prop-2-en-1-one (7ai)

(E)-3-(4-Methoxy-3-nitrophenyl)-1-(2-(phenylamino)pyridin-3-yl)prop-2-en-1-one (7aj)

(E)-3-(3-Hydroxy-4-methoxyphenyl)-1-(2-(4-nitrophenylamino)pyridin-3-yl)prop-2-en-1-one (7ak)

(E)-3-(4-Methoxy-3-nitrophenyl)-1-(2-(4-methoxyphenylamino)pyridin-3-yl)prop-2-en-1-one (7al)

(E)-1-(2-(3,4-Dimethoxyphenylamino)pyridin-3-yl)-3-(4-methoxy-3-nitrophenyl)prop-2-en-1-one (7am)

(E)-3-(4-Methoxy-3-nitrophenyl)-1-(2-(3,4,5-trimethoxyphenylamino)pyridin-3-yl)prop-2-en-1-one (7an)

(E)-1-(2-(4-Hydroxyphenylamino)pyridin-3-yl)-3-(4-methoxy-3-nitrophenyl)prop-2-en-1-one (7ao)

(E)-1-(2-(4-Fluorophenylamino)pyridin-3-yl)-3-(4-methoxy-3-nitrophenyl)prop-2-en-1-one (7ap)

(E)-1-(2-(2,4-Dichlorophenylamino)pyridin-3-yl)-3-(4-methoxy-3-nitrophenyl)prop-2-en-1-one (7aq)

(E)-1-(2-(4-Chlorophenylamino)pyridin-3-yl)-3-(4-methoxy-3-nitrophenyl)prop-2-en-1-one (7ar)

(E)-3-(4-Methoxy-3-nitrophenyl)-1-(2-(4-nitrophenylamino)pyridin-3-yl)prop-2-en-1-one (7as)

(E)-3-(2-(4-Methoxyphenylamino)pyridin-3-yl)-1-(2-(phenylamino)pyridin-3-yl)prop-2-en-1-on ze (8a)

(E)-3-(2-(3,4-Dimethoxyphenylamino)pyridin-3-yl)-1-(2-(phenylamino)pyridin-3-yl)prop-2-en-1-one (8b)

(E)-1-(2-(Phenylamino)pyridin-3-yl)-3-(2-(3,4,5-trimethoxyphenylamino)pyridin-3-yl)prop-2-en-1-one (8c)

(E)-3-(2-(4-Hydroxyphenylamino)pyridin-3-yl)-1-(2-(phenylamino)pyridin-3-yl)prop-2-en-1-one (8d)

(E)-3-(2-(4-Fluorophenylamino)pyridin-3-yl)-1-(2-(phenylamino)pyridin-3-yl)prop-2-en-1-one (8e)

(E)-3-(2-(2,4-Dichlorophenylamino)pyridin-3-yl)-1-(2-(phenylamino)pyridin-3-yl)prop-2-en-1-one (8f)

(E)-3-(2-(4-Nitrophenylamino)pyridin-3-yl)-1-(2-(phenylamino)pyridin-3-yl)prop-2-en-1-one (8g)

(E)-1-(2-(4-Methoxyphenylamino)pyridin-3-yl)-3-(2-(phenylamino)pyridin-3-yl)prop-2-en-1-one (8h)

(E)-3-(2-(3,4-Dimethoxyphenylamino)pyridin-3-yl)-1-(2-(4-methoxyphenylamino)pyridin-3-yl)prop-2-en-1-one (8i)

(E)-1-(2-(4-Methoxyphenylamino)pyridin-3-yl)-3-(2-(3,4,5-trimethoxyphenylamino)pyridin-3-yl)prop-2-en-1-one (8j)

(E)-3-(2-(4-Hydroxyphenylamino)pyridin-3-yl)-1-(2-(4-methoxyphenylamino)pyridin-3-yl)prop-2-en-1-one (8k)

(E)-3-(2-(4-Fluorophenylamino)pyridin-3-yl)-1-(2-(4-methoxyphenylamino)pyridin-3-yl)prop-2-en-1-one (8l)

(E)-3-(2-(4-Chlorophenylamino)pyridin-3-yl)-1-(2-(4-methoxyphenylamino)pyridin-3-yl)prop-2-en-1-one (8m)

(E)-3-(2-(2,4-Dichlorophenylamino)pyridin-3-yl)-1-(2-(4-methoxyphenylamino)pyridin-3-yl)prop-2-en-1-one (8n)

(E)-3-(2-(3,4-Dimethoxyphenylamino)pyridin-3-yl)-1-(2-(4-hydroxyphenylamino)pyridin-3-yl)prop-2-en-1-one (8o)

(E)-1-(2-(4-Hydroxyphenylamino)pyridin-3-yl)-3-(2-(3,4,5-trimethoxyphenylamino)pyridin-3-yl)prop-2-en-1-one (8p)

(E)-3-(2-(4-Fluorophenylamino)pyridin-3-yl)-1-(2-(4-hydroxyphenylamino)pyridin-3-yl)prop-2-en-1-one (8q)

(E)-3-(2-(4-Chlorophenylamino)pyridin-3-yl)-1-(2-(4-hydroxyphenylamino)pyridin-3-yl)prop-2-en-1-one (8r)

(E)-3-(2-(2,4-Dichlorophenylamino)pyridin-3-yl)-1-(2-(4-hydroxyphenylamino)pyridin-3-yl)prop-2-en-1-one (8s)

(E)-1-(2-(4-Hydroxyphenylamino)pyridin-3-yl)-3-(2-(4-nitrophenylamino)pyridin-3-yl)prop-2-en-1-one (8t)

(E)-1-(2-(4-Fluorophenylamino)pyridin-3-yl)-3-(2-(4-methoxyphenylamino)pyridin-3-yl)prop-2-en-1-one (8u)

(E)-3-(2-(3,4-Dimethoxyphenylamino)pyridin-3-yl)-1-(2-(4-fluorophenylamino)pyridin-3-yl)prop-2-en-1-one (8v)

(E)-1-(2-(4-Fluorophenylamino)pyridin-3-yl)-3-(2-(3,4,5-trimethoxyphenylamino)pyridin-3-yl)prop-2-en-1-one (8w)

(E)-3-(2-(4-Chlorophenylamino)pyridin-3-yl)-1-(2-(4-fluorophenylamino)pyridin-3-yl)prop-2-en-1-one (8x)

(E)-3-(2-(2,4-Dichlorophenylamino)pyridin-3-yl)-1-(2-(4-fluorophenylamino)pyridin-3-yl)prop-2-en-1-one (8y)

(E)-1-(2-(4-Fluorophenylamino)pyridin-3-yl)-3-(2-(4-nitrophenylamino)pyridin-3-yl)prop-2-en-1-one (8z)

(E)-3-(2-(3,4-Dimethoxyphenylamino)pyridin-3-yl)-1-(2-(3,4,5-trimethoxyphenylamino)pyridin-3-yl)prop-2-en-1-one (8aa)

(E)-3-(2-(4-Nitrophenylamino)pyridin-3-yl)-1-(2-(3,4,5-trimethoxyphenylamino)pyridin-3-yl)prop-2-en-1-one (8ab)

(E)-3-(2-(4-Chlorophenylamino)pyridin-3-yl)-1-(2-(3,4,5-trimethoxyphenylamino)pyridin-3-yl)prop-2-en-1-one (8ac)

(E)-3-(2-(2,3-Dichlorophenylamino)pyridin-3-yl)-1-(2-(3,4,5-trimethoxyphenylamino)pyridin-3-yl)prop-2-en-1-one (8ad)

(E)-3-(2-(4-Chlorophenylamino)pyridin-3-yl)-1-(2-(4-nitrophenylamino)pyridin-3-yl)prop-2-en-1-one (8ae)

(E)-3-(2-(3,4-Dimethoxyphenylamino)pyridin-3-yl)-1-(2-(4-nitrophenylamino)pyridin-3-yl)prop-2-en-1-one (8af)

(E)-3-(2-(2,4-Dichlorophenylamino)pyridin-3-yl)-1-(2-(4-nitrophenylamino)pyridin-3-yl)prop-2-en-1-one (8ag)

In yet another embodiment of the invention wherein 2-anilinonicotinyl based chalcone wherein the structural formulae of the representative compounds comprising:

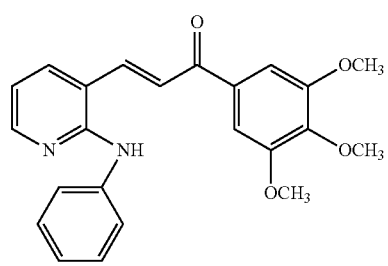

6a

-continued
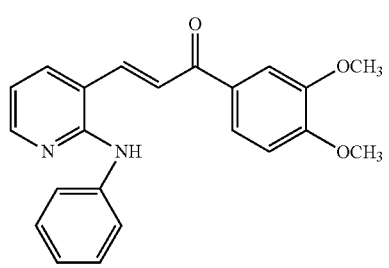
6b
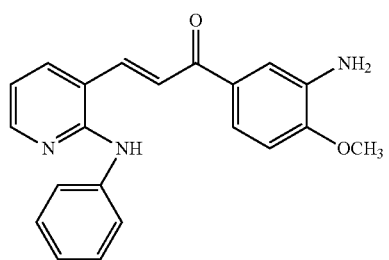
6c
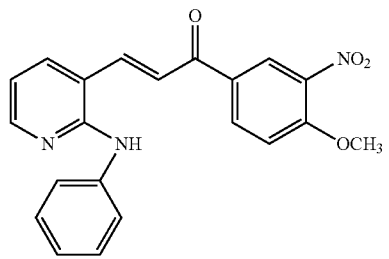
6d
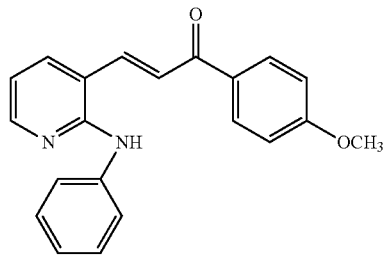
6e
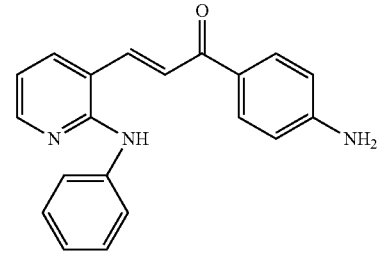
6f
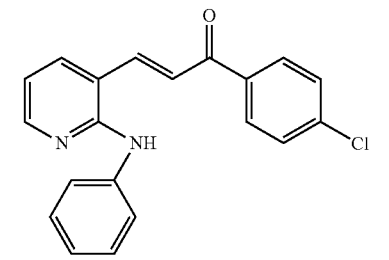
6g
-continued
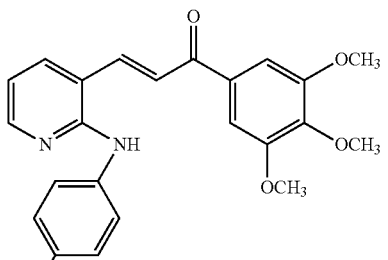
6h
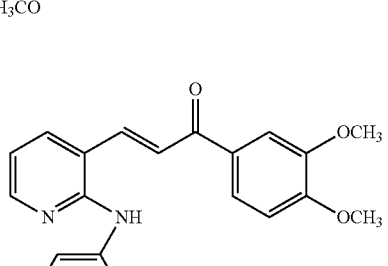
6i
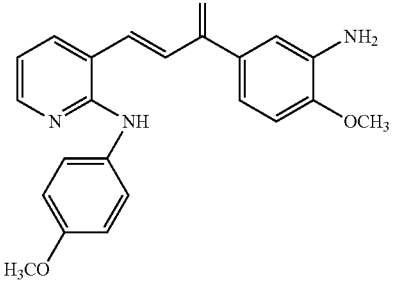
6j
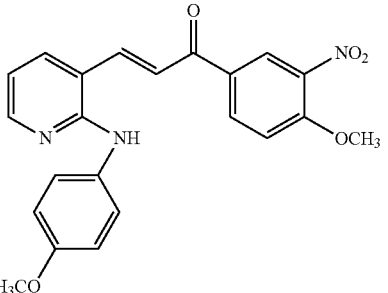
6k
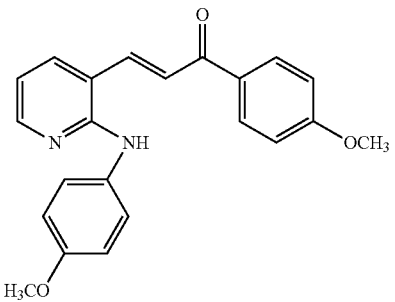
6l

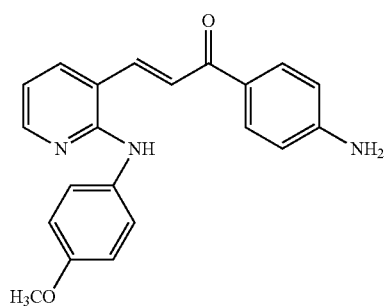
6m
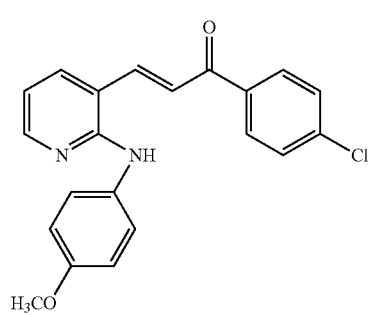
6n
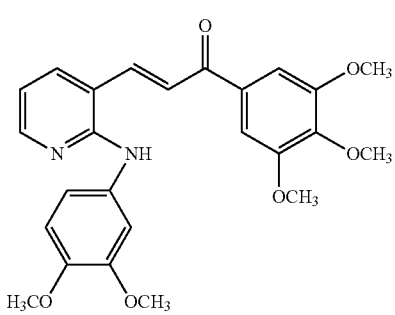
6o
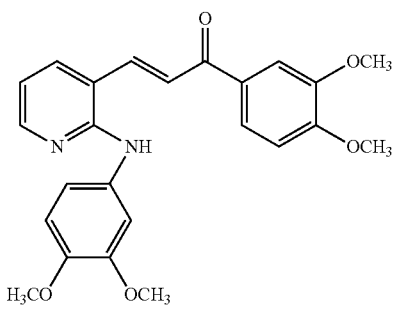
6p
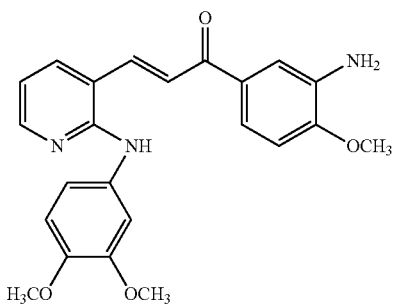
6q
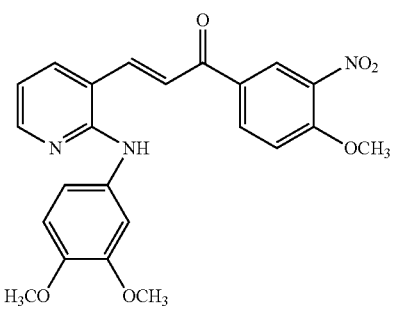
6r
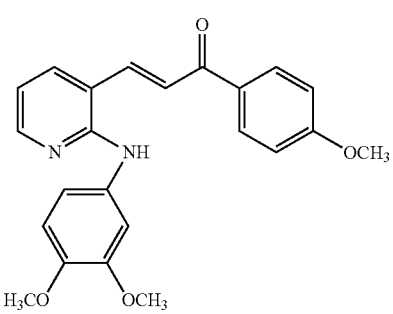
6s
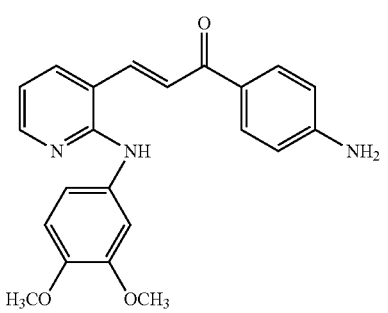
6t
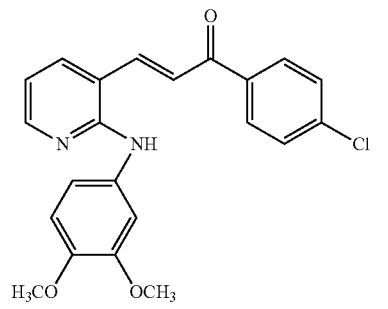
6u
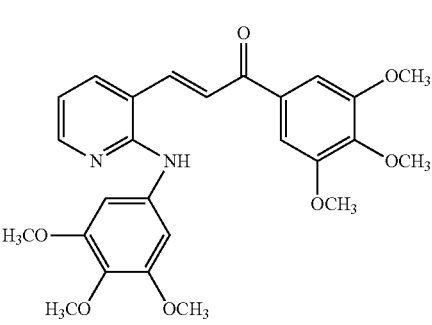
6v

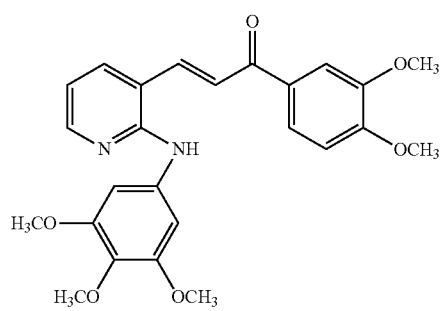
6w
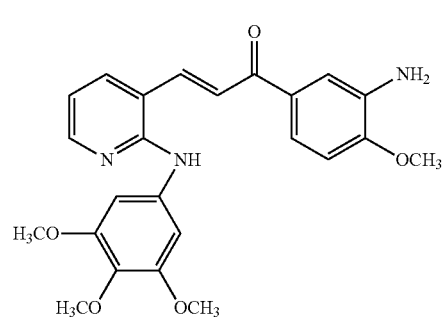
6x
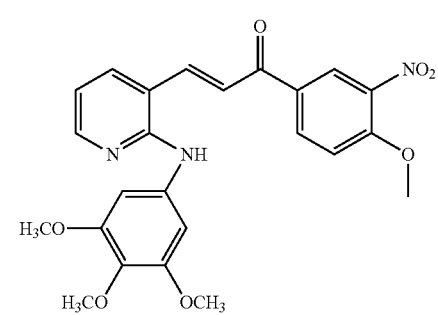
6y
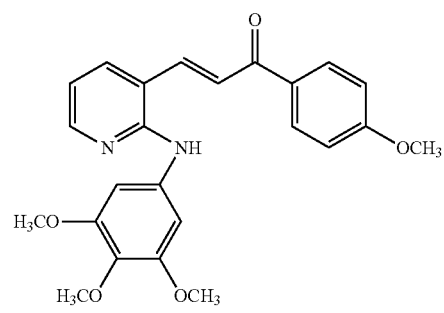
6z
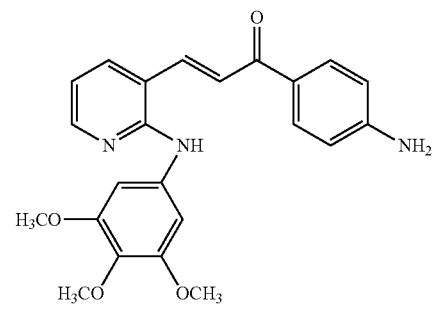
6aa
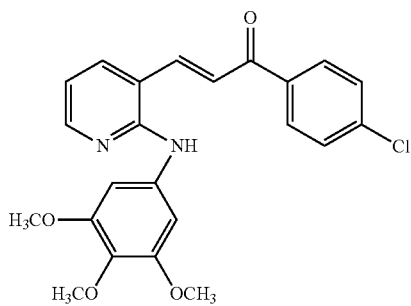
6ab
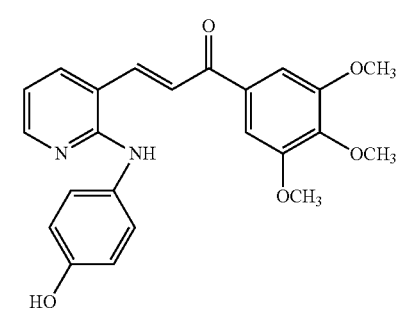
6ac
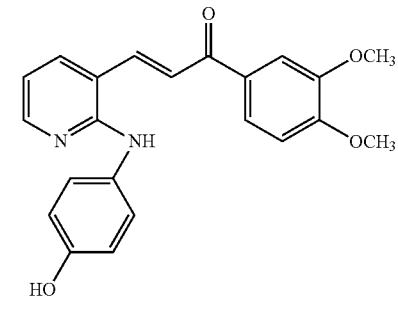
6ad
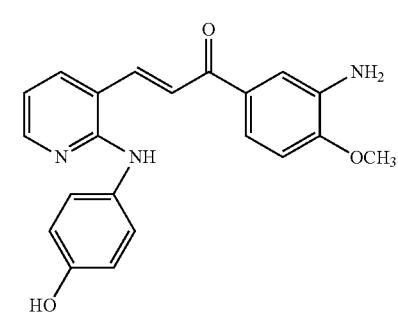
6ae
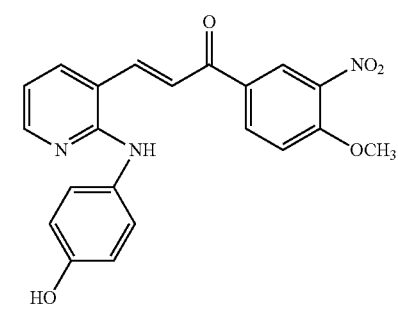
6af

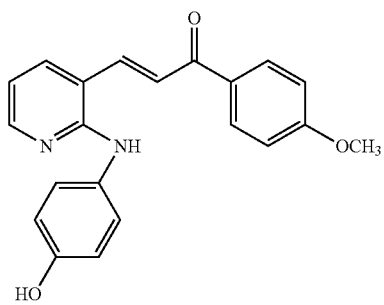 6ag
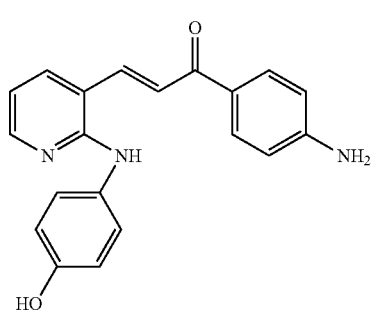 6ah
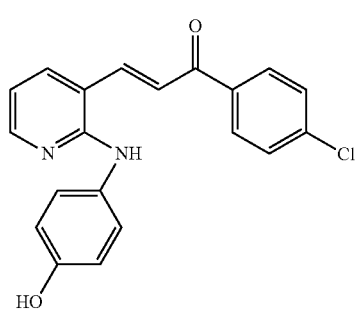 6ai
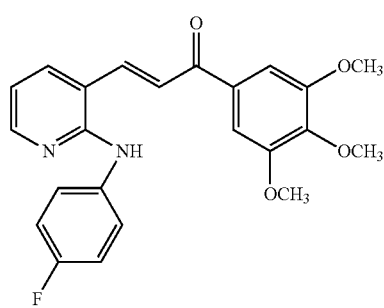 6aj
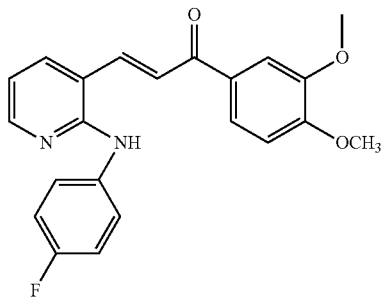 6ak
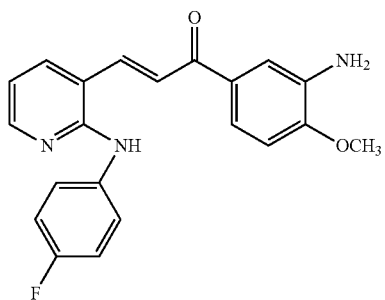 6al
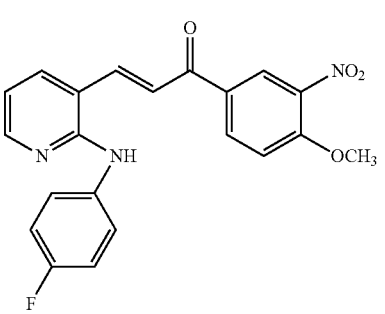 6am
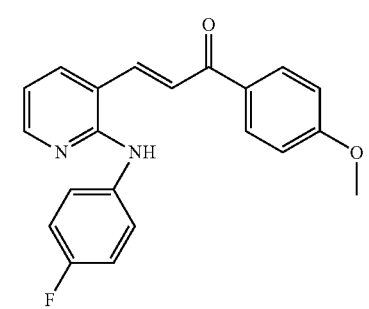 6an
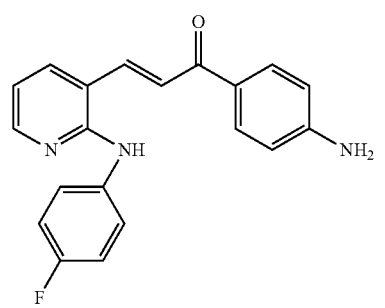 6ao
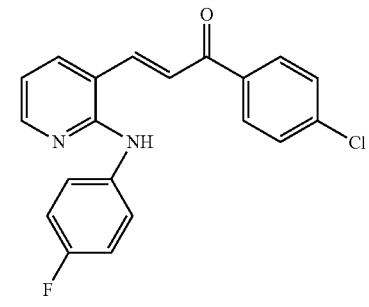 6ap

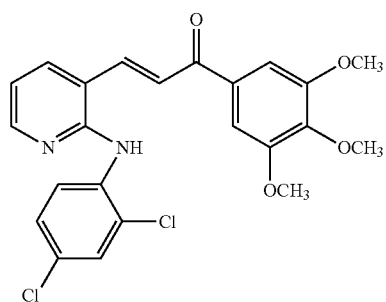
6aq
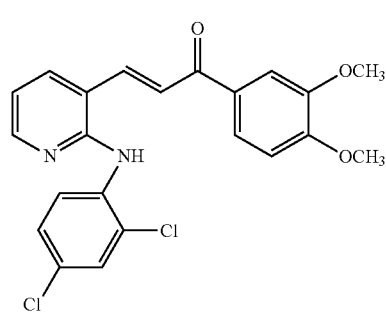
6ar
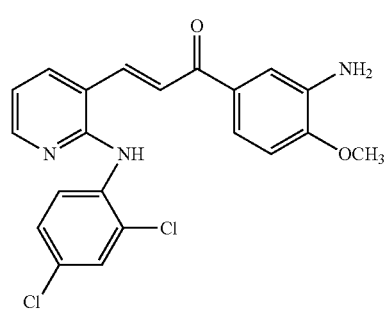
6as
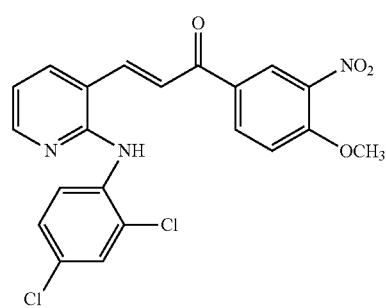
6at
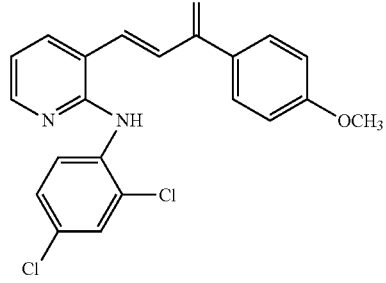
6au
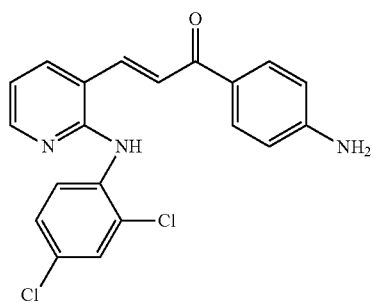
6av
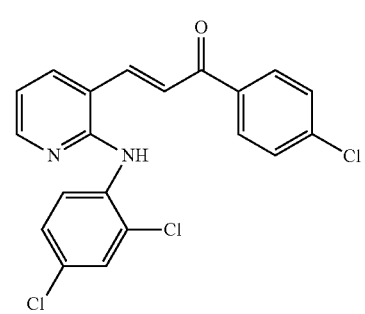
6aw
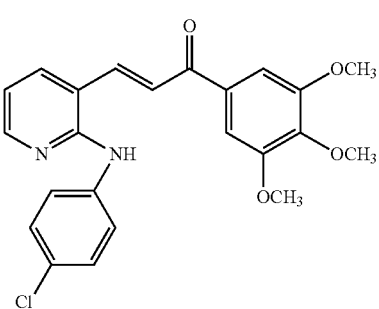
6ax
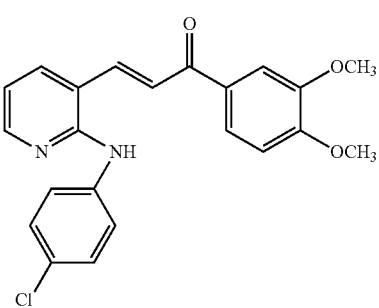
6ay
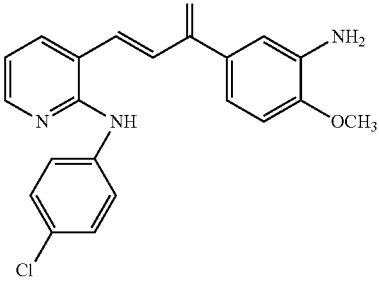
6az -continued
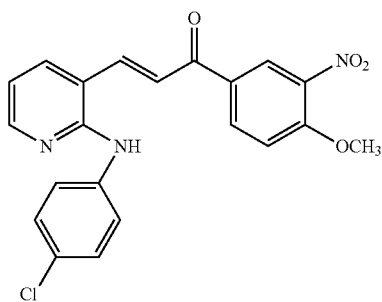
6ba
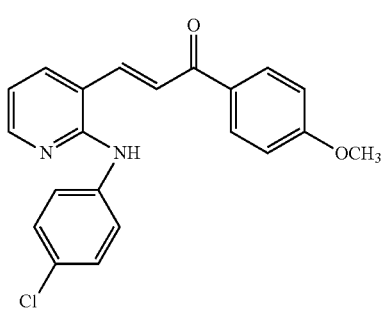
6bb
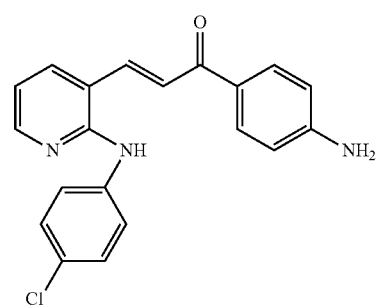
6bc
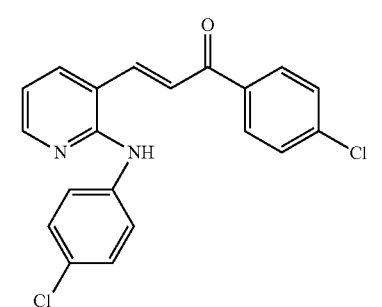
6bd
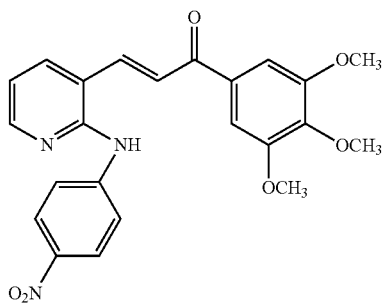
6be
-continued
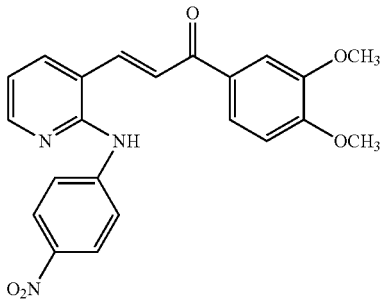
6bf
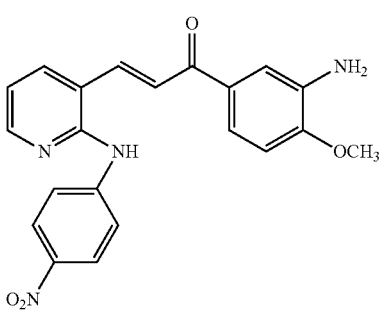
6bg
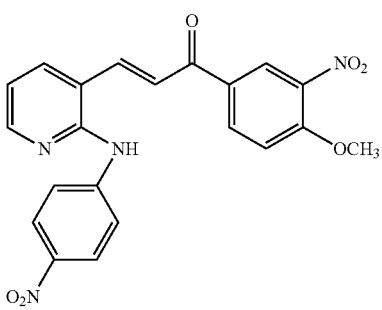
6bh
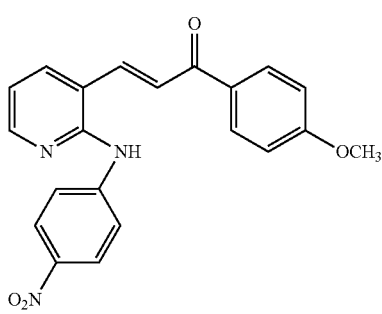
6bi
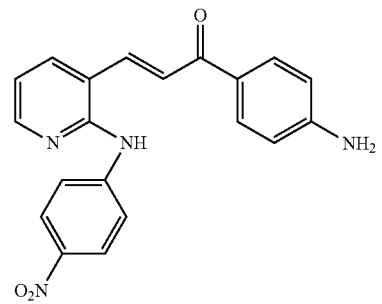
6bj

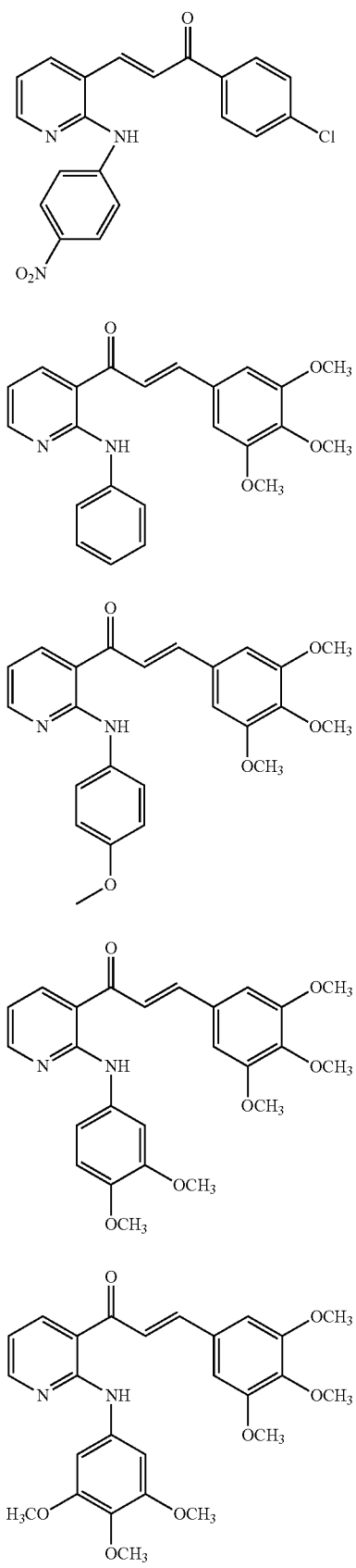
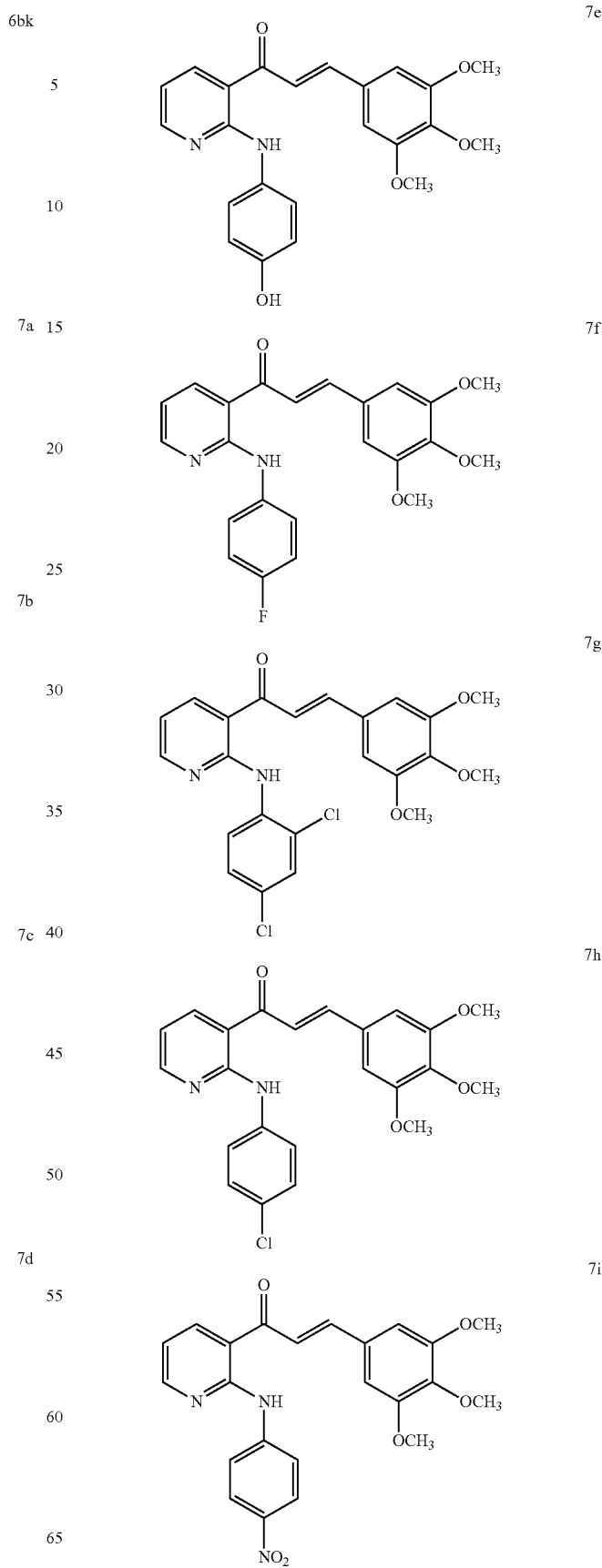

-continued
7j
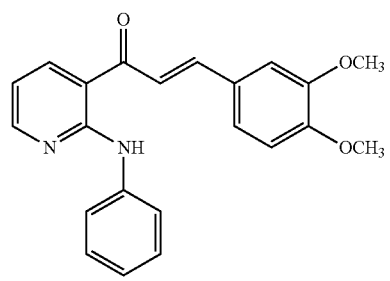
7k
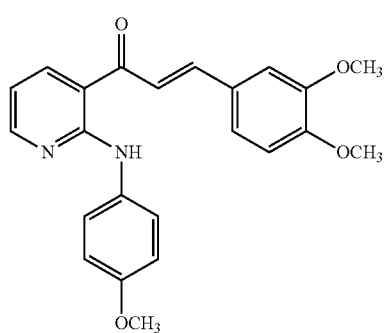
7l
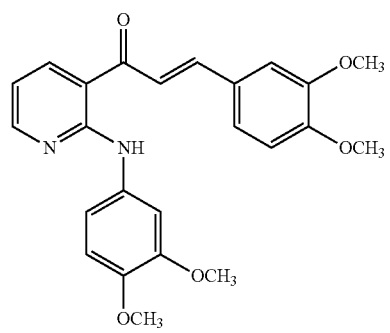
7m
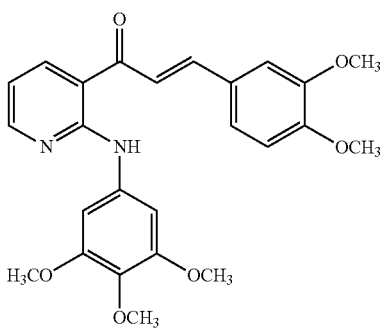
7n
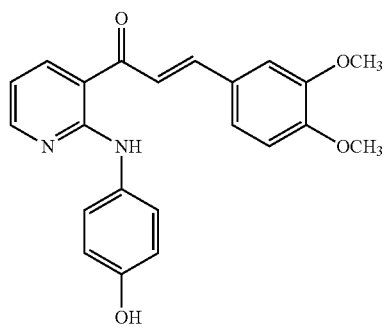
-continued
7o
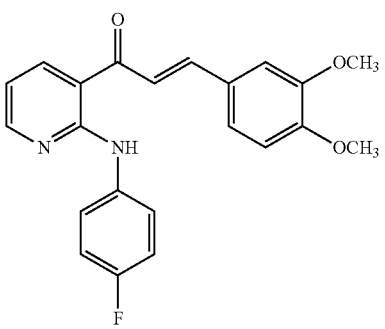
7p
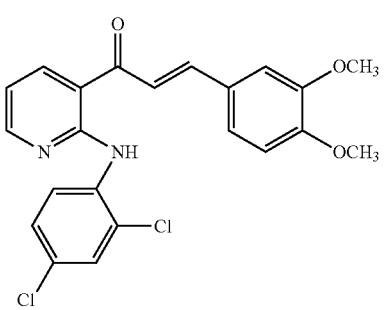
7q
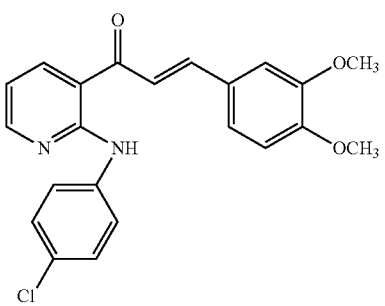
7r
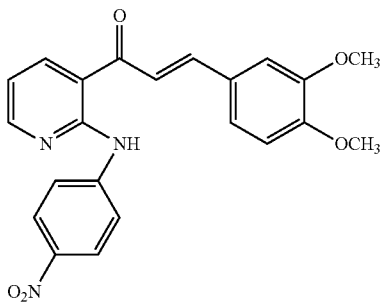
7s
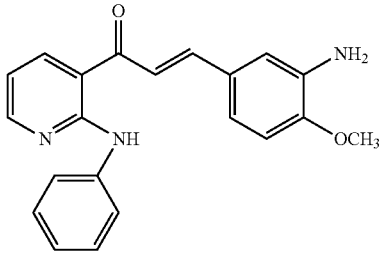

7t
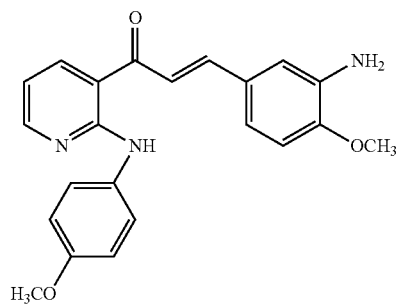
7u
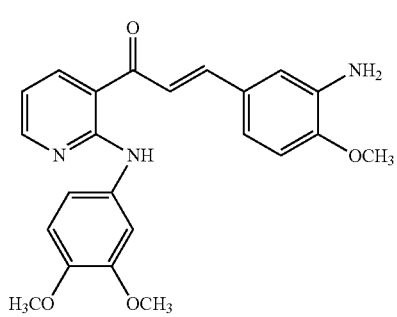
7v
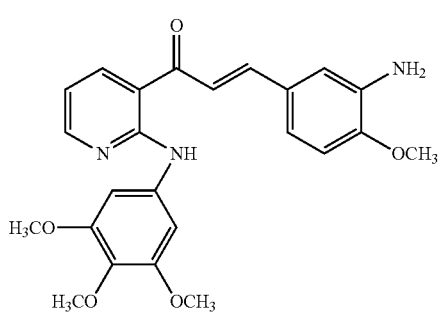
7w
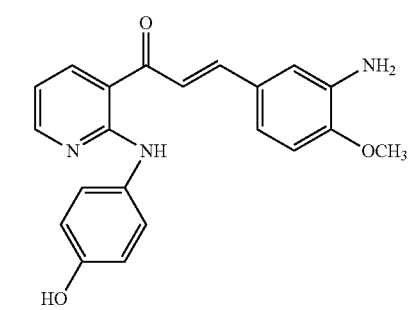
7x
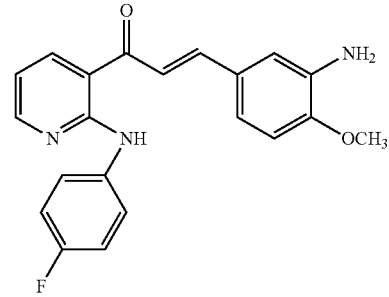
7y
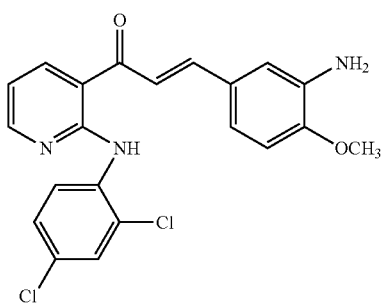
7z
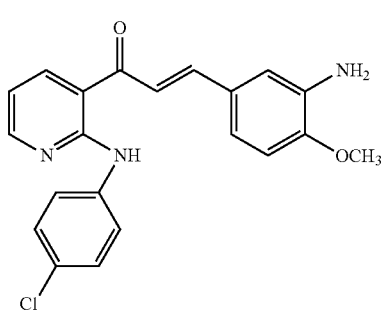
7aa
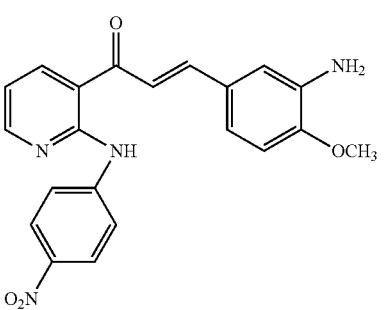
7ab
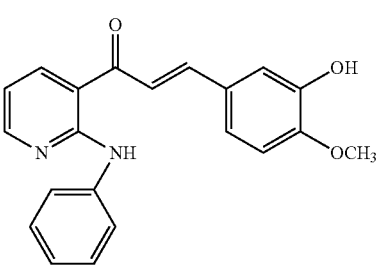
7ac
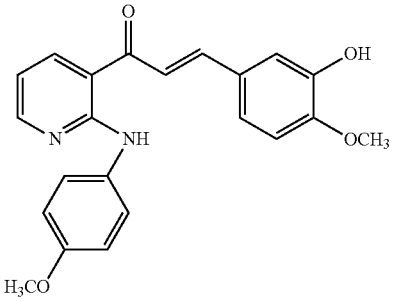

7ad
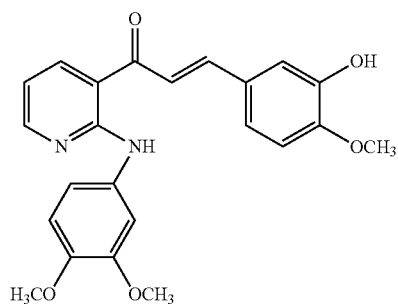
7ai
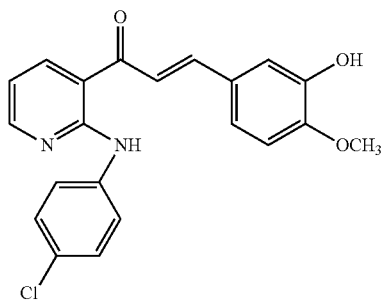
7ae
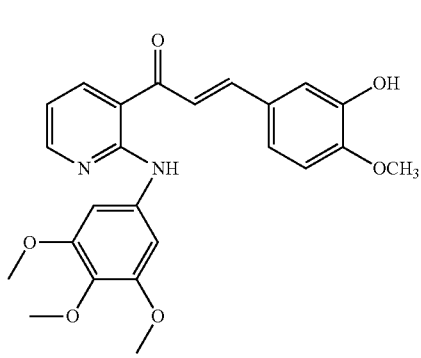
7aj
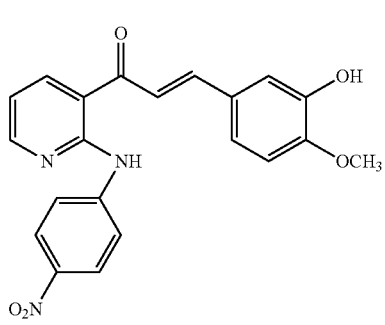
7af
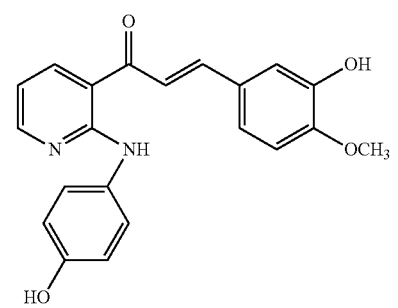
7ak
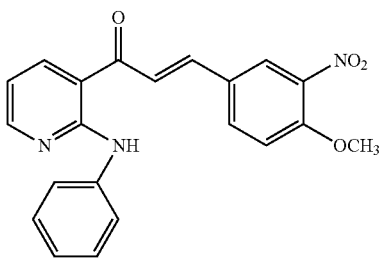
7ag
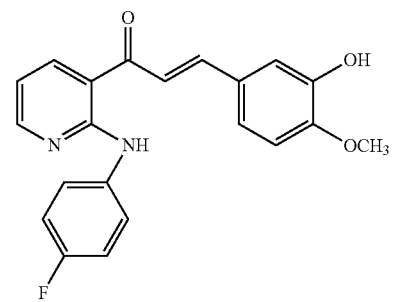
7al
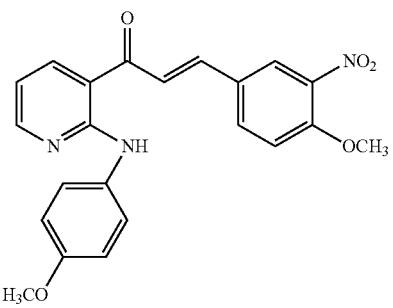
7ah
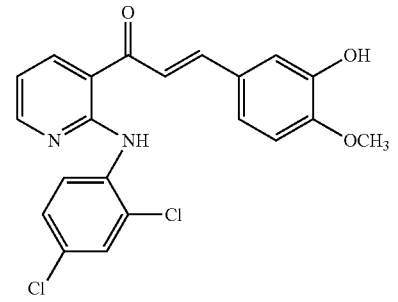
7am
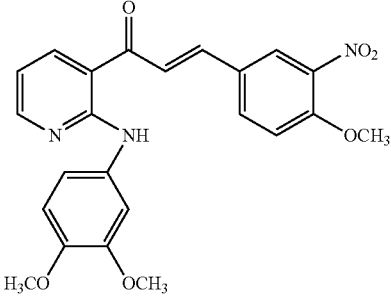

7an 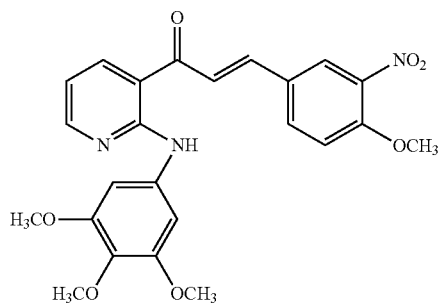
7ao 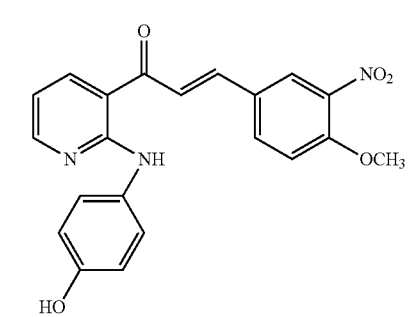
7ap 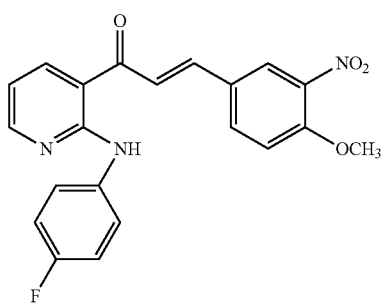
7aq 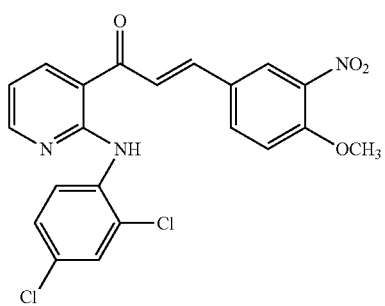
7ar 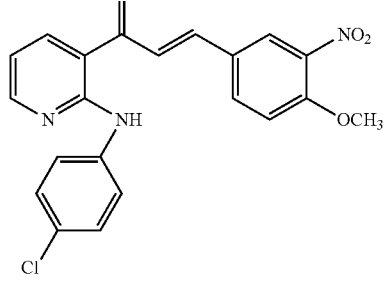
7as 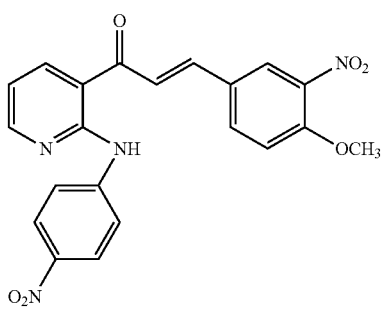
8a 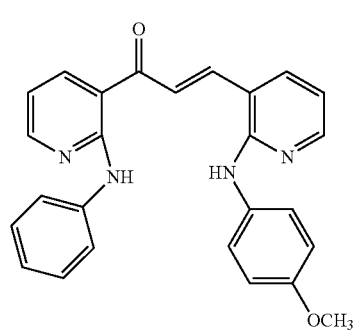
8b 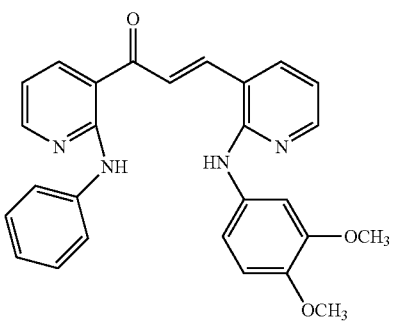
8c 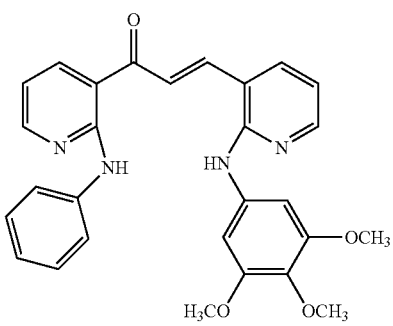
8d 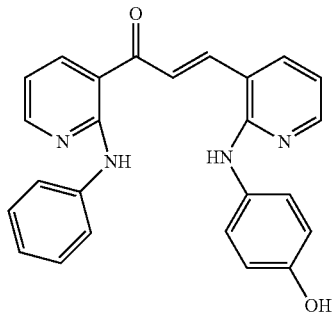

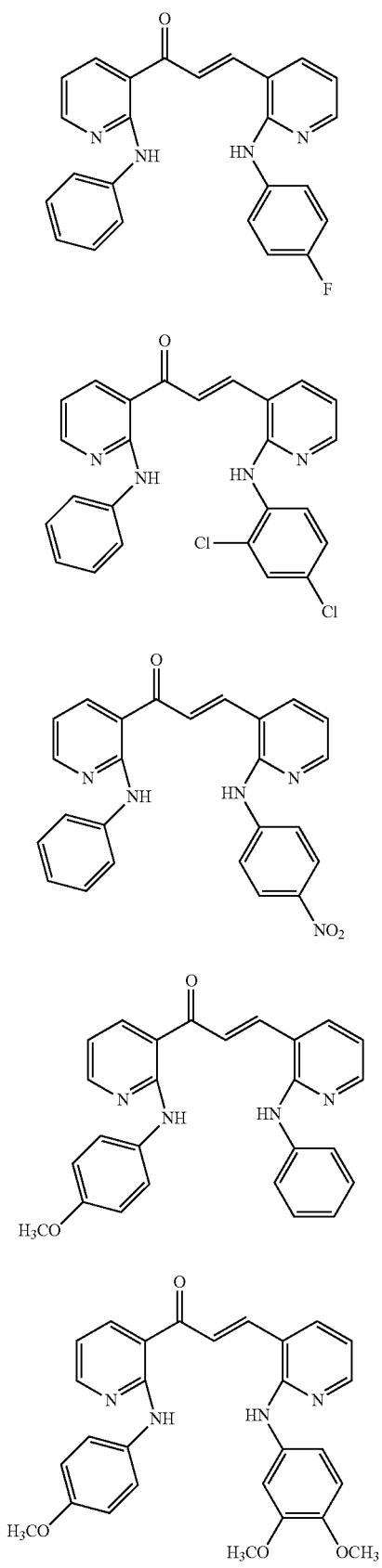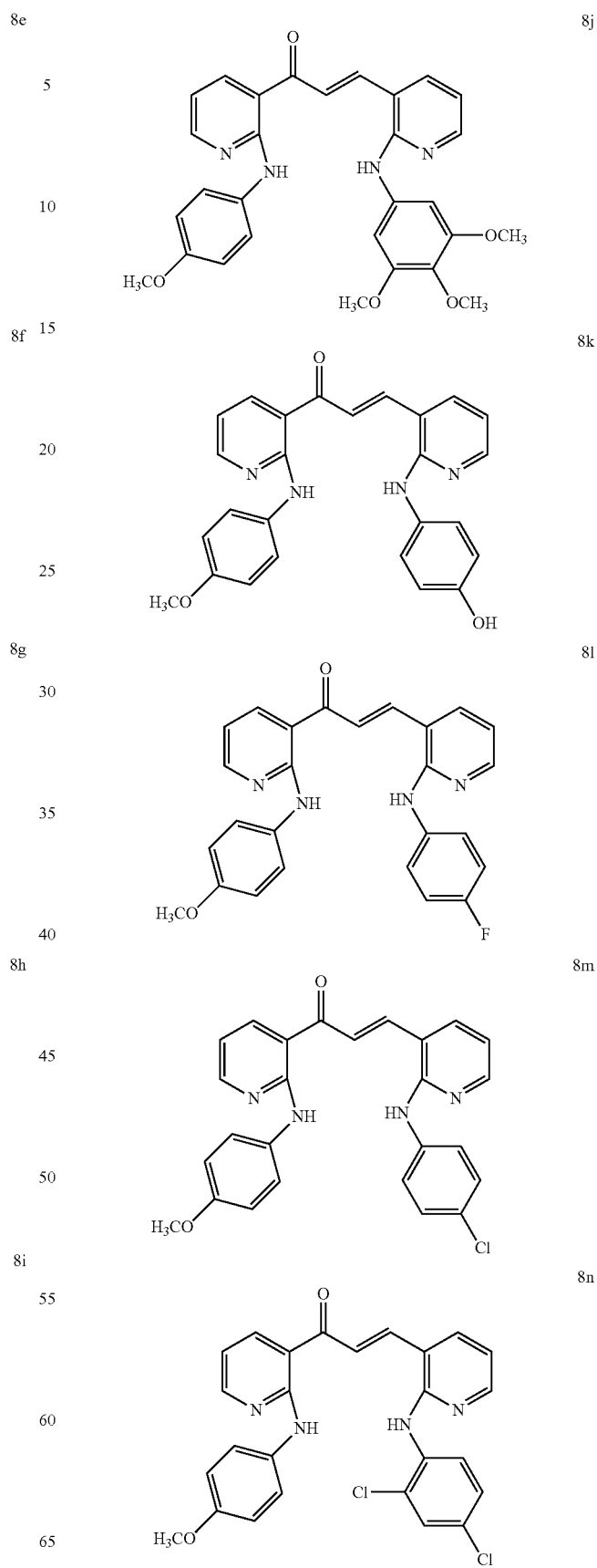

8o
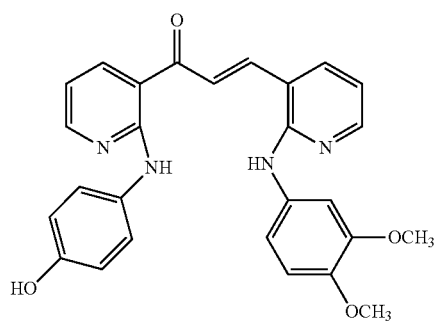
10p
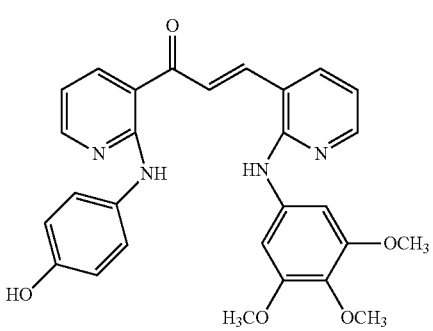
10q
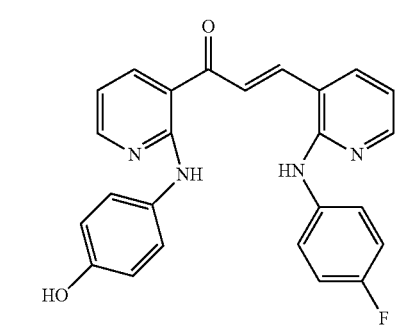
10r
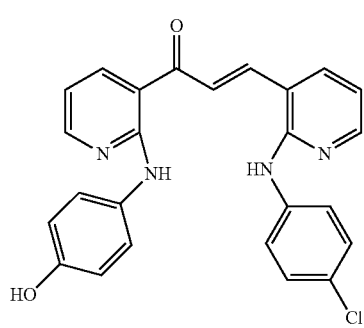
8s
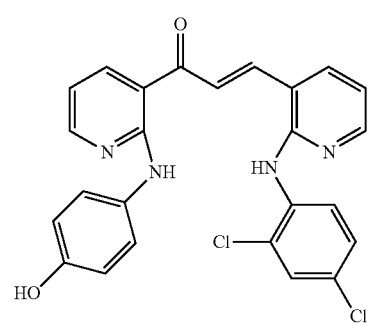
8t
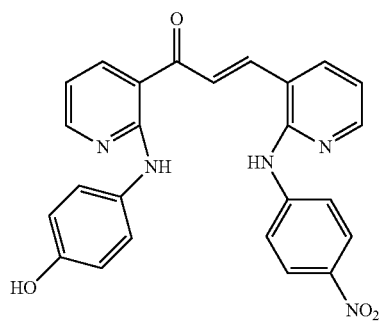
8u
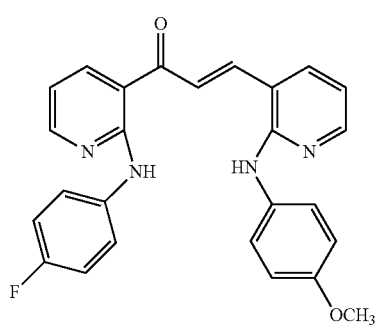
8v
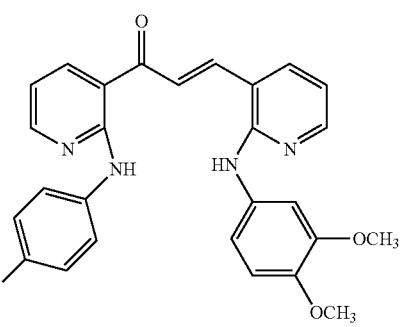
8w
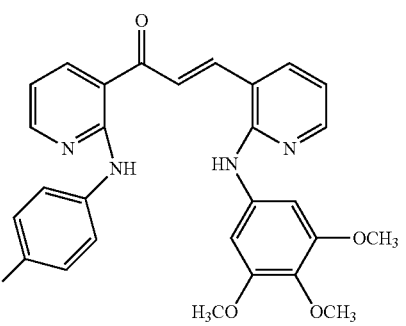
8x
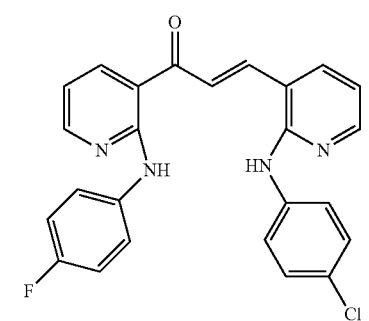

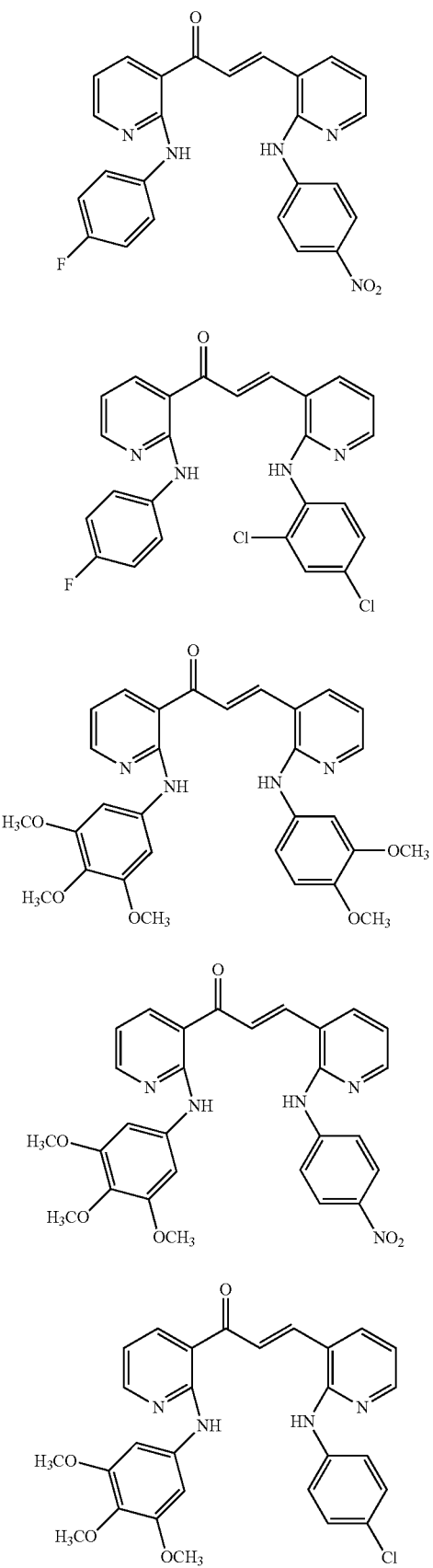

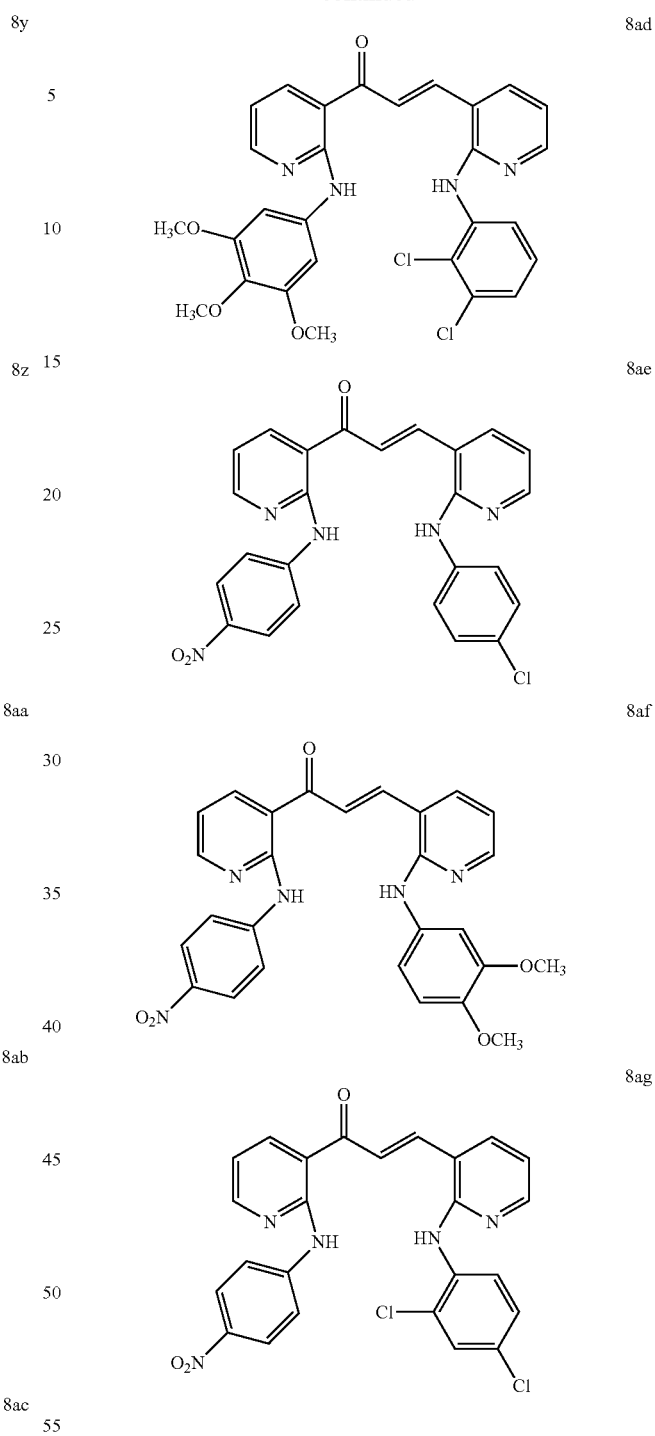

In still another embodiment of the invention wherein the compounds exhibited significant cytotoxic activity against different human tumor cell lines.

In a further embodiment of the invention wherein the $GI_{50}$ of the compounds is ranging between 0.09 μM to 21.1 μM.

Accordingly, the present invention provides a process for preparation of 2-anilinonicotinyl based chalcones of general formula A Formula A

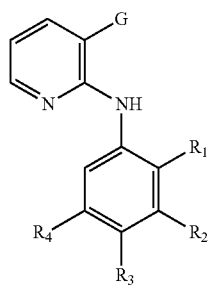

R₁, R₂, R₃, R₄ = H
R₁, R₂, R₄ = H R₃ = NO2
R₁, R₂, R₄ = H R3 = OMe
R₁, R₂, R₄ = H R₃ = F
R₁, R₂, R₄ = H R₃ = Cl
R₁, R₂, R₄ = H R₃ = OH
R₁, R₂ = H, R₄ = H R₃ = OMe
R₁, R₂ = H, R₄, R₃ = H
R₁ = H, R₂, R₃ = H R₄ = OMe   and G =

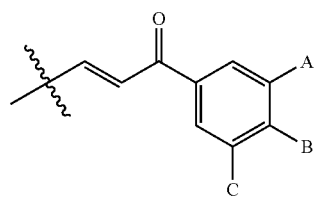

A, B, C = OMe
A,B = OMe, C = H
A= NH2, B = OMe, C=H
A = NO2, B = OMe, C = H
A, C = H, B = OME
A, C = H, B = NH₂
A, C = H, B = Cl or

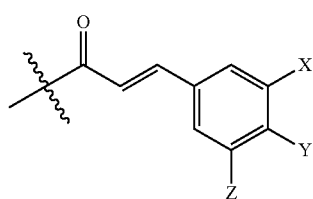

X, Y = OMe, Z = H
X, Y, Z = OME
X = H, Y = OMe, Z = OH
X = H, Y= OMe, Z = NO₂
X = H, Y = OMe, Z= NH₂

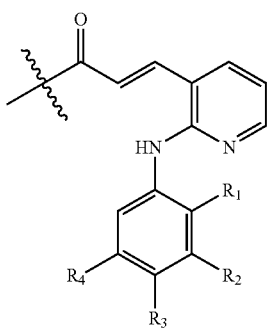

R₁, R₂, R₃, R₄ = H
R₁, R₂, R₄ = H R₃ = NO2
R₁, R₂, R₄ = H R3 = OMe
R₁, R₂, R₄ = H R₃ = F
R₁, R₂, R₄ = H R₃ = Cl
R₁, R₂, R₄ = H R₃ = OH
R₁, R₂ = H, R₄ = H R₃ = OMe
R₁, R₃, = Cl, R₄, R₃ = H
R₁ = H, R₂, R₃ = H R₄ = OMe and the said process comprising the steps;

i) reacting a compound of general formula 16a-i with substituted acetophenone of general formula 18a-g or a compound of general formula 17a-i with substituted aldehyde of general formula 19a-e or a compound of general formula 16a-i and 17a-i 16a-i

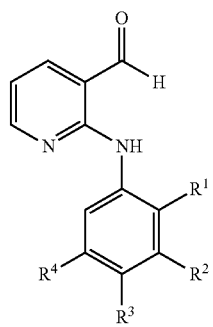

17a-i

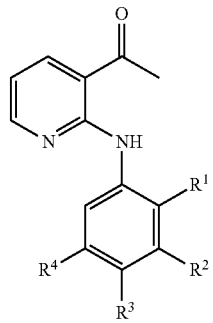

R₁, R₂, R₃, R₄ = H
R₁, R₂, R₄ = H R₃ = NO2
R₁, R₂, R₄ = H R3 = OMe
R₁, R₂, R₄ = H R₃ = F
R₁, R₂, R₄ = H R₃ = Cl
R₁, R₂, R₄ = H R₃ = OH
R₁, R₂ = H R₄ = H R₃ = OMe
R₁, R₂ = Cl, R₄, R₃ = H
R₁ = H, R₂, R₃ = H R₄ = OMe

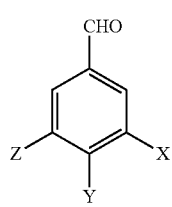

X, Y = OMe, Z = H
X, Y, Z = OME
X = H, Y = OMe, Z = OH
X = H, Y= OMe, Z = NO$_2$
X = H, Y = OMe, Z= NH$_2$ 18a-e

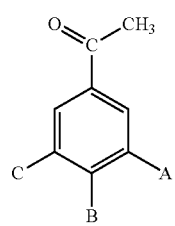

A, B, C = OMe
A,B = OMe, C = H
A= NH2, B = OMe, C=H
A = NO2, B = OMe, C = H
A, C = H, B = OME
A, C = H, B = NH$_2$
A, C = H, B = Cl in an ethanol solvent in the presence of barium hydroxide at a temperature ranging between 20-40° C. for a period of about 6 h, followed by the removal of organic solvent and neutralization by in organic acid (HCl), extracting the reaction mixture with organic solvent selected form ethyl acetate or dichloromethane and evaporating the organic solvent to obtain the resultant crude product and purifying it by chromatographic method to obtain the desired compounds of formulae 6a-6bk, 7a-as and 8a-ag respectively.

In an embodiment of the invention wherein the alcoholic solvent used is methanol or ethanol

DETAILED DESCRIPTION OF THE INVENTION

The precursor substituted anilines (13a-i), substituted acetophenones (18a-i) and substituted aldehydes (19a-e) are commercially available and the chalcones of formulae 6a-bk, 7a-as and 8a-ag have been prepared as illustrated in the Schemes.
i) The ethyl 2-chloro nicotinate (12) was refluxed with substituted anilines (13a-i) in ethylene glycol at 150° C. for 6 h.
ii) Synthesis of weinreb amide (15): A flame dried flask (2 neck 100ml) fitted with one addition funnel and a N$_2$ inlet tube was charged with N, 0 dimethyl hydroxyamine.HCl in CH$_2$Cl$_2$ and reaction mixture was stirred at −5° C. A solution of Me$_3$Al in toluene was added drop-wise over 30 min to the N, O dimethyl hydroxyamine HCl solution. To this solution was added the 2-chloro nicotinic acid methyl ester as a solution in CH$_2$Cl$_2$ over 10 min. After stirring for 6 h, at room temperature gives weinreb amide (15).

iii) Controlled reduction of weinreb amide (15) with DIBAL-H at −78° C. yields crystalline aldehydes (16).

iv) To a stirred solution of methyl magnesium bromide in THF was added weinreb amide (15) in THF over 15 min provided ketone (17).

Dimer type hybrids (8a-ag) are prepared by reacting the aldehydes (16a-i) and acetophenones (17a-i).

All the 2-anilinonicotinyl based chalcone compounds have been synthesized and were purified by column chromatography using different solvents like ethyl acetate, hexane, chloroform and methanol have been performed.

Procedure of chalcone formation:

To the corresponding acetophenones (1 equivalent) in EtOH (3m1) 2N Ba(OH)$_2$ was added and stirred for 5-10 mins, followed by addition of corresponding aldehydes (1 equivalent) and reaction mixture was stirred at room temperature for 8 hrs. After completion of reaction neutralize with HCl and extracted with ethyl acetate, and which were purified by the column chromatography by ethyl acetate/petroleum ether.

These new 2-anilinonicotinyl based chalcone have shown promising anticancer activity in various cancer cell lines. The molecules synthesized are of immense biological significance.

Scheme-1

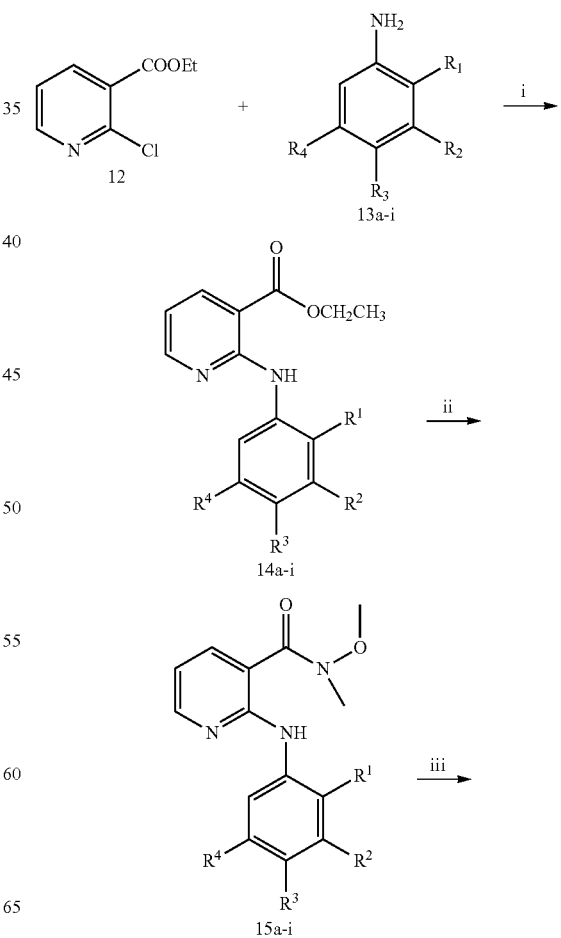

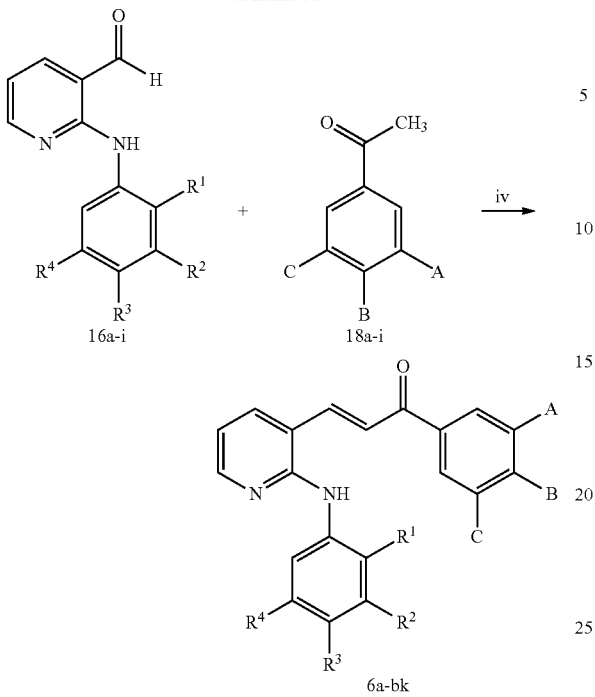

Reagents and conditions: i) ethylene glycol, 150 o C, 6 hrs; ii) N,O dimethyl hydroxylamine.hydrochloride, Me3Al, DCM, 0 oC, rt; iii) DIBAL-H, −78 o C 30 min; iv) aq. Ba(OH)2, methanol, rt, 6 hrs;

Scheme-2

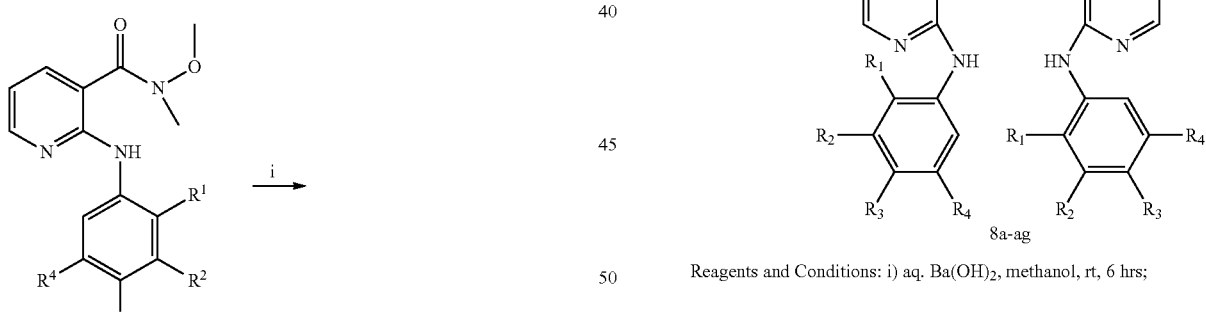

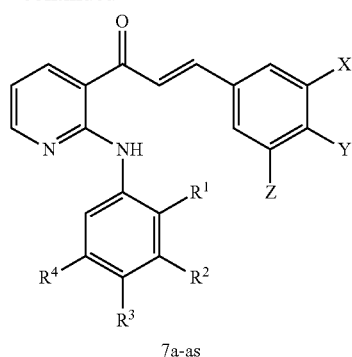

Reagents and Conditions: i) MeMgBr, THF, 1.5 hrs, 0° C.-30° C. ii) aq. Ba(OH)$_2$, methanol, rt, 6 hrs;

Scheme-3

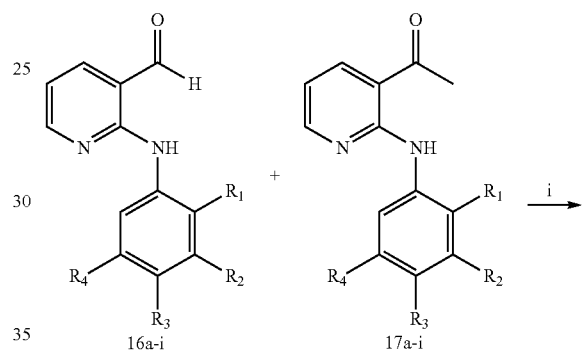

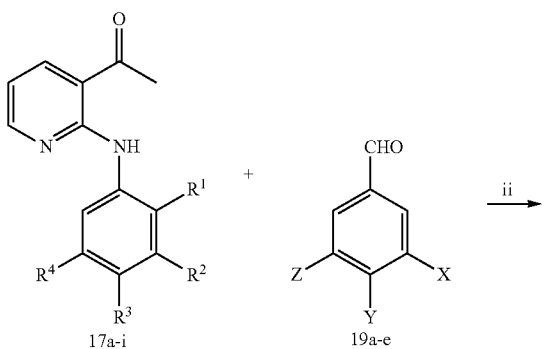

Reagents and Conditions: i) aq. Ba(OH)$_2$, methanol, rt, 6 hrs;

The present invention further provides a process for preparation of novel 2-anilinonicotinyl based chalcone of formula 6a-bk, 7a-as and 8a-ag, which comprises reactions of precursor 2-chloro nicotinic ester 12 as starting material with different anilines (13a-h), followed by the weinreb amide (15a-h) and converted to aldehydes (16a-h) and ketones (17a-h) followed by the reaction with 18a-e and 19a-g in organic solvent (dichloromethane, chloroform, tetrahydrofuran and N,N-dimethylformamide) in different reaction conditions resulted in the formation of final compounds 6a-bk, 7a-as and 8a-ag.

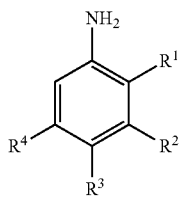

13a: $R_1, R_2, R_3, R_4 = H$
13b: $R_1, R_2, R_4 = H\ R_3 = NO_2$
13c: $R_1, R_2, R_4 = H\ R_3 = OMe$
13d: $R_1, R_2, R_4 = H\ R_3 = F$
13e: $R_1, R_2, R_4 = H\ R_3 = Cl$
13f: $R_1, R_2, R_4 = H\ R_3 = OH$
13g: $R_1, R_2 = H\ R_4 = H\ R_3 = OMe$
13h: $R_1, R_2 = Cl, R_4, R_3 = H$
13i: $R_1 = H, R_2, R_3 = H\ R_4 = OMe$

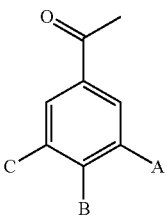

18a: A, B, C = OMe
18b: A,B = OMe, C = H
18c: A= NH2, B = OMe, C=H
18d: A = NO2, B = OMe, C = H
18e: A, C = H, B = OME
18f: A, C = H, B = NH$_2$
18g: A, C = H, B = Cl

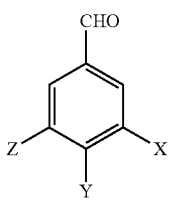

19a: X, Y = OMe, Z = H
19b: X, Y, Z = OME
19c: X = H, Y = OMe, Z = OH
19d: X = H, Y= OMe, Z = NO$_2$
19e: X = H, Y = OMe, Z= NH$_2$ 13a-h 18a-g 19a-e

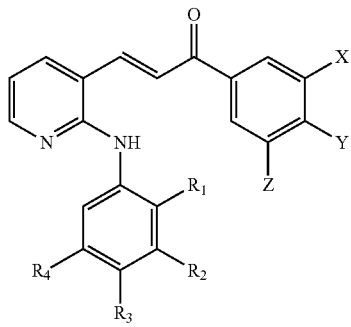

6a-bk

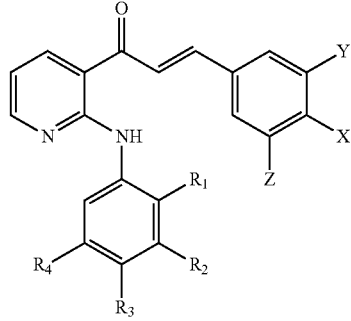

7a-as

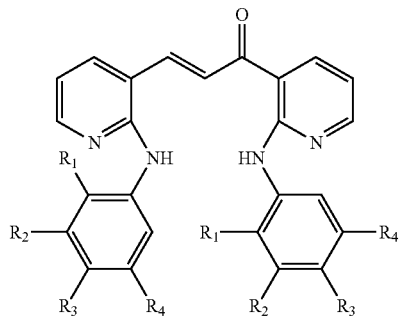

8a-ag

The following examples are given by way of illustration and therefore should not be construed to the present limit of the scope of invention.

EXAMPLE 1

E)-3-(2-(Phenylamino)pyridin-3-yl)-1-(3,4,5-tri-methoxyphenyl)prop-2-en-1-one (6a)

To a stirred solution of 3,4,5-trimethoxyacetophenone (213 mg, 1.01 mmol) in methanol (5 mL) was added 2N Ba(OH)$_2$ solution (2 mL) after 5 minutes to the reaction mixture 2-(phenylamino)nicotinaldehyde (200 mg, 1.01 mmol) was added, stirred for 6 h at 30° C. The progress of the reaction was monitored by TLC for completion. After completion of the reaction, the reaction mixture was acidified with 2N HCl, the resulting precipitate was filtered, washed thoroughly with water and dried over anhydrous CaCl$_2$. The resulting product was purified by by recrystallization from ethanol to afford compound 6a as a pale yellow solid (365 mg, 92% yield).; mp 125-128° C. $^1$H NMR (CDCl$_3$): δ 8.26 (d, 1H, J=4.1 Hz), 8.01 (d, 2H, J=8.3 Hz), 7.95 (d, 1H, J=15.8 Hz), 7.81 (d, 1H, J=8.3 Hz), 7.55 (d, 1H, J=16.1 Hz), 7.48 (q, 2H), 7.01-7.09 (m, 3H), 6.83 (q, 1H), 6.62 (s, 1H), 3.91 (s, 3H) 3.84 (s, 6H); ESI MS: 391 (M+1)$^+$.

EXAMPLE 2

E)-1-(3,4-Dimethoxyphenyl)-3-(2-(phenylamino)pyridin-3-yl)prop-2-en-1-one (6b)

To a solution of 3,4-dimethoxyacetophenone (182 mg, 1.01 mmol) in methanol (5 mL) was added 2N Ba(OH)$_2$ solution (2 mL) and stirred for 5 minutes. Then added 2-(phenylamino)nicotinaldehyde (200 mg, 1.01 mmol) and the reaction mixture was stirred at a temperature of 30° C. for 6h and the reaction was monitored by TLC. After 8h the reaction mixture was acidified with 2N HCl. The resulting precipitate was filtered, washed thoroughly with water and dried over anhydrous CaCl$_2$. The precipitate was recrystallized using ethanol to obtain pure (6b) (328.5 mg, 90% yield).

$^1$H NMR (CDCl$_3$): δ 8.25 (d, 1H, J=4.6 Hz), 8.04 (d, 2H, J=8.1 Hz), 7.92 (d, 1H, J=14.9 Hz), 7.81 (d, 1H, J=8.1 Hz), 7.53 (d, 1H, J=16.1 Hz), 7.46 (q, 2H), 6.98-7.05 (m, 3H), 6.84 (q, 2H), 6.62 (s, 1H), 3.93 (s, 3H) 3.90 (s, 3H); ESI MS: 361 (M+1)$^+$.

EXAMPLE 3

E)-3-(2-(4-Methoxyphenylamino) pyridin-3-yl)-1-(3,4,5-trimethoxyphenyl)prop-2-en-1-one (6h)

To a solution of 3,4,5-trimethoxyacetophenone (184.21 mg, 0.0877 mmol) in methanol (5 mL) was added 2N Ba(OH)$_2$ solution (2 mL) and stirred for 5 minutes. Then added 2-(4-methoxyphenylamino) nicotinaldehyde (200 mg, 0877 mmol) and the reaction mixture was stirred at a temperature of 30° C. for 6h and the reaction was monitored by TLC. After 8h the reaction mixture is acidified with 2N HCl. The resulting precipitate was filtered, washed thoroughly with water and dried over anhydrous CaCl$_2$. The precipitate was recrystallized using ethanol to obtain pure (6h) (340 mg, 92% yield).

$^1$H NMR (CDCl$_3$): δ 8.26 (d, 1H, J=4.1 Hz), 8.05 (d, 2H, J=8.1 Hz), 7.94 (d, 1H, J=15.4 Hz), 7.84 (d, 1H, J=8.3 Hz), 7.54 (d, 1H, J=16.0 Hz), 7.44 (q, 2H), 6.72-6.77 (m, 2H), 6.83 (q, 1H), 6.63 (s, 1H), 3.94 (s, 3H), 3.90 (s, 3H), 3.84 (s, 6H); ESI MS: 421 (M+1)$^+$.

EXAMPLE 4

E)-1-(3,4-Dimethoxyphenyl)-3-(2-(4-methoxyphenylamino)pyridin-3-yl)prop-2-en-1-one (6i)

To a solution of 3,4-dimethoxyacetophenone (78.90 mg, 0.438 mmol) in methanol (5 mL) was added 2N Ba(OH)$_2$ solution (2 mL) and stirred for 5 minutes. Then added 2-(4-methoxyphenylamino) nicotinaldehyde (100 mg, 0.438 mmol) and the reaction mixture was stirred at a temperature of 30° C. for 6h and the reaction was monitored by TLC. After 8h the reaction mixture was acidified with 2N HCl. The resulting precipitate was filtered, washed thoroughly with water and dried over anhydrous CaCl$_2$. The precipitate was recrystallized using ethanol to obtain pure (6i) (150.8 mg, 88% yield).

$^1$H NMR (CDCl$_3$): δ 8.25 (d, 1H, J=4.5 Hz), 8.07 (d, 2H, J=8.1 Hz), 7.93 (d, 1H, J=15.0 Hz), 7.82 (d, 1H, J=7.8 Hz), 7.53 (d, 1H, J=15.1 Hz), 7.50 (q, 2H), 6.97-7.09 (m, 3H), 6.84 (q, 1H), 6.61 (s, 1H), 3.96 (s, 3H), 3.94 (s, 3H), 3.87 (s, 3H); ESI MS: 391 (M+1)$^+$.

EXAMPLE 5

E)-1-(4-Methoxyphenyl)-3-(2-(4-methoxyphenylamino)pyridin-3-yl)prop-2-en-1-one (6l)

To a solution of 4-methoxyacetophenone (65.72 mg, 0.438 mmol) in methanol (5 mL) was added 2N Ba(OH)$_2$ solution (2 ml) and stirred for 5 minutes. Then added 2-(4-methoxyphenylamino)nicotinaldehyde (100 mg, 0.438 mmol) and the reaction mixture was stirred at a temperature of 30° C. for 6h and the reaction was monitored by TLC. After 8h the reaction mixture was acidified with 2N HCl. The resulting precipitate was filtered, washed thoroughly with water and dried over anhydrous CaCl$_2$. The precipitate was recrystallized using ethanol to obtain pure (6l) (145 mg, 92% yield).

$^1$H NMR (CDCl$_3$): δ 8.26 (d, 1H, J=3.9 Hz), 8.02 (d, 2H, J=8.3 Hz), 7.95 (d, 1H, J=15.4 Hz), 7.81 (d, 1H, J=7.8 Hz), 7.56 (d, 1H, J=15.4 Hz), 7.47 (q, 2H), 6.94-7.07 (m, 4H), 6.83 (q, 1H), 6.62 (s, 1H) 3.92 (s, 3H), 3.90 (s, 3H); ESI MS: 361 (M+1)$^+$.

EXAMPLE 6

E)-1-(3,4,5-Trimethoxyphenyl)-3-(2-(3,4,5-trimethoxyphenylamino)pyridin-3-yl)prop-2-en-1-one (6v)

To a solution of 3,4,5-trimethoxyacetophenone (145 mg, 0.693 mmol) in methanol (5 mL) was added 2N Ba(OH)$_2$ solution (2 ml) and stirred for 5 minutes. Then added 2-(3,4,5-trimethoxyphenylamino)nicotinaldehyde (200 mg, 0.693 mmol) and the reaction mixture was stirred at a temperature of 30° C. for 6h and the reaction was monitored by TLC. After 8h the reaction mixture is acidified with 2N HCl. The resulting precipitate was filtered, washed thoroughly with water and dried over anhydrous CaCl$_2$. The precipitate was recrystallized using ethanol to obtain pure (6v) (289 mg, 87% yield).

$^1$H NMR (CDCl$_3$): δ 8.25 (d, 1H, J=4.3 Hz), 7.95 (d, 1H, J=15.7 Hz), 7.85 (d, 1H, J=8.1 Hz), 7.54 (d, 1H, J=15.7 Hz), 7.44 (q, 1H), 6.99-7.07 (m, 3H), 6.84 (q, 1H), 6.62 (s, 1H), 3.95 (s, 6H), 3.91 (s, 9H), 3.89 (s, 3H); ESI MS: 481 (M+1)$^+$.

EXAMPLE 7

E)-1-(3,4-Dimethoxyphenyl)-3-(2-(3,4,5-trimethoxyphenylamino)pyridin-3-yl)prop-2-en-1-one (6w)

To a solution of 3,4-dimethoxyacetophenone (124 mg, 0.692 mmol) in methanol (5 mL) was added 2N Ba(OH)$_2$ solution (2 ml) and stirred for 5 minutes. Then 2-(3,4,5-trimethoxyphenylamino)nicotinaldehyde (200 mg, 0.692 mmol) added and the reaction mixture was stirred at a temperature of 30° C. for 6h and the reaction was monitored by TLC. After 8h then reaction mixture is acidified with 2N HCl. The resulting precipitate was filtered, washed thoroughly with water and dried over anhydrous CaCl$_2$. The precipitate was recrystallized using ethanol to obtain pure (6w) (254.7 mg, 82% yield).

$^1$H NMR (CDCl$_3$): δ 8.26 (d, 1H, J=4.0 Hz), 8.03 (d, 2H, J=8.2 Hz), 7.95 (d, 1H, J=15.2 Hz), 7.84 (d, 1H, J=8.1 Hz), 7.55 (d, 1H, J=16.0 Hz), 7.47 (q, 2H), 7.03-7.14 (m, 2H), 6.83 (q, 1H), 6.63 (s, 1H), 3.90 (s, 6H), 3.88 (s, 6H), 3.85 (s, 3H); ESI MS: 451 (M+1)$^+$.

EXAMPLE 8

E)-1-(4-Methoxyphenyl)-3-(2-(3,4,5-trimethoxyphenylamino)pyridin-3-yl)prop-2-en-1-one (6z)

To a solution of 4-methoxy acetophenone (104.16 mg, 0.694 mmol) in methanol (5 mL) was added 2N Ba(OH)$_2$ solution (2 ml) and stirred for 5 minutes. Then added 2-(3,4,5-trimethoxyphenylamino)nicotinaldehyde (200 mg, 0.694 mmol) and the reaction mixture was stirred at a temperature of 30° C. for 6h and the reaction was monitored by TLC. After 8h the reaction mixture is acidified with 2N HCl. The resulting precipitate was filtered, washed thoroughly with water and dried over anhydrous CaCl$_2$. The precipitate was recrystallized using ethanol to obtain pure (6z) (266 mg, 91% yield).
$^1$H NMR (CDCl$_3$): δ 8.24 (d, 1H, J=4.5 Hz), 8.06 (d, 2H, J=8.2 Hz), 7.97 (d, 1H, J=15.9 Hz), 7.84 (d, 1H, J=8.3 Hz), 7.55 (d, 1H, J=16.1 Hz), 7.44 (q, 2H), 7.11-7.19 (m, 2H), 6.83 (q, 1H), 6.64 (s, 1H), 3.91 (s, 6H) 3.87 (s, 6H); ESI MS: 421 (M+1)$^+$.

EXAMPLE 9

E)-3-(2-(4-Fluorophenylamino)pyridin-3-yl)-1-(3,4,5-trimethoxyphenyl)prop-2-en-1-one (6aj)

To a solution of 3,4,5-trimethoxyacetophenone (194 mg, 0.925 mmol) in methanol (5 mL) was added 2N Ba(OH)$_2$ solution (2 ml) and stirred for 5 minutes followed by the addition of 2-(4-fluorophenylamino)nicotinaldehyde (200 mg, 0.925 mmol) and the reaction mixture was stirred at a temperature of 30° C. for 6h and the reaction was monitored by TLC. After 8h the reaction mixture is acidified with 2N HCl. The resulting precipitate was filtered, washed thoroughly with water and dried over anhydrous CaCl$_2$. The precipitate was recrystallized using ethanol to obtain pure (6aj) (340 mg, 90% yield).
$^1$H NMR (CDCl$_3$): δ 8.26 (dd, 1H, J=4.5, 1.5 Hz), 7.94 (d, 2H, J=15.3 Hz), 7.82 (dd, 1H, J=7.4, 1.1 Hz), 7.44-7.51 (m, 3H), 7.27 (d, 1H, J=5.6 Hz), 7.04 (t, 2H), 6.85 (q, 1H), 6.57 (s, 1H), 3.95 (s, 9H); ESI MS: 409 (M+1)$^+$.

EXAMPLE 10

E)-3-(2-(4-Chlorophenylamino)pyridin-3-yl)-1-(3,4,5-trimethoxyphenyl)prop-2-en-1-one (6ax)

To a solution of 3,4,5-trimethoxyacetophenone (135 mg, 0.06465 mmol) in methanol (5 mL) was added 2N Ba(OH)$_2$ solution (2 mL) and stirred for 5 minutes. Then added 2-(4-chlorophenylamino)nicotinaldehyde (150 mg, 0.06465 mmol) and the reaction mixture was stirred at a temperature of 30° C. for 6h and the reaction was monitored by TLC. After 8h the reaction mixture is acidified with 2N HCl. The resulting precipitate was filtered, washed thoroughly with water and dried over anhydrous CaCl$_2$. The precipitate was recrystallized using ethanol to obtain pure (6ax) (232 mg, 85% yield).
$^1$H NMR (CDCl$_3$): δ 8.26 (dd, 1H, J=4.8, 1.7 Hz), 7.95 (d, 2H, J=15.1 Hz), 7.80 (d, 1H, J=7.2 Hz), 7.42-7.49 (q, 2H), 7.51 (d, 1H, J=15.1 Hz), 7.24 (d, 1H, J=5.1 Hz), 7.04 (t, 2H), 6.84 (q, 1H), 6.59 (s, 1H), 3.98 (s, 9H); ESI MS: 425 (M+1)$^+$.

EXAMPLE 11

E)-1-(2-(Phenylamino)pyridin-3-yl)-3-(3,4,5-trimethoxyphenyl)prop-2-en-1-one (7a)

To a solution of 1-(2-(phenylamino)pyridin-3-yl)ethanone (100 mg, 0.471 mmol) in methanol (5 mL) was added 2N Ba(OH)$_2$ solution (2 ml) and stirred for 5 minutes. Then added 3,4,5-trimethoxybenzaldehyde (92.44 mg, 0.471 mmol) and the reaction mixture was stirred at a temperature of 30° C. for 6h and the reaction was monitored by TLC. After 8h the reaction mixture is acidified with 2N HCl. The resulting precipitate was filtered, washed thoroughly with water and dried over anhydrous CaCl$_2$. The precipitate was recrystallized using ethanol to obtain pure (8a) (169.7 mg, 88% yield).
$^1$H NMR (CDCl$_3$): δ 8.41 (d, 1H, J=4.0 Hz), 7.95 (d, 1H, J=15.3 Hz), 7.83 (d, 2H, J=7.2, Hz), 7.67 (q, 1H), 7.62 (d, 1H, J=15.5 Hz), 7.36 (d, 2H, J=8.2 Hz), 7.02 (t, 2H), 6.86 (d, 1H, J=4.8 Hz), 6.75-6.82 (m, 1H), 6.51 (s, 1H), 3.96 (s, 6H), 3.93 (s, 3H); ESI MS: 409 (M+1)$^+$.

EXAMPLE 12

E)-1-(2-(4-Methoxyphenylamino)pyridin-3-yl)-3-(3,4,5-trimethoxyphenyl)prop-2-en-1-one (7b)

To a solution of 1-(2-(4-methoxyphenylamino)pyridin-3-yl)ethanone (100 mg, 0.412 mmol) in methanol (5 mL) was added 2N Ba(OH)$_2$ solution (2 ml) and stirred for 5 minutes. Then added 3,4,5-trimethoxybenzaldehyde (80.83 mg, 0.412 mmol) and the reaction mixture was stirred at a temperature of 30° C. for 6h and the reaction was monitored by TLC. After 8h the reaction mixture is acidified with 2N HCl. The resulting precipitate was filtered, washed thoroughly with water and dried over anhydrous CaCl$_2$. The precipitate was recrystallized using ethanol to obtain pure (8b) (162 mg, 93% yield).
$^1$H NMR (CDCl$_3$): δ 8.41 (d, 1H, J=4.2 Hz), 7.94 (d, 1H, J=15.0 Hz), 7.82 (d, 2H, J=7.0 Hz), 7.64 (q, 1H), 7.62 (d, 1H, J=15.2 Hz), 7.42 (d, 2H, J=7.8 Hz), 7.1 (t, 2H), 6.84 (d, 1H, J=5.2 Hz), 6.43 (s, 1H), 3.95 (s, 6H), 3.92 (s, 6H); ESI MS: 421 (M+1)$^+$.

EXAMPLE 13

E)-1-(2-(3,4-Dimethoxyphenylamino)pyridin-3-yl)-3-(3,4,5-trimethoxyphenyl) prop-2-en-1-one (7c)

To a solution of 1-(2-(3,4-dimethoxyphenylamino)pyridin-3-yl)ethanone (100 mg, 0.367 mmol) in methanol (5 mL) was added 2N Ba(OH)$_2$ solution (2 ml) and stirred for 5 minutes. Then added 3,4,5-trimethoxybenzaldehyde (71.93 mg, 0.0.367 mmol) and the reaction mixture was stirred at a temperature of 30° C. for 6h and the reaction was monitored by TLC. After 8h the reaction mixture is acidified with 2N HCl. The resulting precipitate was filtered, washed thoroughly with water and dried over anhydrous CaCl$_2$. The precipitate was recrystallized using ethanol to obtain pure (7c) (150 mg, 90% yield).
$^1$H NMR (CDCl$_3$): δ 8.40 (d, 1H, J=4.2 Hz), 7.96 (d, 1H, J=15.9 Hz), 7.84 (d, 2H, J=7.0 Hz), 7.63 (m, 2H), 7.45 (d, 2H, J=8.0 Hz), 7.08 (t, 1H), 6.85 (d, 1H, J=5.2 Hz), 6.44 (s, 1H), 3.98 (s, 6H), 3.96 (s, 6H), 3.92 (s, 6H); ESI MS: 451 (M+1)$^+$.

EXAMPLE 14

E)-1-(2-(4-Fluorophenylamino)pyridin-3-yl)-3-(3,4,5-trimethoxyphenyl)prop-2-en-1-one (7f)

To a solution of 1-(2-(4-fluorophenylamino)pyridin-3-yl)ethanone (100 mg, 0.434 mmol) in methanol (5 mL) was added 2N Ba(OH)$_2$ solution (2 ml) and stirred for 5 minutes. Then added 3,4,5-trimethoxybenzaldehyde (85.30 mg, 0.434 mmol) and the reaction mixture was stirred at a temperature of 30° C. for 8h and the reaction was monitored by TLC. After 6h the reaction mixture is acidified with 2N HCl. The resulting precipitate was filtered, washed thoroughly with water and dried over anhydrous $CaCl_2$. The precipitate was recrystallized using ethanol to obtain pure (7f) (160 mg, 90% yield).

$^1$H NMR ($CDCl_3$): δ 8.41 (d, 1H, J=3.8 Hz), 7.94 (d, 1H, J=15.1 Hz), 7.82 (d, 2H, J=7.4, Hz), 7.68 (q, 1H), 7.60 (d, 1H, J=15.0 Hz), 7.38 (d, 2H, J=8.2 Hz), 7.04 (t, 2H), 6.85 (d, 1H, J=5.0 Hz), 6.51 (s, 1H), 3.95 (s, 9H); ESI MS: 409 (M+1)$^+$.

EXAMPLE 15

E)-1-(2-(3,4-Dichlorophenylamino)pyridin-3-yl)-3-(3,4,5-trimethoxyphenyl) prop-2-en-1-one (7g)

To a solution of 1-(2-(3,4-dichlorophenylamino)pyridin-3-yl)ethanone (100 mg, 0.355 mmol) in methanol (5 mL) was added 2N $Ba(OH)_2$ solution (2 ml) and stirred for 5 minutes. Then added 3,4,5-trimethoxybenzaldehyde (68.67 mg, 0.355 mmol) and the reaction mixture was stirred at a temperature of 30° C. for 6h and the reaction was monitored by TLC. After 8h the reaction mixture is acidified with 2N HCl. The resulting precipitate was filtered, washed thoroughly with water and dried over anhydrous $CaCl_2$. The precipitate was recrystallized using ethanol to obtain pure (7g) (137 mg, 84% yield).

$^1$H NMR ($CDCl_3$): δ 8.40 (d, 1H, J=4.2 Hz), 7.96 (d, 1H, J=15.9 Hz), 7.84 (d, 2H, J=7.0 Hz), 7.66 (q, 1H), 7.62 (d, 1H, J=15.7 Hz), 7.45 (d, 2H, J=8.0 Hz), 7.08 (t, 1H), 6.85 (d, 1H, J=5.2 Hz), 6.44 (s, 1H), 3.98 (s, 6H), 3.96 (s, 6H), 3.92 (s, 6H); ESI MS: 460 (M+1)$^+$.

EXAMPLE 16

E)-1-(2-(4-Chlorophenylamino)pyridin-3-yl)-3-(3,4,5-trimethoxyphenyl)prop-2-en-1-one (7h)

To a solution of 1-(2-(4-chlorophenylamino)pyridin-3-yl)ethanone (100 mg, 0.406 mmol) in methanol (5 mL) was added 2N $Ba(OH)_2$ solution (2 ml) and stirred for 5 minutes. Then added 3,4,5-trimethoxybenzaldehyde (79.65 mg, 0.406 mmol) and the reaction mixture was stirred at a temperature of 30° C. for 6h and the reaction was monitored by TLC. After 8h the reaction mixture is acidified with 2N HCl. The resulting precipitate was filtered, washed thoroughly with water and dried over anhydrous $CaCl_2$. The precipitate was recrystallized using ethanol to obtain pure (7h) (147 mg, 85% yield).

$^1$H NMR ($CDCl_3$): δ 8.43 (d, 1H, J=3.8 Hz), 7.95 (d, 1H, J=15.4 Hz), 7.84 (d, 2H, J=7.6 Hz), 7.67 (q, 1H), 7.64 (d, 1H, J=15.2 Hz), 7.39 (d, 2H, J=8.2 Hz), 7.08 (t, 1H), 6.86 (d, 1H, J=5.0 Hz), 6.48 (s, 1H), 3.96 (s, 6H), 3.92 (s, 3H); ESI MS: 425 (M+1)$^+$.

EXAMPLE 17

E)-3-(2-(4-Fluorophenylamino)pyridin-3-yl)-1-(2-(4-methoxyphenylamino)pyridin-3-yl)prop-2-en-1-one (8l)

To a solution of 1-(2-(4-methoxyphenylamino)pyridin-3-yl)ethanone (100 mg, 0.462 mmol) in methanol (5 mL) was added 2N $Ba(OH)_2$ solution (2 ml) and stirred for 5 minutes. Then added 2-(4-fluorobenzyl)nicotinaldehyde (112.03 mg, 0.462 mmol) and the reaction mixture was stirred at a temperature of 30° C. for 6h and the reaction was monitored by TLC. After 8h the reaction mixture is acidified with 2N HCl. The resulting precipitate was filtered, washed thoroughly with water and dried over anhydrous $CaCl_2$. The precipitate was recrystallized using ethanol to obtain pure (8l) (164 mg, 90% yield).

$^1$H NMR ($CDCl_3$): δ 8.40 (d, 1H, J=3.0 Hz), 8.25 (d, 1H, J=4.0 Hz), 8.21 (d, 1H, J=7.0 Hz), 7.94 (d, 1H, J=15.0 Hz), 7.80 (d, 1H, J=7.0 Hz) 7.68 (q, 2H), 7.60 (d, 1H, J=15.0 Hz), 7.38 (d, 2H, J=9.0 Hz), 7.26 (s, 1H), 7.06 (t, 2H), 6.91 (d, 1H, J=8.0 Hz), 6.76-6.82 (m, 2H), 6.48 (s, 1H), 3.81 (s, 3H); ESI MS: 441 (M+1)$^+$.

EXAMPLE 18

E)-3-(2-(4-Fluorophenylamino)pyridin-3-yl)-1-(2-(3,4,5-trimethoxyphenylamino)pyridin-3-yl)prop-2-en-1-one (8w)

To a solution of 1-(2-(3,4,5-trimethoxyphenylamino)pyridin-3-yl)ethanone (150 mg, 0.694 mmol) in methanol (5 mL) was added 2N $Ba(OH)_2$ solution (2 ml) and stirred for 5 minutes. Then added 2-(4-fluorobenzyl)nicotinaldehyde (209 mg, 0.694 mmol) and the reaction mixture was stirred at a temperature of 30° C. for 6h and the reaction was monitored by TLC. After 8h the reaction mixture is acidified with 2N HCl. The resulting precipitate was filtered, washed thoroughly with water and dried over anhydrous $CaCl_2$. The precipitate was recrystallized using ethanol to obtain pure (6k) (199 mg, 80% yield).

$^1$H NMR ($CDCl_3$): δ 8.40 (d, 1H, J=3.0 Hz), 8.26 (d, 1H, J=4.2 Hz), 8.23 (d, 1H, J=7.2 Hz), 7.95 (d, 1H, J=15.5 Hz), 7.80 (d, 1H, J=7.1 Hz) 7.69 (q, 2H), 7.64 (d, 1H, J=15.4 Hz), 7.27 (s, 1H), 7.06 (t, 2H), 6.93 (d, 1H, J=8.2 Hz), 6.76-6.82 (m, 2H), 6.46 (s, 1H), 3.86 (s, 9H); ESI MS: 501 (M+1)$^+$.

EXAMPLE 19

E)-1-(2-(4-Chlorophenylamino)pyridin-3-yl)-3-(2-(4-fluorophenylamino)pyridin-3-yl)prop-2-en-1-one (8x)

To a solution of 1-(2-(4-chlorophenylamino)pyridin-3-yl)ethanone (200 mg, 0.925 mmol) in methanol (5 mL) was added 2N $Ba(OH)_2$ solution (2 ml) and stirred for 5 minutes. Then added 2-(4-fluorobenzyl)nicotinaldehyde (227.77 mg, 0.925 mmol) and the reaction mixture was stirred at a temperature of 30° C. for 6h and the reaction was monitored by TLC. After 8h the reaction mixture is acidified with 2N HCl. The resulting precipitate was filtered, washed thoroughly with water and dried over anhydrous $CaCl_2$. The precipitate was recrystallized using ethanol to obtain pure (6k) (311 mg, 86% yield).

$^1$H NMR ($CDCl_3$): δ 8.40 (d, 1H, J=3.1 Hz), 8.27 (d, 1H, J=4.2 Hz), 8.24 (d, 1H, J=7.0 Hz), 7.94 (d, 1H, J=15.2 Hz), 7.82 (d, 1H, J=7.0 Hz) 7.68 (q, 2H), 7.63 (d, 1H, J=15.2 Hz), 7.36 (d, 2H, J=9.0 Hz), 7.25 (s, 1H), 7.1 (t, 2H), 6.88 (d, 1H, J=8.0 Hz), 6.80 (d, 1H, J=7.1 Hz), 6.45 (s, 1H); ESI MS: 445 (M+1)$^+$.

EXAMPLE 20

E)-3-(2-(4-Fluorophenylamino)pyridin-3-yl)-1-(2-(4-nitrophenylamino)phenyl)prop-2-en-1-one (8y)

To a solution of 1-(2-(4-fluorophenylamino)pyridin-3-yl)ethanone (200 mg, 0.925 mmol) in methanol (5 mL) was added 2N $Ba(OH)_2$ solution (2 ml) and stirred for 5 minutes.

Then added 2-(4-fluorobenzyl)nicotinaldehyde (213.17 mg, 0.925 mmol) and the reaction mixture was stirred at a temperature of 30° C. for 6h and the reaction was monitored by TLC. After 8h the reaction mixture is acidified with 2N HCl. The resulting precipitate was filtered, washed thoroughly with water and dried over anhydrous $CaCl_2$. The precipitate was recrystallized using ethanol to obtain pure (6k) (339 mg, 91% yield).

$^1$H NMR ($CDCl_3$): δ 8.42 (d, 1H, J=3.2 Hz), 8.26 (d, 1H, J=4.1 Hz), 8.21 (d, 1H, J=7.1 Hz), 7.96 (d, 1H, J=15.9 Hz), 7.80 (d, 1H, J=7.2 Hz) 7.68 (q, 2H), 7.60 (d, 1H, J=15.8 Hz), 7.38 (d, 2H, J=9.0 Hz), 7.26 (s, 1H), 7.06 (t, 2H), 6.91 (d, 1H, J=8.0 Hz), 6.82 (d, 1H, J=7.1 Hz), 6.54 (s, 1H); ESI MS: 455 $(M+1)^+$.

Biological Activity:

The in vitro anticancer activity studies for these chalcone analogues were carried out at the National Cancer Institute, USA.

Anticancer Activity

The chalcone compounds have been tested at NCI, USA, against sixty human tumor cell lines derived from nine cancer types (leukemia, non-small cell lung cancer, colon cancer, CNS cancer, melanoma cancer, ovarian cancer, renal cancer, prostate cancer and breast cancer). For these compounds results are expressed as growth inhibition ($GI_{50}$) values as per NCI protocol. The anticancer activity data of compounds 6a, 6h, 6v, 6z, 6ax and 8f are shown in Table 1.

Method Used for Biological Evaluation

We describe here the development and implementation of a pilot-scale, in vitro, anticancer drug screen utilizing a panel of 60 human tumor cell lines organized into subpanels representing leukemia, melanoma, and cancers of the lung, colon, kidney, ovary, and central nervous system. The ultimate goal of this disease-oriented screen is to facilitate the discovery of new compounds with potential cell line-specific and/or subpanel-specific antitumor activity. In the current screening protocol, each cell line is inoculated onto microtiter plates, then preincubated for 28 hours. Subsequently, test agents are added in five 10-fold dilutions and the culture is incubated for an additional 48 hours. For each test agent, a dose-response profile is generated. End-point determinations of the cell viability or cell growth are performed by in situ fixation of cells, followed by staining with a protein-binding dye, sulforhodamine B (SRB). The SRB binds to the basic amino acids of cellular macromolecules; the solubilized stain is measured spectrophotometrically to determine relative cell growth or viability in treated and untreated cells.

TABLE 1

Cytotoxicity of compounds 6a, 6h, 6v, 6z, 6ax and 8f in sixty cancer cell lines

| Panel/Cell Line | $GI_{50}$ values (μM conc.) | | | | | |
|---|---|---|---|---|---|---|
| | 6a | 6h | 6v | 6z | 6ax | 7f |
| Leukemia | | | | | | |
| CCRF-CEM | 0.32 | 0.50 | 7.08 | 0.71 | 0.37 | 2.45 |
| HL-60(TB) | 1.52 | — | 8.00 | 1.27 | 1.59 | 2.40 |
| K-562 | — | 0.78 | — | — | — | — |
| MOLT-4 | 2.68 | 2.09 | 6.72 | 2.26 | 2.55 | 2.75 |
| RPMI-8226 | 0.35 | 1.08 | 6.83 | 0.85 | 0.65 | 2.43 |
| SR | 0.34 | 0.46 | 3.60 | 0.09 | 0.77 | 1.93 |
| Non-small cell lung | | | | | | |
| A549/ATCC | 1.30 | — | 4.21 | 2.15 | 1.63 | 2.66 |
| EKVX | 1.61 | 1.80 | 7.55 | 10.8 | 1.61 | 3.94 |
| HOP-62 | 0.65 | 1.78 | 12.1 | 2.18 | 1.65 | 2.90 |
| HOP-92 | 0.39 | 1.59 | 0.94 | 2.40 | 0.51 | 1.67 |
| NCI-H226 | 1.23 | 1.37 | 10.8 | 1.73 | 1.16 | 1.79 |
| NCI-H23 | 1.43 | 1.72 | 10.2 | 4.02 | 1.58 | 2.34 |
| NCI-H322M | 1.90 | 2.13 | 21.1 | 7.38 | 1.95 | 4.83 |
| NCI-H460 | 1.80 | 2.01 | 3.61 | 2.16 | 1.92 | 2.83 |
| NCI-H522 | 0.49 | 0.36 | 7.44 | 1.33 | 1.46 | 2.69 |
| Colon | | | | | | |
| COLO-205 | 1.29 | 1.69 | 4.44 | 1.54 | 1.83 | 2.64 |
| HCC-2998 | 1.18 | 1.68 | 7.74 | 1.42 | 1.52 | 1.78 |
| HCT-116 | 0.33 | 1.02 | 3.77 | 0.53 | 0.56 | 1.54 |
| HCT-15 | 0.74 | 1.66 | 5.02 | 0.91 | 1.49 | 2.27 |
| HT29 | 0.51 | 1.60 | 5.51 | 0.37 | 1.43 | 2.75 |
| KM12 | 0.92 | 1.69 | 6.50 | 0.46 | 1.83 | 3.72 |
| SW-620 | 0.42 | 1.20 | 4.81 | 0.39 | 0.95 | 3.30 |
| CNS | | | | | | |
| SF-268 | 1.55 | 1.77 | 8.19 | 3.13 | 1.72 | 4.18 |
| SF-295 | 1.87 | 1.85 | 4.92 | 2.91 | 1.93 | 4.16 |
| SF-539 | 1.65 | 2.04 | 12.2 | 1.81 | 1.71 | 2.85 |
| SNB-19 | 1.48 | 2.14 | 6.80 | 2.87 | 1.52 | 3.73 |
| SNB-75 | 1.13 | 1.15 | 4.12 | 2.44 | 1.63 | 1.93 |
| U251 | 1.12 | 1.27 | 4.10 | 1.27 | 1.25 | 2.78 |
| Melanoma | | | | | | |
| LOX IMVI | 0.49 | 1.23 | 4.51 | 1.12 | 1.27 | 1.69 |
| MALME-3M | 1.92 | 1.40 | 15.3 | 3.24 | 1.91 | 6.90 |
| M14 | 1.50 | 1.65 | 8.99 | 2.55 | 1.75 | 3.19 |
| MDA-MB-435 | 0.63 | 1.46 | 5.63 | 0.74 | 1.49 | 3.05 |
| SK-MEL-2 | 1.66 | 1.47 | 8.00 | 7.04 | 2.01 | 2.52 |
| SK-MEL-28 | 1.58 | 1.37 | 5.43 | 3.72 | 1.72 | 3.22 |
| SK-MEL-5 | 1.34 | 1.39 | 4.17 | 2.41 | 1.50 | 2.51 |
| UACC-257 | 1.51 | 1.53 | 8.52 | 3.63 | 1.50 | 2.90 |
| UACC-62 | 1.29 | 1.56 | 4.96 | 1.90 | 1.54 | 2.35 |
| Ovarian | | | | | | |
| IGROV1 | 2.37 | 2.0 | 12.6 | 4.64 | 2.24 | 7.42 |
| OVCAR-3 | 0.42 | 1.64 | 7.45 | 0.48 | 1.31 | 2.63 |
| OVCAR-4 | 1.45 | 1.62 | 9.78 | 1.78 | 1.51 | 3.81 |
| OVCAR-5 | 1.54 | 1.97 | 16.3 | 1.95 | 1.74 | 4.10 |
| OVCAR-8 | 1.27 | 1.56 | 6.70 | 2.20 | 1.63 | 2.69 |
| NCI/ADR-RES | 1.03 | 2.23 | 4.44 | 1.38 | 1.64 | 2.37 |
| SK-OV-3 | 1.60 | 2.72 | 11.1 | 3.15 | 1.72 | 3.10 |
| Renal | | | | | | |
| 786-0 | 1.29 | 1.69 | 5.98 | 1.31 | 1.46 | 3.90 |
| A498 | 1.42 | 3.19 | 2.64 | 4.28 | 1.40 | 2.18 |
| ACHN | 1.28 | 1.55 | 5.34 | 1.70 | 1.77 | 2.84 |
| CAKI-1 | 1.16 | 1.52 | 4.01 | 2.26 | 1.75 | 3.68 |
| RXF 393 | 1.12 | 1.49 | 5.22 | 1.68 | 1.26 | 2.81 |
| SN12C | 1.21 | 1.56 | 5.10 | 1.91 | 1.46 | 3.23 |
| TK-10 | 1.82 | — | 1.55 | 2.06 | 1.87 | 3.52 |
| UO-31 | 1.19 | 1.12 | 5.09 | 1.44 | 1.32 | 5.62 |
| Prostate | | | | | | |
| PC-3 | 1.10 | 2.82 | 7.81 | 1.13 | 1.44 | 3.95 |
| DU-145 | 0.72 | 1.59 | 6.22 | 2.59 | 1.63 | 3.32 |
| Breast | | | | | | |
| MCF7 | 0.35 | 0.69 | 3.97 | 0.18 | 1.02 | 2.44 |
| MDA-MB-231/ATCC | 1.40 | 1.94 | 12.6 | 2.15 | 1.49 | 3.07 |
| HS 578T | 2.15 | 2.68 | 13.2 | 6.38 | 3.08 | 3.68 |
| BT-549 | 1.26 | 1.58 | 14.3 | 2.41 | 1.50 | 2.70 |
| T-47D | 1.43 | 1.67 | 5.30 | 2.04 | 1.42 | 3.06 |
| MDA-MB-468 | 0.66 | 1.15 | 6.78 | 0.77 | 1.29 | 1.77 |

The newly synthesized compounds 6a, 6h, 6v, 6z, 6ax and 7f are tested against sixty cancer cell lines (leukemia, non-small cell lung cancer, colon cancer, CNS cancer, melanoma cancer, ovarian cancer, renal cancer, prostate cancer and breast cancer). The most active compounds of the series are 6a, 6h and 6z are found to be more potent with GI50 values 0.09 μM against in SR (leukemia cancer cell line), 0.35 μM, 0.69 μM and 0.18 μM which are promising cytotoxic compared to known Chalcones, such as (E)-1-(2,4-dimethoxyphenyl)-3-(2,6-dimethoxyphenyl)prop-2-en-1-one with $IC_{50}$ of 75 μM against breast cancer cell line MCF7 (*J. Med. Chem.* 2008, 51, 2307-2310).

| Compounds | $GI_{50}$ μM in MCF7 |
|---|---|
| 6a | 0.35 |
| 6h | 0.69 |
| 6v | 3.97 |
| 6z | 0.18 |
| 6ax | 1.02 |
| 7f | 2.44 |
| B | 75 |

Significance of the Work Carried Out

The novel 2-anilinonicotinyl based chalcones that have been synthesized exhibited significant cytotoxic activity against different human tumour cell lines.

ADVANTAGES OF THE INVENTION

1. The present invention provides new chalcones useful as antitumour agents.
2. It also provides a process for the preparation of novel chalcones.

The invention claimed is:

1. A 2-anilinonicotinyl based chalcone compound of general formula A

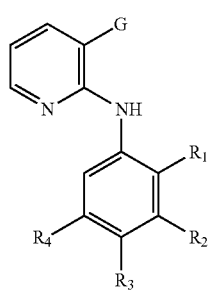

Formula A $R_1, R_2, R_3, R_4 = H$;
$R_1, R_2, R_4 = H, R_3 = NO_2$;
$R_1, R_2, R_4 = H, R_3 = OMe$;
$R_1, R_2, R_4 = H, R_3 = F$;
$R_1, R_2, R_4 = H, R_3 = Cl$;
$R_1, R_2, R_4 = H, R_3 = OH$;
$R_1, R_2 = H, R_4 = H, R_3 = OMe$;
$R_1, R_3 = Cl, R_4, R_2 = H$; or
$R_1 = H, R_2, R_3 = H, R_4 = OMe$;

and G =

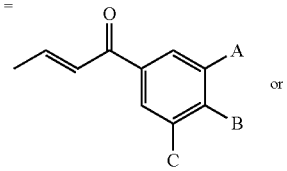

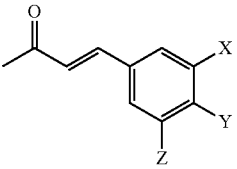

A, B, C = OMe;
A, B = OMe, C = H;
A = NH2, B = OMe, C = H;
A = NO2, B = OMe; C = H;
A, C = H, B = OMe;
A, C = H, B = NH2; or
A, C = H, B = Cl;

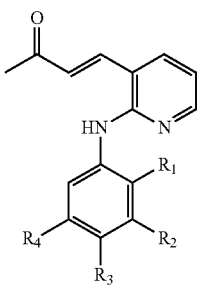

X, Y = OMe, Z = H;
X, Y, Z = OMe;
X = H, Y = OMe, Z = OH;
X = H, Y = OMe, Z = NO2; or
X = H, Y = OMe, Z = NH2;

$R_1, R_2, R_3, R_4 = H$;
$R_1, R_2, R_4 = H, R_3 = NO_2$;
$R_1, R_2, R_4 = H, R_3 = OMe$;
$R_1, R_2, R_4 = H, R_3 = F$;
$R_1, R_2, R_4 = H, R_3 = Cl$;
$R_1, R_2, R_4 = H, R_3 = OH$;
$R_1, R_2 = H, R_4 = H, R_3 = OMe$;
$R_1, R_3 = Cl, R_4, R_2 = H$; or
$R_1 = H, R_2, R_3 = H, R_4 = OMe$.

2. The 2-anilinonicotinyl based chalcone compound according to claim 1 represented by one of the following general formulae 6a-bk, 7a-as, and 8a-ag:

6a-bk 7a-as 8a-ag

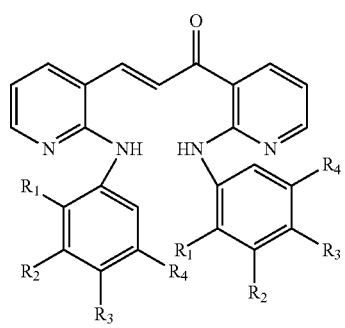

wherein

R₁, R₂, R₃, R₄ = H;
R₁, R₂, R₄ = H, R₃ = NO₂;
R₁, R₂, R₄ = H, R₃ = OMe;
R₁, R₂, R₄ = H, R₃ = F;
R₁, R₂, R₄ = H, R₃ = Cl;
R₁, R₂, R₄ = H, R₃ = OH;
R₁, R₂ = H, R₄ = H, R₃ = OMe;
R₁, R₃ = Cl, R₄, R₂ = H; or
R₁ = H, R₂, R₃ = H, R₄ = OMe;

X, Y = OMe, Z = H;
X, Y, Z = OMe;
X = H, Y = OMe, Z = OH
X = H, Y = OMe, Z = NO₂; or
X = H, Y = OMe, Z = NH₂;

A, B, C = OMe;
A, B = OMe, C = H;
A = NH₂, B = OMe, C = H;
A = NO₂, B = OMe; C = H;
A, C = H, B = OMe;
A, C = H, B = NH₂; or
A, C = H, B = Cl.

3. A 2-anilinonicotinyl based chalcone compound selected from the group consisting of:

6a

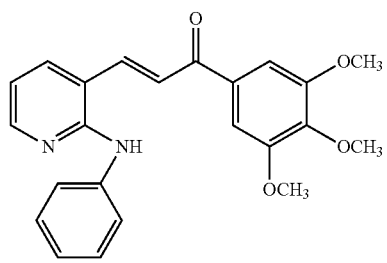

6b

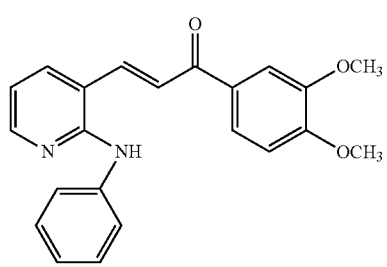

6c

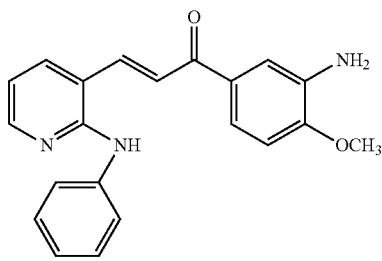

6d

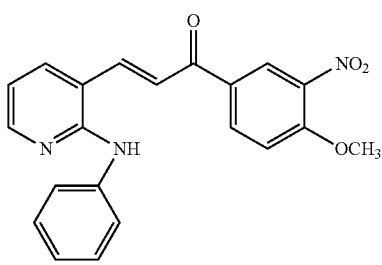

6e

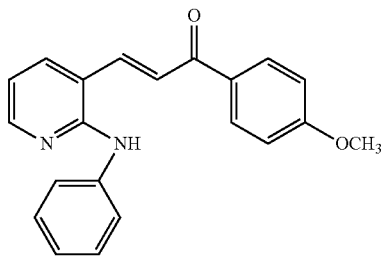

6f

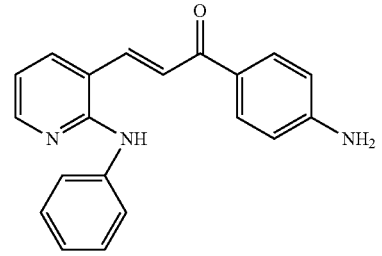

6g

6h

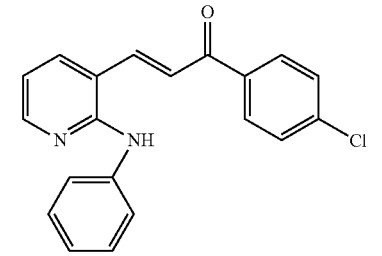

6i 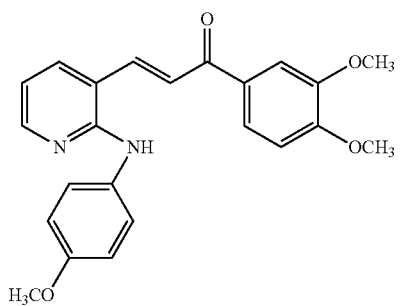
6j 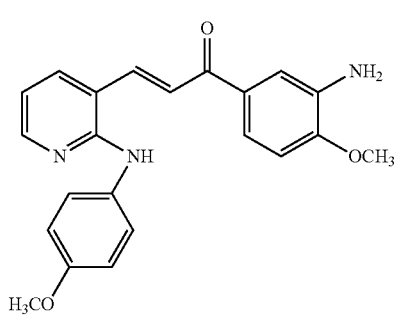
6k 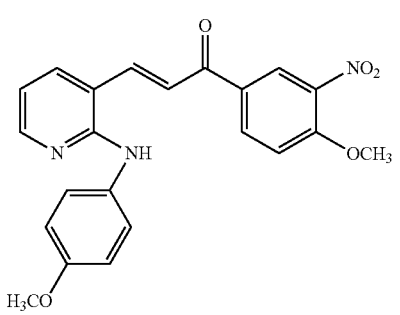
6l 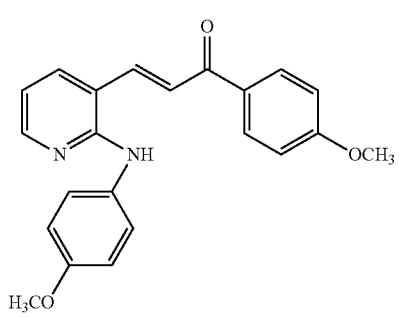
6m 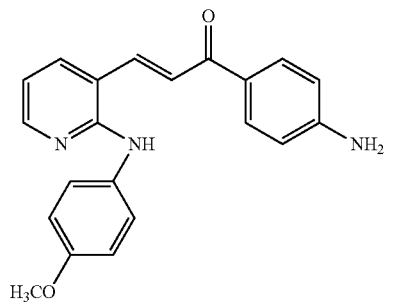
6n 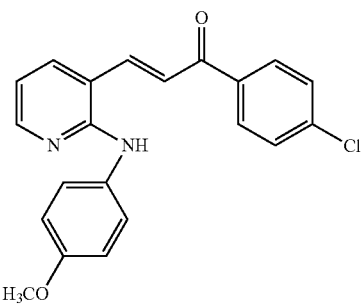
6o 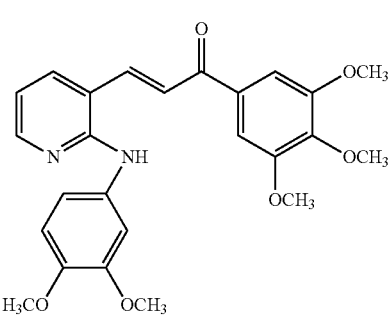
6p 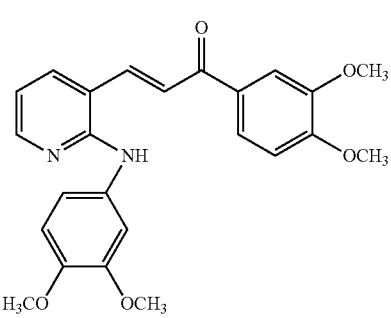
6q 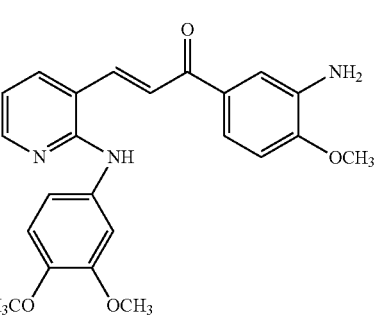
6r 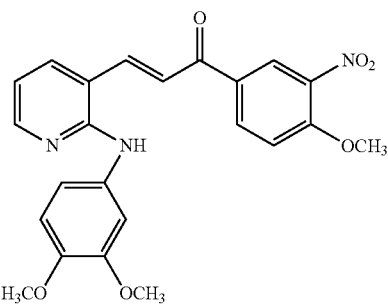

6s 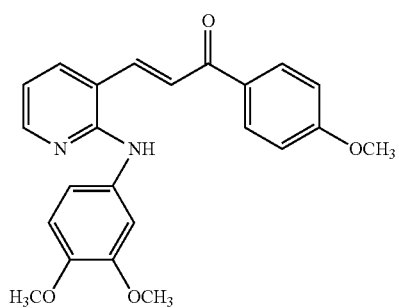
6t 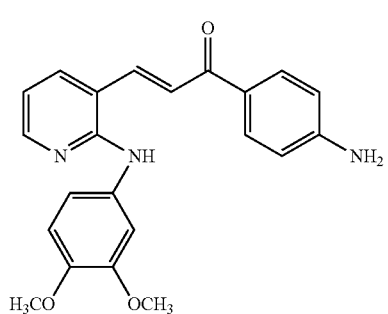
6u 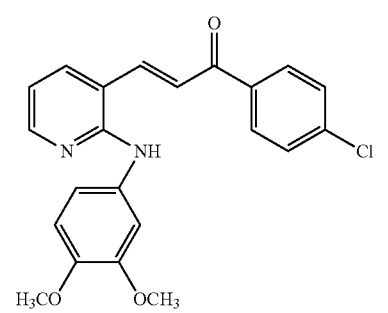
6v 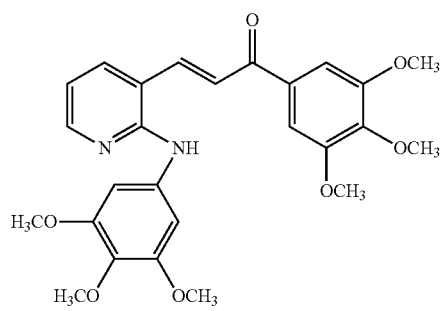
6w 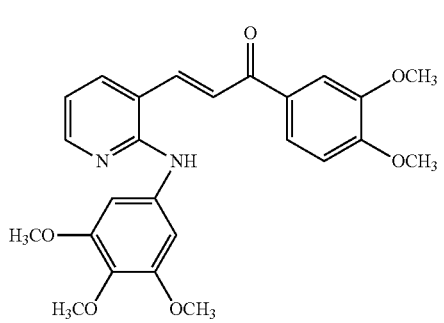
6x 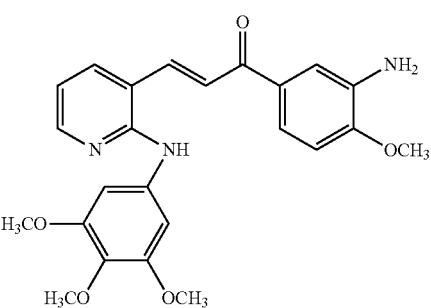
6y 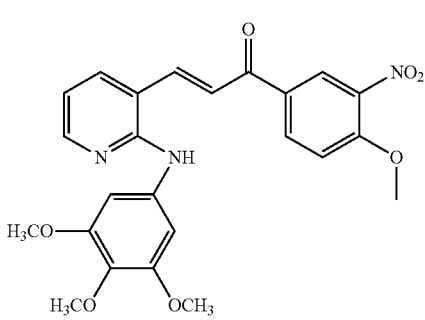
6z 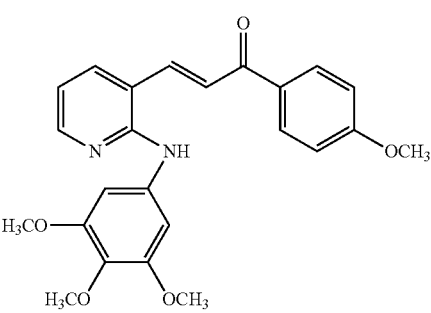
6aa 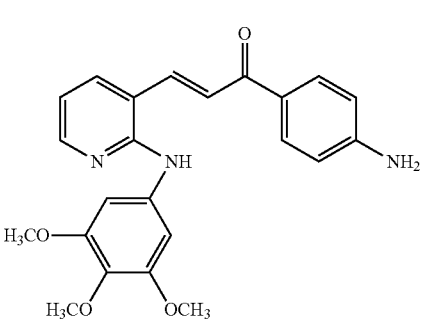
6ab 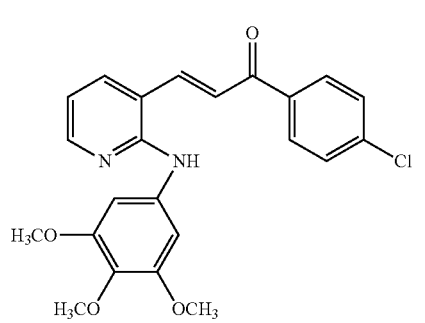

6ac 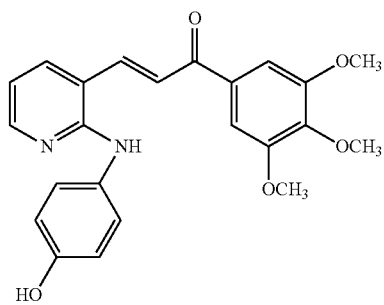
6ad 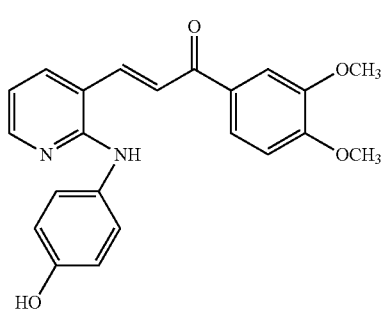
6ae 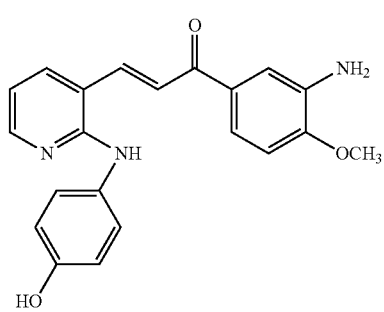
6af 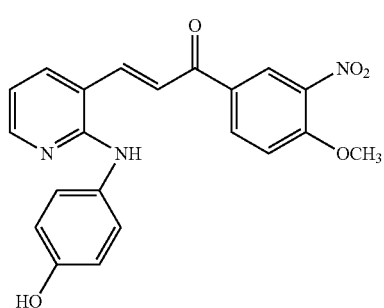
6ag 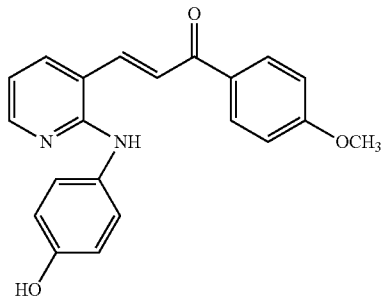
6ah 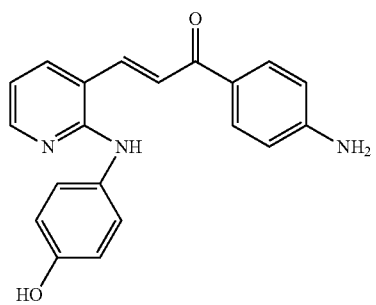
6ai 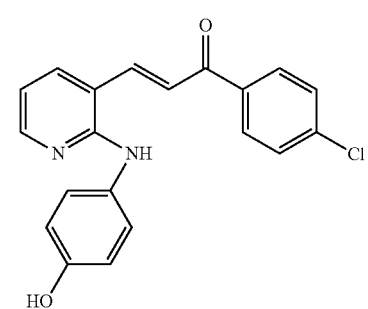
6aj 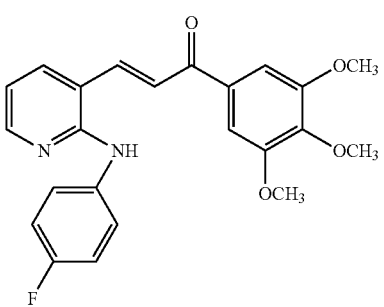
6ak 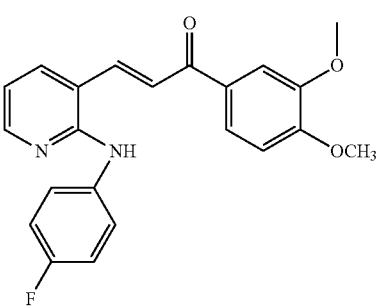
6al 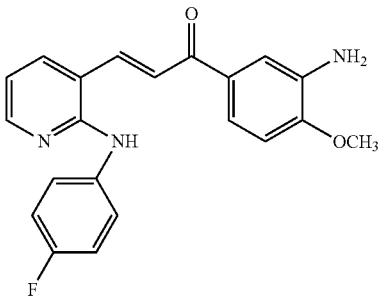

| | |
|---|---|
| 6am 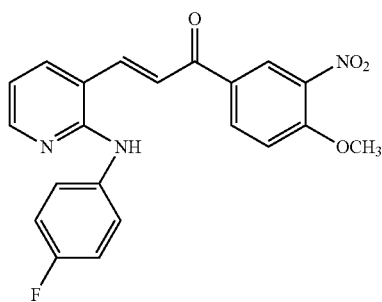 | 6ar 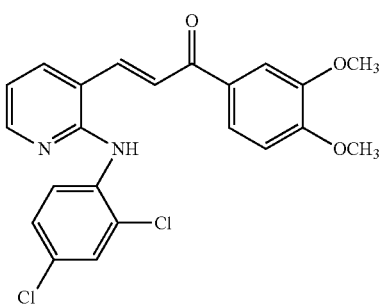 |
| 6an 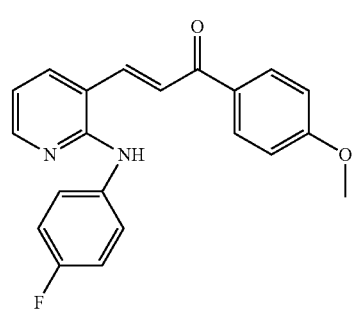 | 6as 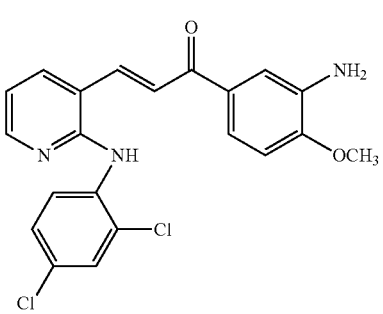 |
| 6ao 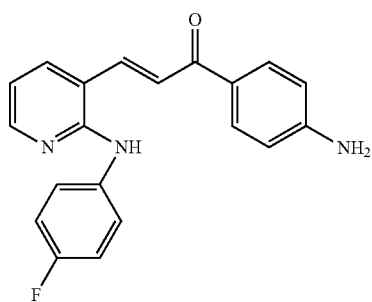 | 6at 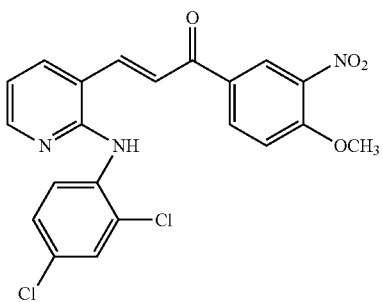 |
| 6ap 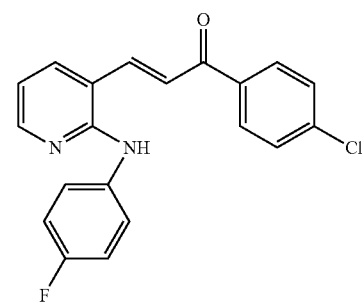 | 6au 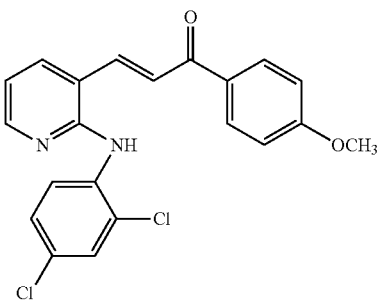 |
| 6aq 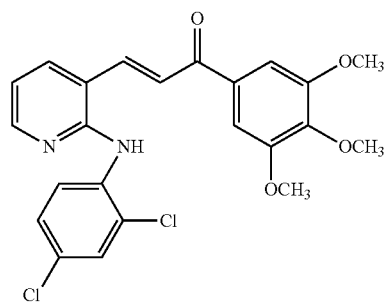 | 6av 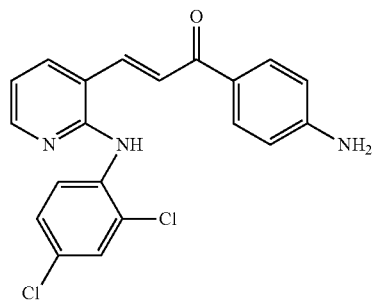 |

6aw 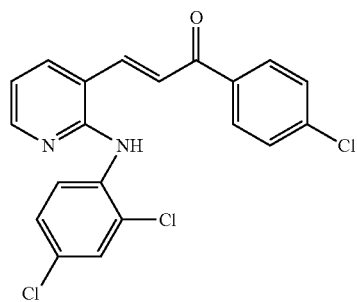
6ax 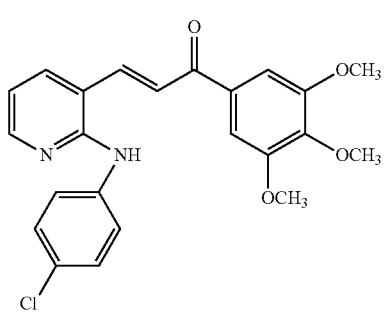
6ay 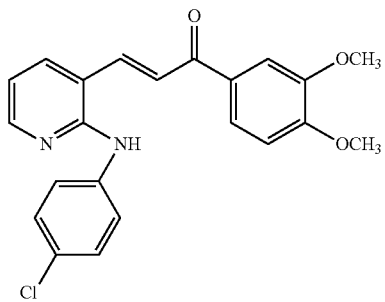
6az 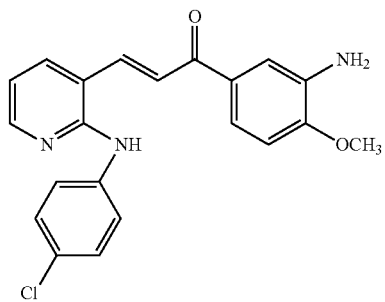
6ba 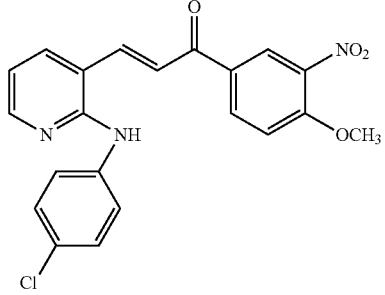
6bb 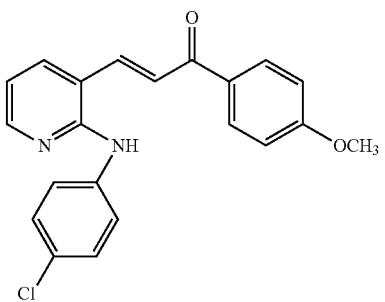
6bc 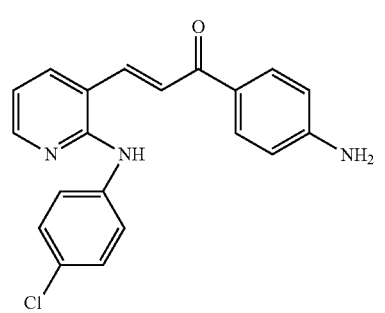
6bd 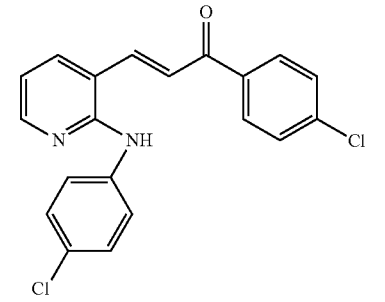
6be 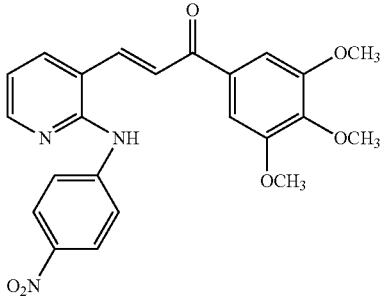
6bf 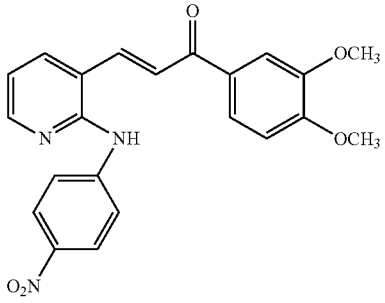

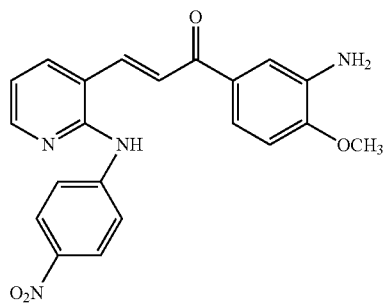 6bg
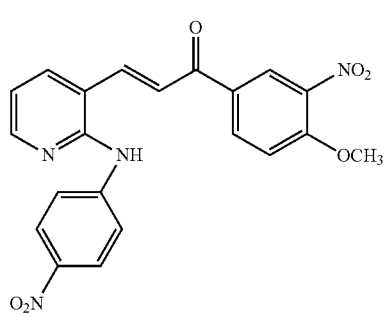 6bh
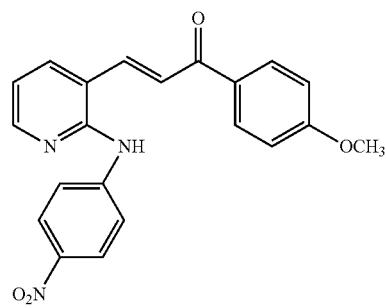 6bi
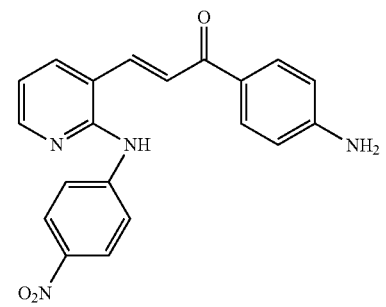 6bj
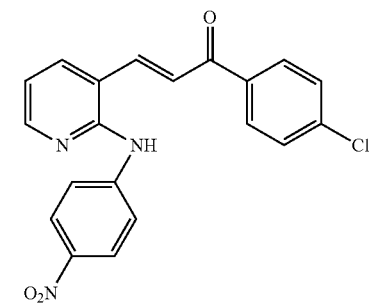 6bk
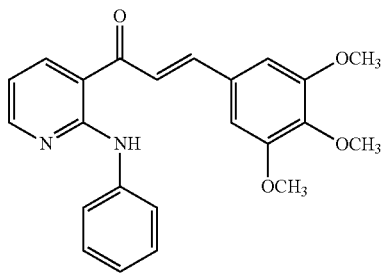 7a
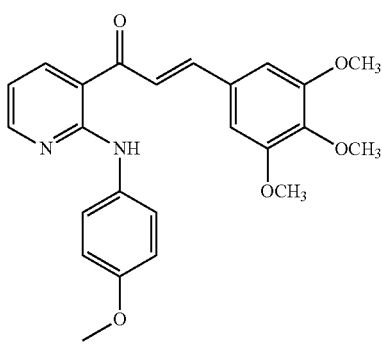 7b
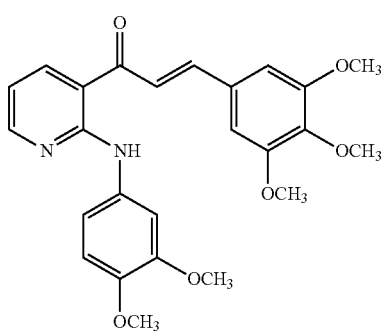 7c
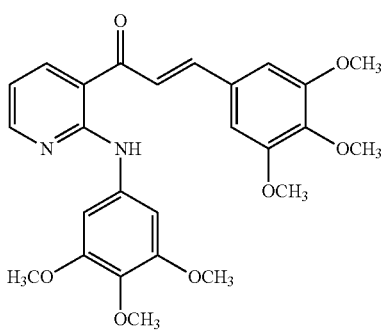 7d
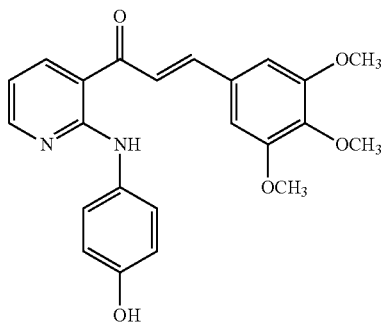 7e

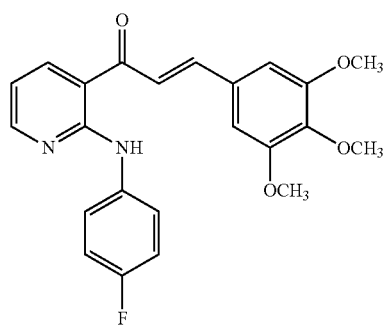 7f
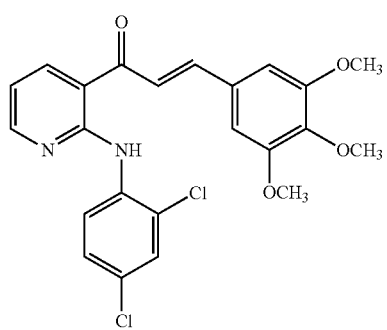 7g
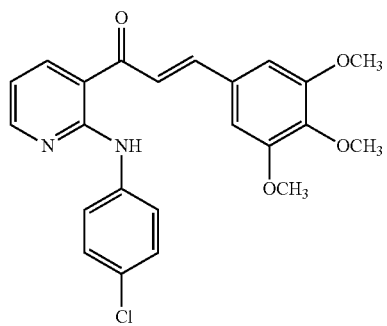 7h
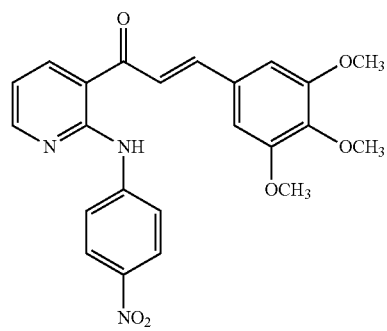 7i
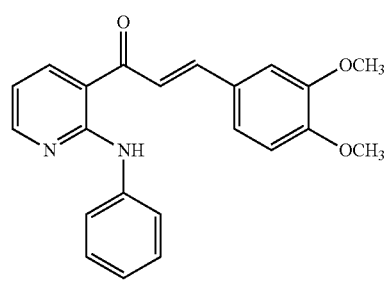 7j
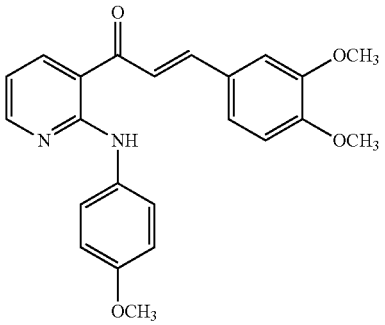 7k
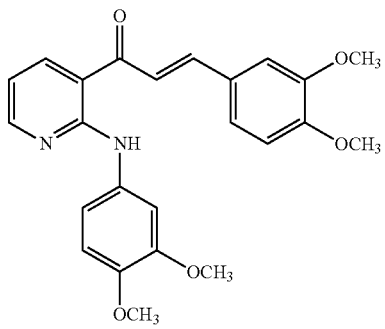 7l
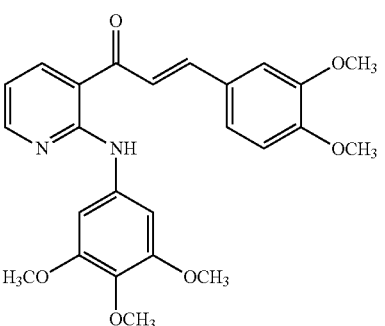 7m
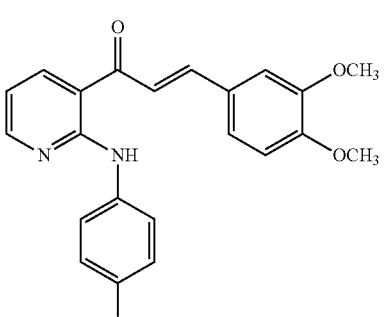 7n
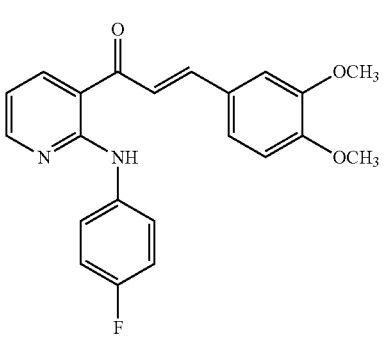 7o -continued
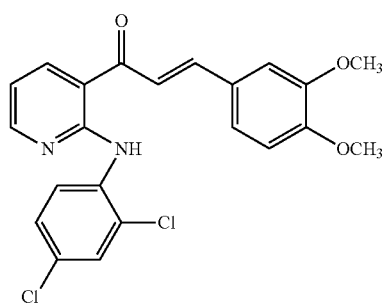 7p
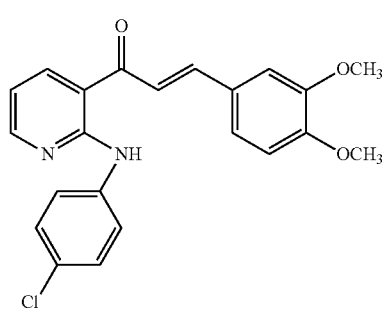 7q
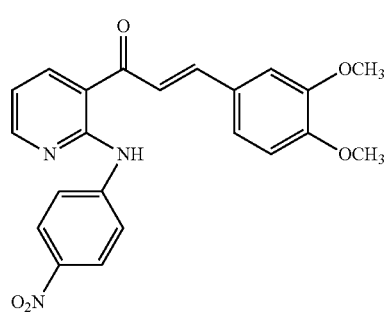 7r
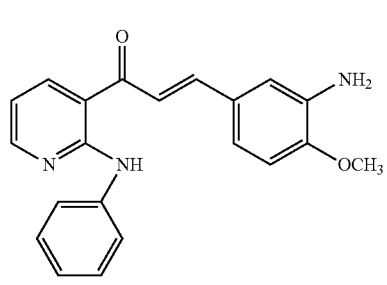 7s
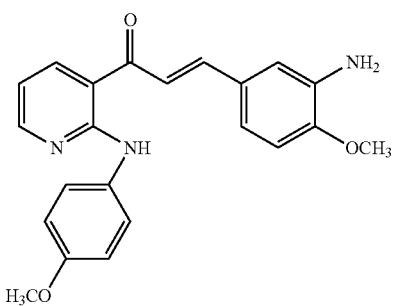 7t
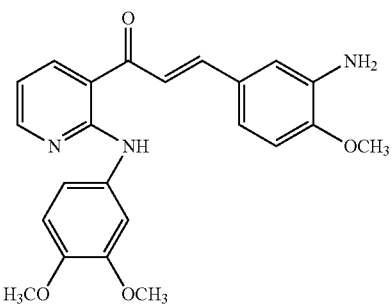 7u
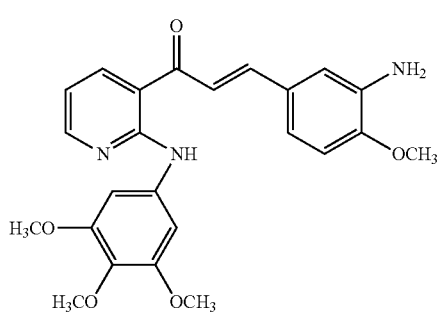 7v
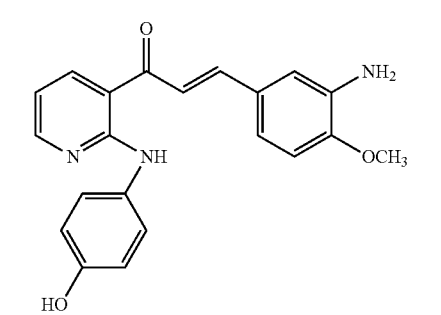 7w
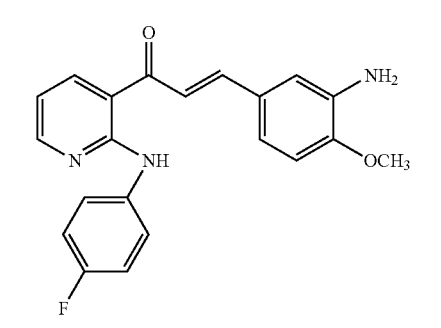 7x
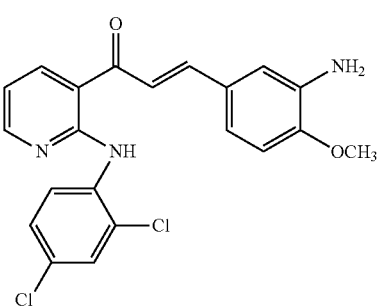 7y 7z
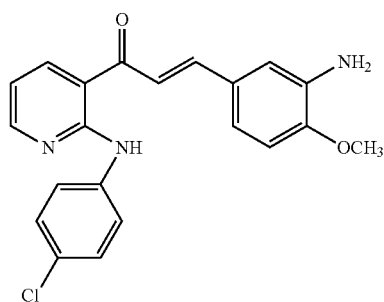
7aa
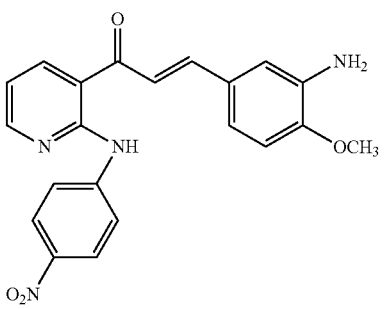
7ab
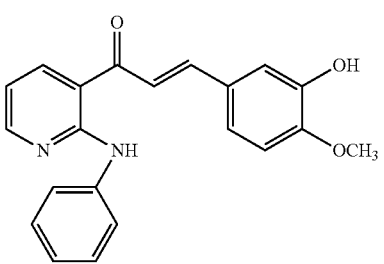
7ac
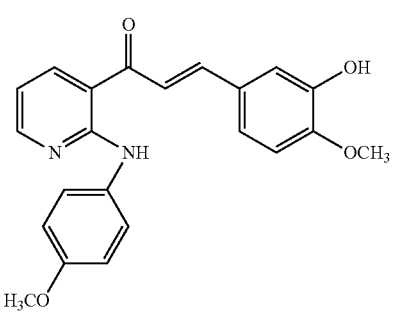
7ad
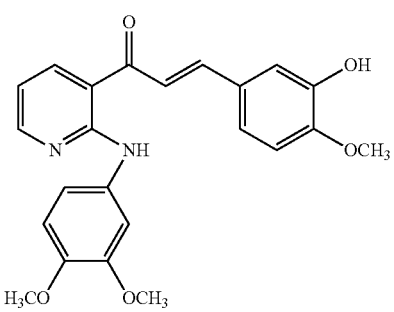
7ae
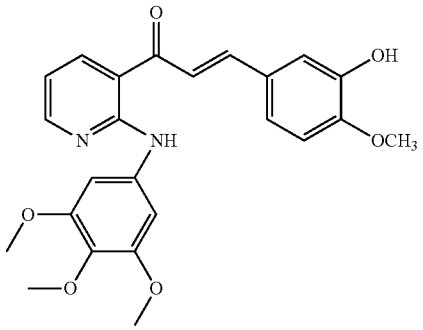
7af
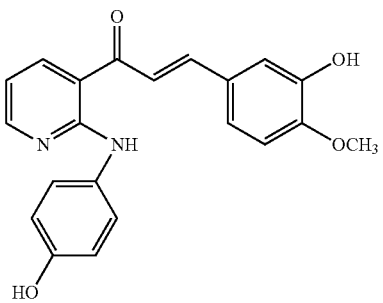
7ag
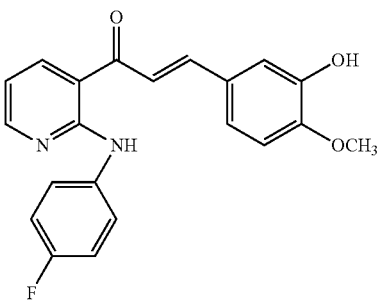
7ah
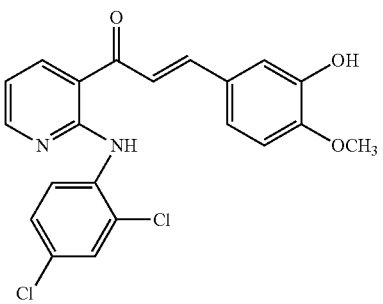
7ai
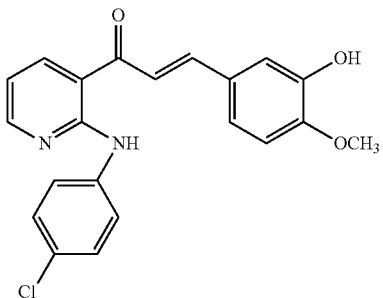

7aj 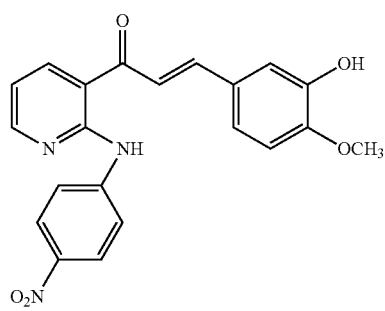
7ak 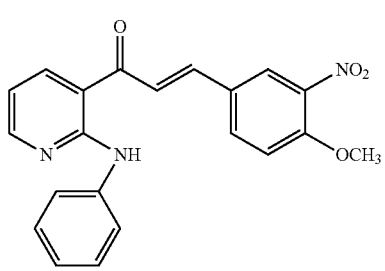
7al 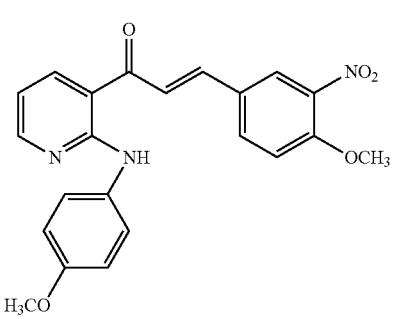
7am 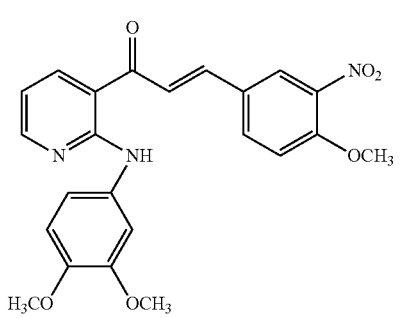
7an 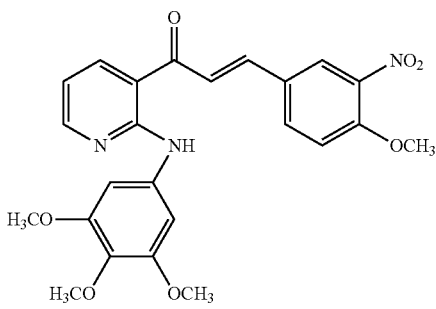
7ao 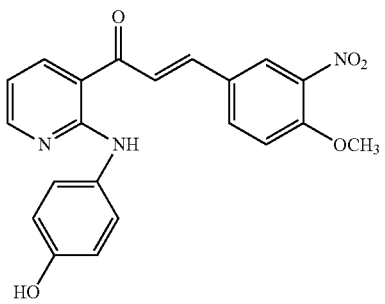
7ap 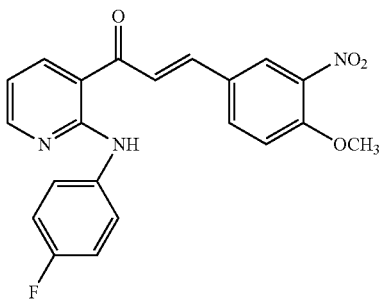
7aq 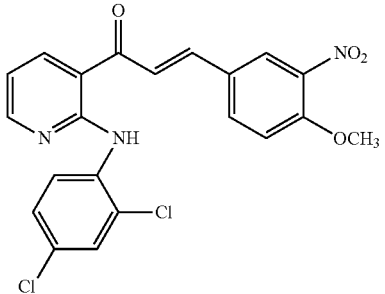
7ar 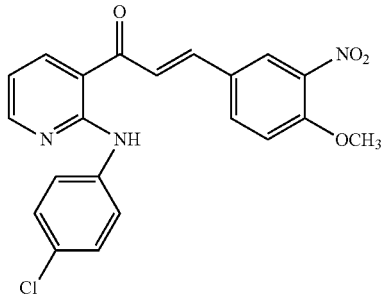
7as 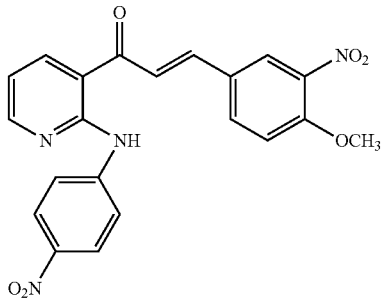

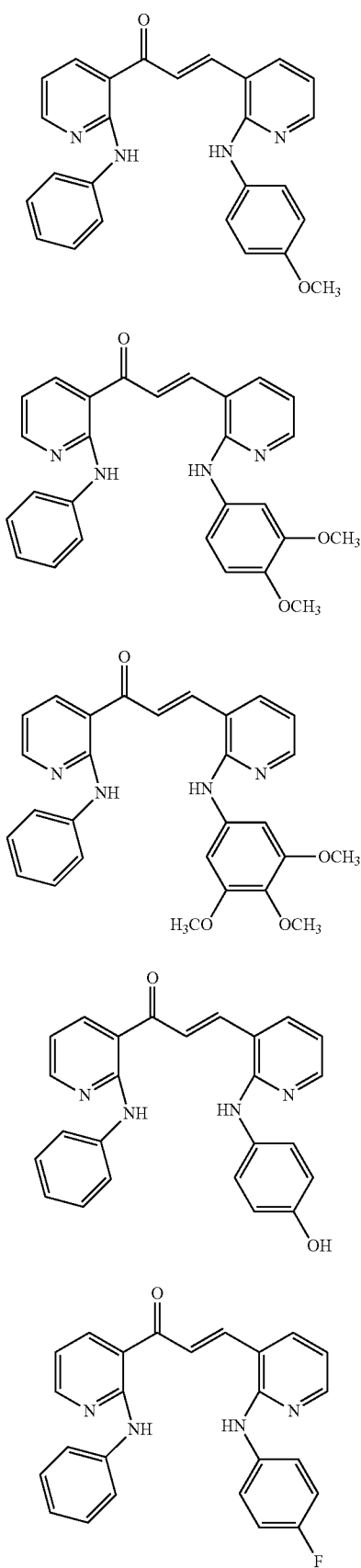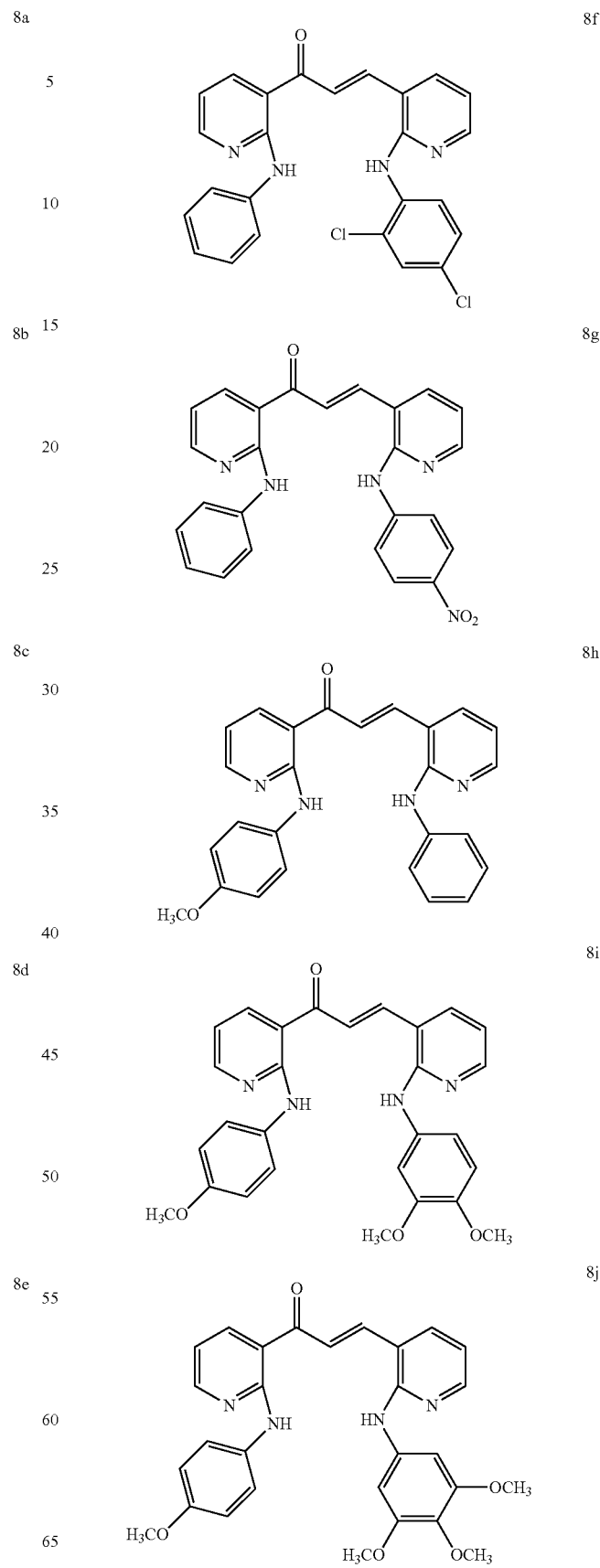

8k
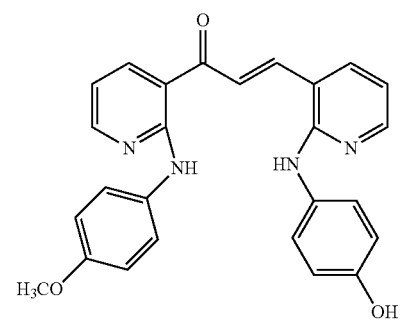
8l
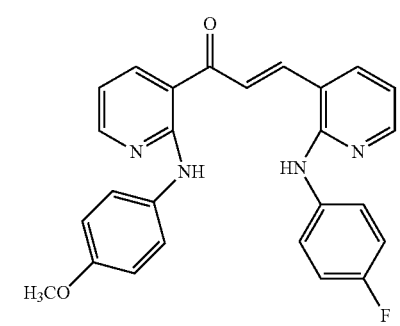
8m
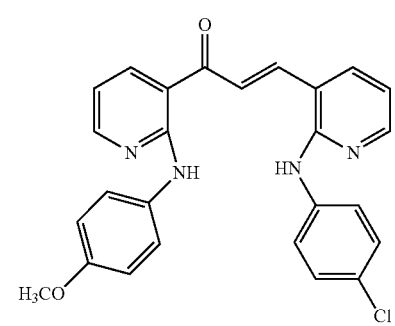
8n
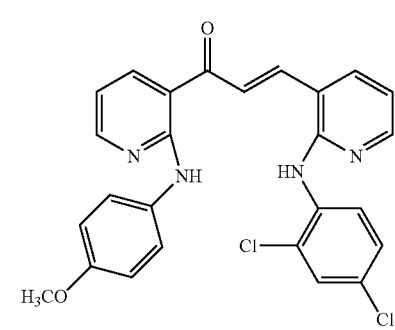
8o
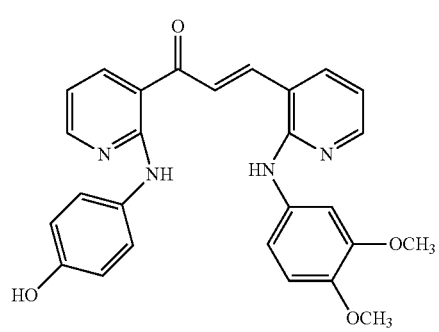
10p
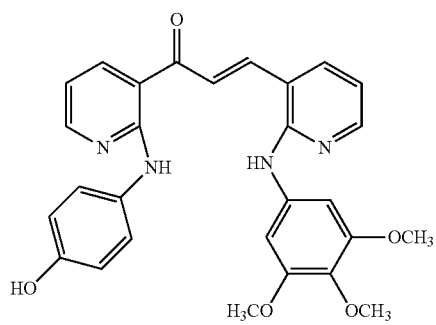
10q
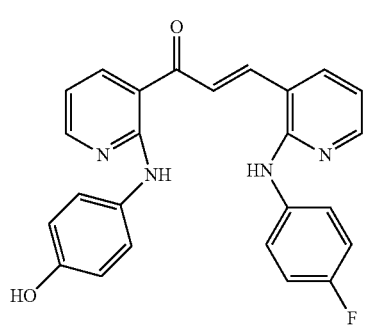
10r
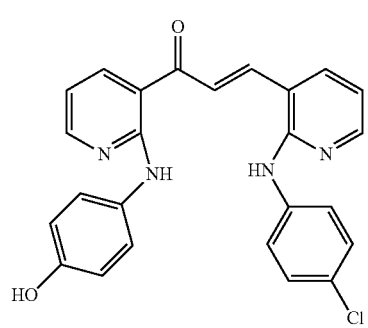
8s
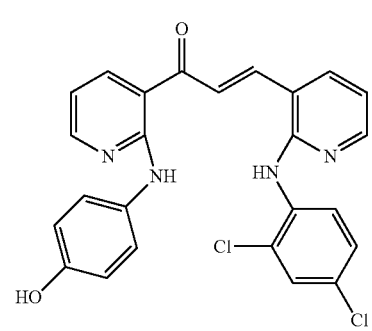
8t
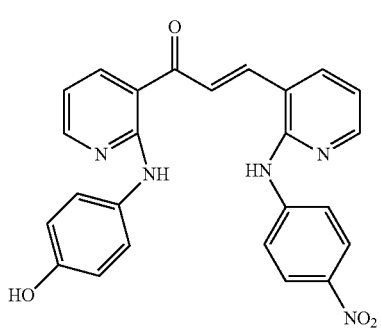

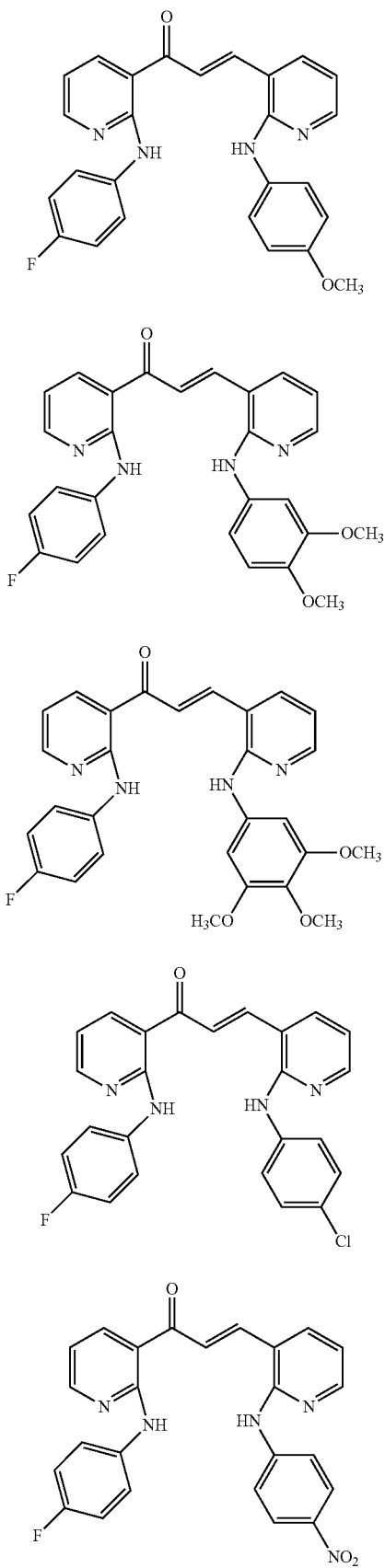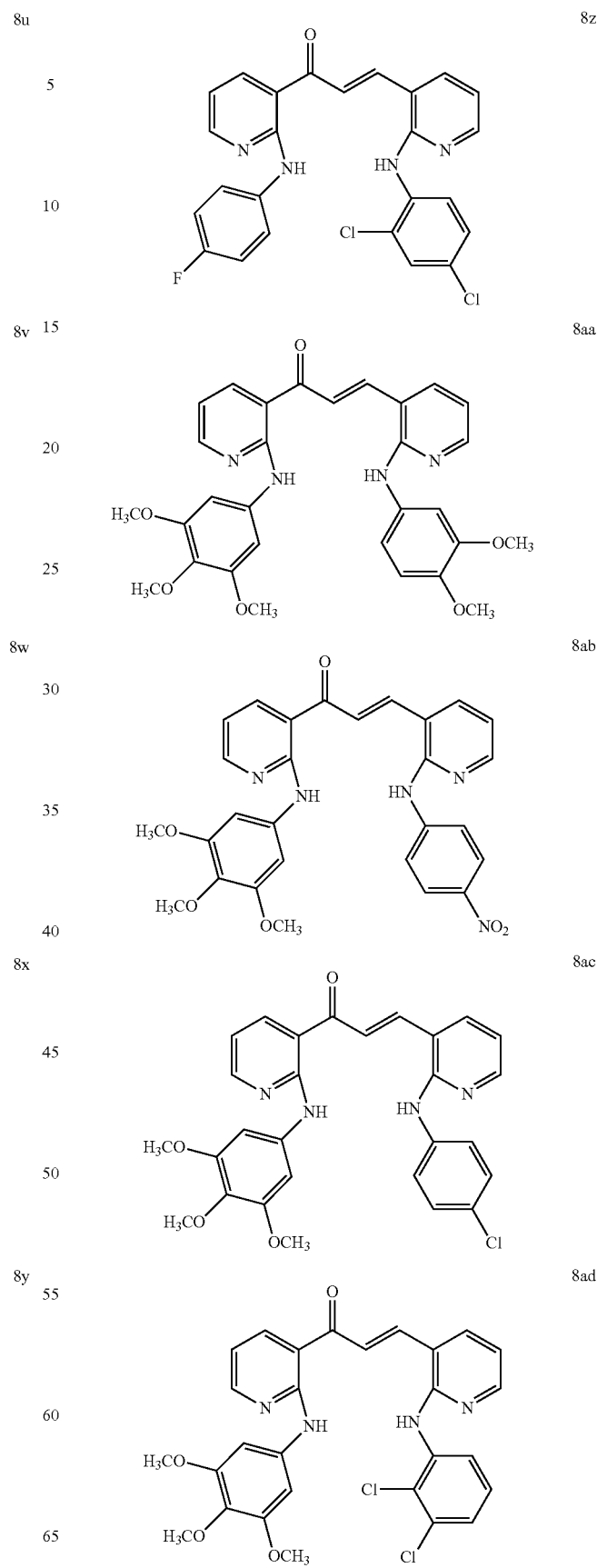

-continued

8ae

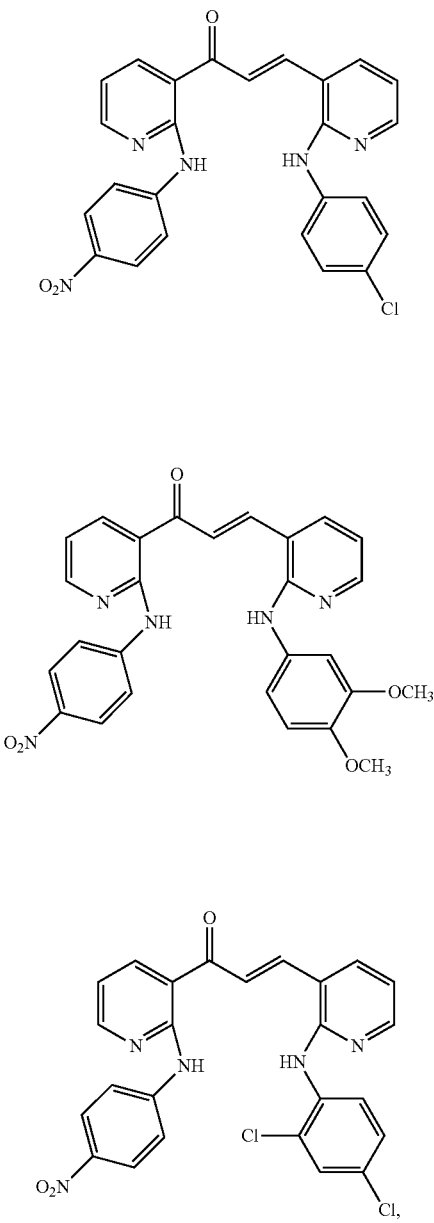

8af

8ag

4. A process for preparation of a 2-anilinonicotinyl based chalcone compound of general formula A

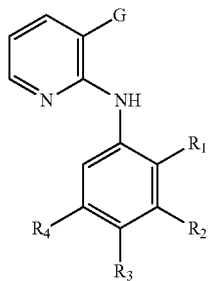

Formula A $R_1, R_2, R_3, R_4 = H$;
$R_1, R_2, R_4 = H, R_3 = NO_2$;
$R_1, R_2, R_4 = H, R_3 = OMe$;
$R_1, R_2, R_4 = H, R_3 = F$;
$R_1, R_2, R_4 = H, R_3 = Cl$;
$R_1, R_2, R_4 = H, R_3 = OH$;
$R_1, R_2 = H, R_4 = H, R_3 = OMe$;
$R_1, R_3 = Cl, R_4, R_2 = H$; or
$R_1 = H, R_2, R_3 = H, R_4 = OMe$;

and G =

A, B, C = OMe;
A, B = OMe, C = H;
A = NH2, B = OMe, C = H;
A = NO2, B = OMe; C = H;
A, C = H, B = OMe;
A, C = H, B = NH2; or
A, C = H, B = Cl;

X, Y = OMe, Z = H;
X, Y, Z = OMe;
X = H, Y = OMe, Z = OH;
X = H, Y = OMe, Z = NO_2; or
X = H, Y = OMe, Z = NH_2;

$R_1, R_2, R_3, R_4 = H$;
$R_1, R_2, R_4 = H, R_3 = NO_2$;
$R_1, R_2, R_4 = H, R_3 = OMe$;
$R_1, R_2, R_4 = H, R_3 = F$;
$R_1, R_2, R_4 = H, R_3 = Cl$;
$R_1, R_2, R_4 = H, R_3 = OH$;
$R_1, R_2 = H, R_4 = H, R_3 = OMe$;
$R_1, R_3 = Cl, R_4, R_2 = H$; or
$R_1 = H, R_2, R_3 = H, R_4 = OMe$.

and said process comprising the steps of:
i) reacting a compound of general formula 16a-i with substituted acetophenone of general formula 18a-g or a compound of general formula 17a-i with substituted aldehyde of general formula 19a-e or a compound of general formula 16a-i and 17a-l, 16a-i

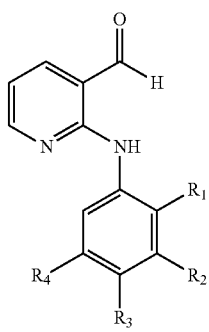

17a-i

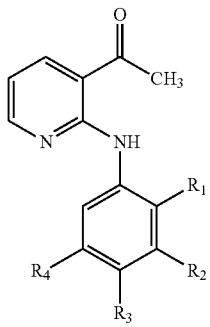

R₁, R₂, R₃, R₄ = H;
R₁, R₂, R₄ = H, R₃ = NO₂;
R₁, R₂, R₄ = H, R₃ = OMe;
R₁, R₂, R₄ = H, R₃ = F;
R₁, R₂, R₄ = H, R₃ = Cl;
R₁, R₂, R₄ = H, R₃ = OH;
R₁, R₂ = H, R₄ = H, R₃ = OMe;
R₁, R₃ = Cl, R₄, R₂ = H; or
R₁ = H, R₂, R₃ = H, R₄ = OMe;

19a-g

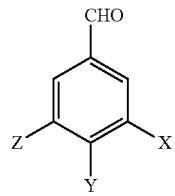

X, Y = OMe, Z = H
X, Y, Z = OME
X = H, Y = OMe, Z = OH
X = H, Y = OMe, Z = NO₂
X = H, Y = OMe, Z = NH₂

18a-e

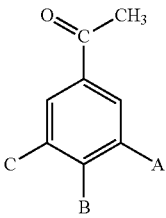

A, B, C = OMe
A, B = OMe, C = H
A = NH2, B = OMe, C = H
A = NO2, B = OMe; C = H
A, C = H, B = OMe
A, C = H, B = NH₂
A, C = H, B = Cl in an alcoholic solvent in the presence of barium hydroxide at a temperature ranging between 20-40° C. for a period of about 6 h, followed by the removal of organic solvent and neutralization by inorganic (HCl), and ii) extracting the reaction mixture with organic solvent selected form ethyl acetate or dichloromethane and evaporating the organic solvent to obtain the resultant crude product and purifying it by chromatographic method to obtain the desired compounds of formulae 6a-6bk, 7a-as and 8a-as respectively.

5. A process according to claim 4 wherein the alcoholic solvent used is selected from methanol or ethanol.

\* \* \* \* \*